(12) United States Patent
Porteus et al.

(10) Patent No.: US 11,851,652 B2
(45) Date of Patent: Dec. 26, 2023

(54) COMPOSITIONS COMPRISING CHEMICALLY MODIFIED GUIDE RNAS FOR CRISPR/CAS-MEDIATED EDITING OF HBB

(71) Applicant: The Board of Trustees of the Leland Stanford Junior University, Stanford, CA (US)

(72) Inventors: Matthew H. Porteus, Stanford, CA (US); Ayal Hendel, Stanford, CA (US); Joe Clark, Stanford, CA (US); Rasmus O. Bak, Stanford, CA (US); Daniel E. Ryan, Santa Clara, CA (US); Douglas J. Dellinger, Santa Clara, CA (US); Robert Kaiser, Santa Clara, CA (US); Joel Myerson, Santa Clara, CA (US)

(73) Assignees: THE BOARD OF TRUSTEES OF THE LELAND STANFORD JUNIOR, Stanford, CA (US); UNIVERSITY and AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 17/694,361

(22) Filed: Mar. 14, 2022

(65) Prior Publication Data
US 2022/0195427 A1 Jun. 23, 2022

Related U.S. Application Data

(63) Continuation of application No. 15/724,073, filed on Oct. 3, 2017, now Pat. No. 11,306,309, which is a continuation of application No. PCT/US2016/026028, filed on Apr. 5, 2016.

(60) Provisional application No. 62/160,545, filed on May 12, 2015, provisional application No. 62/143,729, filed on Apr. 6, 2015.

(51) Int. Cl.
| | |
|---|---|
| *C12N 15/11* | (2006.01) |
| *C12N 9/22* | (2006.01) |
| *C12N 9/96* | (2006.01) |
| *C12N 15/90* | (2006.01) |

(52) U.S. Cl.
CPC ............... *C12N 15/11* (2013.01); *C12N 9/22* (2013.01); *C12N 9/96* (2013.01); *C12N 15/111* (2013.01); *C12N 15/907* (2013.01); *C12N 2310/10* (2013.01); *C12N 2310/20* (2017.05); *C12N 2310/315* (2013.01); *C12N 2310/321* (2013.01); *C12N 2310/346* (2013.01); *C12N 2310/531* (2013.01); *C12N 2320/51* (2013.01)

(58) Field of Classification Search
CPC .......... C12N 9/22; C12N 9/96; C12N 15/111; C12N 15/907
See application file for complete search history.

(56) References Cited

U.S. PATENT DOCUMENTS

| | | |
|---|---|---|
| 5,032,401 A | 7/1991 | Jamas et al. |
| 5,607,677 A | 3/1997 | Jamas et al. |
| 7,371,580 B2 | 5/2008 | Yakhini et al. |
| 8,202,983 B2 | 6/2012 | Dellinger et al. |
| 8,906,616 B2 | 12/2014 | Zhang et al. |
| 9,822,407 B2 | 11/2017 | Joung et al. |
| 10,337,001 B2 | 7/2019 | Ryan et al. |
| 10,767,175 B2 | 9/2020 | Dellinger et al. |
| 10,900,034 B2 | 1/2021 | Ryan et al. |
| 11,193,141 B2 | 12/2021 | Dever et al. |
| 11,306,309 B2 | 4/2022 | Porteus et al. |
| 11,535,846 B2 | 12/2022 | Porteus et al. |
| 2005/0281781 A1 | 12/2005 | Ostroff |
| 2010/0076183 A1 | 3/2010 | Dellinger et al. |
| 2014/0090113 A1 | 3/2014 | Cogan et al. |
| 2014/0090116 A1 | 3/2014 | Ainley et al. |
| 2014/0170753 A1 | 6/2014 | Zhang |
| 2014/0242664 A1 | 8/2014 | Zhang et al. |
| 2014/0273037 A1 | 9/2014 | Wu |
| 2014/0273226 A1 | 9/2014 | Wu |
| 2014/0273232 A1 | 9/2014 | Zhang et al. |
| 2014/0273233 A1 | 9/2014 | Chen et al. |
| 2014/0273235 A1 | 9/2014 | Voytas et al. |
| 2014/0294773 A1 | 10/2014 | Brouns et al. |
| 2014/0295555 A1 | 10/2014 | Joung et al. |
| 2014/0295557 A1 | 10/2014 | Joung et al. |
| 2014/0309487 A1 | 10/2014 | Lee et al. |
| 2014/0310828 A1 | 10/2014 | Lee et al. |
| 2014/0349400 A1 | 11/2014 | Jakimo et al. |
| 2014/0357523 A1 | 12/2014 | Zeiner et al. |
| 2014/0364333 A1 | 12/2014 | Wu et al. |

(Continued)

FOREIGN PATENT DOCUMENTS

| | | |
|---|---|---|
| CN | 103614415 A | 3/2014 |
| EP | 2800811 A1 | 11/2014 |

(Continued)

OTHER PUBLICATIONS

Addgene, "pX330-U6-Chimeric_BB-CBh-hSpCas9," Internet Archive Wayback Machine entry for http://addgene.org/42230/ on Mar. 14, 2015.

(Continued)

*Primary Examiner* — Samuel C Woolwine
*Assistant Examiner* — Tiffany Nicole Grooms
(74) *Attorney, Agent, or Firm* — Kilpatrick Townsend & Stockton LLP

(57) ABSTRACT

Provided herein are methods for inducing CRISPR/Cas-based gene regulation (e.g., genome editing or gene expression) of a target nucleic acid (e.g., target DNA or target RNA) in a cell. The methods include using modified single guide RNAs (sgRNAs) that enhance gene regulation of the target nucleic acid in a primary cell for use in ex vivo therapy or in a cell in a subject for use in in vivo therapy. Additionally, provided herein are methods for preventing or treating a genetic disease in a subject by administering a sufficient amount of a modified sgRNA to correct a mutation in a target gene associated with the genetic disease.

22 Claims, 25 Drawing Sheets

Specification includes a Sequence Listing.

(56) References Cited

U.S. PATENT DOCUMENTS

| | | |
|---|---|---|
| 2015/0044191 A1 | 2/2015 | Liu et al. |
| 2015/0044192 A1 | 2/2015 | Liu et al. |
| 2015/0044772 A1 | 2/2015 | Zhao |
| 2015/0064149 A1 | 3/2015 | West et al. |
| 2015/0064708 A1 | 3/2015 | Sastry-Dent et al. |
| 2015/0067921 A1 | 3/2015 | Cogan et al. |
| 2015/0071906 A1 | 3/2015 | Liu et al. |
| 2015/0071946 A1 | 3/2015 | Solyom et al. |
| 2015/0079680 A1 | 3/2015 | Bradley et al. |
| 2015/0098954 A1 | 4/2015 | Hyde et al. |
| 2015/0118216 A1 | 4/2015 | Liu et al. |
| 2015/0128307 A1 | 5/2015 | Sastry-Dent et al. |
| 2015/0128308 A1 | 5/2015 | Sastry-Dent et al. |
| 2015/0128309 A1 | 5/2015 | Sastry-Dent et al. |
| 2015/0133315 A1 | 5/2015 | Jacobson et al. |
| 2015/0140664 A1 | 5/2015 | Byrne et al. |
| 2015/0156996 A1 | 6/2015 | Fahrenkrug et al. |
| 2015/0315252 A1 | 11/2015 | Haugwitz et al. |
| 2015/0315576 A1 | 11/2015 | Caliando et al. |
| 2015/0322432 A1 | 11/2015 | Anderson et al. |
| 2015/0344836 A1 | 12/2015 | Finer et al. |
| 2016/0030477 A1 | 2/2016 | Conway et al. |
| 2016/0046959 A1 | 2/2016 | Landel et al. |
| 2016/0090622 A1 | 3/2016 | Liu et al. |
| 2016/0138027 A1 | 5/2016 | Gan et al. |
| 2016/0168592 A1 | 6/2016 | Church et al. |
| 2016/0206566 A1 | 7/2016 | Lu et al. |
| 2016/0257974 A1 | 9/2016 | Bradley et al. |
| 2016/0289675 A1 | 10/2016 | Ryan et al. |
| 2016/0298097 A1 | 10/2016 | Chavez et al. |
| 2016/0339064 A1 | 11/2016 | Kovarik et al. |
| 2016/0340661 A1 | 11/2016 | Cong et al. |
| 2017/0051296 A1 | 2/2017 | Beetham et al. |
| 2017/0166893 A1 | 6/2017 | Doudna et al. |
| 2017/0298383 A1 | 10/2017 | Albertsen et al. |
| 2017/0314015 A1 | 11/2017 | Friedland et al. |
| 2018/0051281 A1 | 2/2018 | Ryan et al. |
| 2018/0119140 A1 | 5/2018 | Porteus et al. |
| 2020/0339980 A1 | 10/2020 | Dellinger et al. |
| 2021/0079389 A1 | 3/2021 | Ryan et al. |
| 2022/0195425 A1 | 6/2022 | Porteus et al. |
| 2022/0195426 A1 | 6/2022 | Porteus et al. |

FOREIGN PATENT DOCUMENTS

| | | |
|---|---|---|
| EP | 2892321 A2 | 7/2015 |
| EP | 2893006 A1 | 7/2015 |
| EP | 3241902 B1 | 2/2018 |
| WO | 2013/126794 A1 | 8/2013 |
| WO | 2013/141680 A1 | 9/2013 |
| WO | 2013/142578 A1 | 9/2013 |
| WO | 2013/176772 A1 | 11/2013 |
| WO | 2013/176844 A1 | 11/2013 |
| WO | 2014/039684 A1 | 3/2014 |
| WO | 2014/039702 A2 | 3/2014 |
| WO | 2014/065596 A1 | 5/2014 |
| WO | 2014/071219 A1 | 5/2014 |
| WO | 2014/089290 A1 | 6/2014 |
| WO | 2014/089513 A1 | 6/2014 |
| WO | 2014/089533 A2 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093688 A1 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/099744 A1 | 6/2014 |
| WO | 2014/099750 A2 | 6/2014 |
| WO | 2014/144288 A1 | 9/2014 |
| WO | 2014/144592 A2 | 9/2014 |
| WO | 2014/144761 A2 | 9/2014 |
| WO | 2014/145599 A2 | 9/2014 |
| WO | 2014/150624 A1 | 9/2014 |
| WO | 2014/152432 A2 | 9/2014 |
| WO | 2014/153118 A1 | 9/2014 |
| WO | 2014/039970 A9 | 10/2014 |
| WO | 2014/159719 A1 | 10/2014 |
| WO | 2014/165349 A1 | 10/2014 |
| WO | 2014/165825 A2 | 10/2014 |
| WO | 2014/172458 A1 | 10/2014 |
| WO | 2014/172470 A2 | 10/2014 |
| WO | 2014/186585 A2 | 11/2014 |
| WO | 2014/191128 A1 | 12/2014 |
| WO | 2014/191518 A1 | 12/2014 |
| WO | 2014/191521 A2 | 12/2014 |
| WO | 2014/197568 A2 | 12/2014 |
| WO | 2014/201015 A2 | 12/2014 |
| WO | 2014/204725 A1 | 12/2014 |
| WO | 2014/204726 A1 | 12/2014 |
| WO | 2015/006294 A2 | 1/2015 |
| WO | 2015/006437 A1 | 1/2015 |
| WO | 2015/006498 A2 | 1/2015 |
| WO | 2015/006747 A2 | 1/2015 |
| WO | 2015/013583 A2 | 1/2015 |
| WO | 2015/026883 A1 | 2/2015 |
| WO | 2015/026885 A1 | 2/2015 |
| WO | 2015/026886 A1 | 2/2015 |
| WO | 2015/030881 A1 | 3/2015 |
| WO | 2015/033293 A1 | 3/2015 |
| WO | 2015/035136 A2 | 3/2015 |
| WO | 2015/035139 A2 | 3/2015 |
| WO | 2015/035162 A2 | 3/2015 |
| WO | 2015/040075 A1 | 3/2015 |
| WO | 2015/052133 A1 | 4/2015 |
| WO | 2015/052231 A2 | 4/2015 |
| WO | 2015/053995 A1 | 4/2015 |
| WO | 2015/054253 A1 | 4/2015 |
| WO | 2015/054375 A2 | 4/2015 |
| WO | 2015/066636 A2 | 5/2015 |
| WO | 2015/066637 A1 | 5/2015 |
| WO | 2015/070083 A1 | 5/2015 |
| WO | 2015/075056 A1 | 5/2015 |
| WO | 2015/089277 A1 | 6/2015 |
| WO | 2015/089351 A1 | 6/2015 |
| WO | 2015/089354 A1 | 6/2015 |
| WO | 2015/089406 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2014/204728 A1 | 7/2015 |
| WO | 2015138510 | 9/2015 |
| WO | 2015/184259 A1 | 12/2015 |
| WO | 2015/184262 A1 | 12/2015 |
| WO | 2015/184268 A1 | 12/2015 |
| WO | 2015/200334 A1 | 12/2015 |
| WO | 2015/200378 A1 | 12/2015 |
| WO | 2015/200555 A2 | 12/2015 |
| WO | 2015/200725 A1 | 12/2015 |
| WO | 2015191693 | 12/2015 |
| WO | 2014/204723 A9 | 2/2016 |
| WO | 2016/022363 A2 | 2/2016 |
| WO | 2014/204724 A9 | 3/2016 |
| WO | 2016/033246 A1 | 3/2016 |
| WO | 2016/033315 A1 | 3/2016 |
| WO | 2016/046288 A1 | 3/2016 |
| WO | 2016/049024 A2 | 3/2016 |
| WO | 2016/049163 A2 | 3/2016 |
| WO | 2016/049251 A1 | 3/2016 |
| WO | 2016/049657 A1 | 3/2016 |
| WO | 2016/057755 A1 | 4/2016 |
| WO | 2016/057821 A2 | 4/2016 |
| WO | 2016/057835 A2 | 4/2016 |
| WO | 2016/057951 A2 | 4/2016 |
| WO | 2016/069282 A1 | 5/2016 |
| WO | 2016/069283 A1 | 5/2016 |
| WO | 2016/070037 A2 | 5/2016 |

(56) References Cited

FOREIGN PATENT DOCUMENTS

| WO | 2016/073079 A2 | 5/2016 |
|---|---|---|
| WO | 2016/089433 A1 | 6/2016 |
| WO | 2016100951 | 6/2016 |
| WO | 2017/104404 A1 | 6/2017 |
| WO | 2017/105991 A1 | 6/2017 |
| WO | 2017/106414 A1 | 6/2017 |
| WO | 2017/106569 A1 | 6/2017 |
| WO | 2017/106657 A1 | 6/2017 |
| WO | 2017/106767 A1 | 6/2017 |

OTHER PUBLICATIONS

Barrangou, R. and A. May, "Unraveling the potential of CRISPR-Cas9 for gene therapy," Expert Opinion on Biological Therapy, 15(3):311-314, 2015.
Barrangou, R. et al., "Advances in CRISPR-Cas9 genome engineering: lessons learned from RNA interference," Nucleic Acids Res., 43(7):3407-19, 2015.
Basila, M. et al., "Minimal 2'-O-methyl phosphorothioate linkage modification pattern of synthetic guide RNAs for increased stability and efficient CRISPR-Cas9 gene editing avoiding cellular toxicity," PLoS ONE, 12(11):e0188593, 2017.
Behlke, "Optimized, chemically-modified crRNA:tracrRNA complexes for CRISPR gene editing," Retrieved from the Internet: URL:http://crispr-congress.comjwp-content/uploads/sites/76/2015/10/Mark-Behlke-Final-Presentation.pdf, Feb. 24, 2016, pp. 1-31.
Behlke, M., "Chemical Modification of siRNAs for In Vivo Use," Oligonucleotides, 18:305-320, 2008.
Belfort et al., "Homing Endonucleases: Keeping the House in Order," Nucleic Acids Research, vol. 25, No. 17, 1997, 3379-3388.
Bennet, C. and E. Swayze, "RNA Targeting Therapeutics: Molecular Mechanisms of Antisense Oligonucleotides as a Therapeutic Platform," Annu. Rev. Pharmacol. Toxicol., 50:259-93, 2010.
Bertoni, C., "Emerging gene editing strategies for Duchenne muscular dystrophy targeting stem cells," Frontiers in Physiology, 5:148, 2014.
Bisaria et al., "Lessons from Enzyme Kinetics Reveal Specificity Principles for RNA-guided Nucleases in RNA Interference and CRISPR-based Genome Editing," Cell Systems, vol. 4, Jan. 25, 2017, 21-29.
Briner et al., "Guide RNA Functional Modules Direct Cas9 Activity and Orthogonality," Molecular Cell, vol. 56, Oct. 23, 2014, 333-339.
Burnett, J. and J. Rossi, "RNA-Based Therapeutics: Current Progress and Future Prospects," Chemistry & Biology, 19:60-71, 2012.
Chen et al., "Dynamic Imaging of Genomic Loci in Living Human Cells by an Optimized CRISPR/Cas System," Cell, vol. 155, Dec. 19, 2013, 1479-1491.
Cho et al., "Analysis of Off-target Effects of CRISPR/Cas-derived RNA-guided Endonucleases and Nickases," Genome Research, vol. 24, 2014, 132-141.
Cho et al., "Targeted Genome Engineering in Human Cells with the Cas9 RNA-guided Endonuclease," Nature Biotechnology, vol. 31, No. 3, Mar. 2013, 230-232.
Cong et al., "Multiplex Genome Engineering Using CRISPR/Cas Systems," Science vol. 339, No. 6121, 2013, 819-823.
Corey, D., "Chemical modification: the key to clinical application of RNA interference?" J. Clin. Invest., 117(12):2615-22, 2007.
Corey, D., "RNA learns from antisense," Nature Chemical Biology, 3(1):8-11, 2007.
Cradick et al., "CRISPR/Cas9 Systems Targeting β-globin and CCR5 Genes have Substantial off-target Activity," Nucleic Acids Research, vol. 41, No. 20, 2013, 9584-9592.
CRISPR, "CRISPR Design," http://crispr.mit.edu, 2017, 1 page.
Davis et al., "Small Molecule-Triggered Cas9 Protein with Improved Genome-editing Specificity," Nature Chemical Biology, vol. 11, May 2015, 316-318.
Deleavey, G. et al., "Designing Chemically Modified Oligonucleotides for Targeted Gene Silencing," Chem. Biol., 19(8):937-54, 2012.
Dellinger et al., "Solid-Phase Chemical Synthesis of Phosphonoacetate and Thiophosphonoacetate Oligodeoxynucleotides," J. Am. Chem. Soc., vol. 125, 2003, 940-950.
Dellinger et al., "Streamlined Process for the Chemical Synthesis of RNA Using 2'-O-Thionocarbamate-Protected Nucleoside Phosphoramidites in the Solid Phase," Journal of the American Chemical Society, vol. 133, 2011, 11540-11556.
Deng et al., "CASFISH: CRISPR/Cas9-Mediated In Situ Labeling of Genomic Loci in Fixed Cells," Proceedings of The National Academy of Sciences (PNAS) vol. 112, No. 38, Sep. 22, 2015, 11870-11875.
Doench et al., "Optimized sgRNA Design to Maximize Activity and Minimize Off-target Effects of CRISPR-Cas9," Nature Biotechnology, vol. 34, No. 2, Feb. 2016, 184-191.
Doudna, J. and E. Charpentier, "The new frontier of genome engineering with CRISPR-Cas9," Science, 346(6213):1077 and 1258096, 2014.
Doyon et al., "Enhancing Zinc-Finger-Nuclease Activity with Improved Obligate Heterodimeric Architectures," Nature Methods, vol. 8, No. 1, Jan. 2011, 74-79.
Ei-Sagheer et al., "Click Chemistry with DNA," Chemical Society Reviews, vol. 39, 2010, 1388-1405.
Extended European Search Report dated Jun. 13, 2018 for EP Application No. 15866342.7, 14 pages.
Frock et al., "Genome-Wide Detection of DNA Double-Stranded Breaks Induced by Engineered Nucleases," Nature Biotechnology, vol. 33, No. 2, Feb. 2015, 179-186.
Fu et al., "Distinct Patterns of Cas9 Mismatch Tolerance in Vitro and in Vivo," Nucleic Acids Research, vol. 44, No. 11, 2016, 5365-5377.
Fu et al., "High-frequency off-target Mutagenesis Induced by CRISPR-Cas Nucleases in Human Cells," Nature Biotechnology, vol. 31, No. 9, Sep. 2013, 822-826.
Fu et al., "Improving CRISPR-Cas Nuclease Specificity Using Truncated Guide RNAs," Nature Biotechnology, vol. 32, No. 3, Mar. 2014, 279-284.
Gao et al., "Single Cas9 Nickase Induced Generation of NRAMP1 Knockin Cattle with Reduced off-target Effects," Genome Biology, vol. 18, No. 13, 2017, 1-15.
Gasiunas et al., "Cas9-crRNA Ribonucleoprotein Complex Mediates Specific DNA Cleavage for Adaptive Immunity in Bacteria," Proc. Natl. Acad. Sci., vol. 109, No. 39, Sep. 4, 2012, E2579-E2586.
Gori et al., "Delivery and Specificity of CRISPR/Cas9 Genome Editing Technologies for Human Gene Therapy," Human Gene Therapy, vol. 26, No. 7, 2015, 443-451.
Guilinger et al., "Fusion of Catalytically Inactive Cas9 to FokI Nuclease Improves the Specificity of Genome Modification," Nature Biotechnology, vol. 32, No. 6, Jun. 2014, 577-582.
Haeussler et al., "Evaluation of off-Target and on-Target Scoring Algorithms and Integration into The Guide RNA Selection Tool CRISPOR," Genome Biology, vol. 17, No. 148, 2016, 1-12.
Havlicek et al., "Re-engineered RNA-Guided FokI-Nucleases for Improved Genome Editing in Human Cells," Molecular Therapy, vol. 25, No. 2, Feb. 2017, 342-355.
Hendel et al., "Chemically modified guide RNAs enhance CRISPR-Cas genome editing in human primary cells," Nature Biotechnology, vol. 33, No. 9, Sep. 2015, pp. 985-989.
Hendel, A. et al., Supplementary materials for "Chemically Modified Guide RNAs Enhance CRISPR-Cas Genome Editing in Human Primary Cells," Nat. Biotechnol., 33(9):985-989, 2015.
Hendel et al., "Quantifying Genome-Editing Outcomes at Endogenous Loci using SMRT Sequencing," Cell Rep., vol. 7, No. 1, Apr. 10, 2014, 293-305.
Hruscha et al., "Efficient CRISPR/Cas9 Genome Editing with Low off-target effects in Zebrafish," Development, vol. 140, 2013, 4982-4987.
Hsu et al., "DNA Targeting Specificity of RNA-guided Cas9 Nucleases," Nature Biotechnology, vol. 31, No. 9, Sep. 2013, 827-832.
Hsu, P. et al., "Development and Applications of CRISPR-Cas9 for Genome Engineering," Cell, 157:1262-78, 2014.

(56) References Cited

OTHER PUBLICATIONS

Hu et al., "Detecting DNA Double-stranded Breaks in Mammalian Genomes by Linear Amplification-mediated high-throughput Genome-wide Translocation Sequencing," Nature Protocols, vol. 11, No. 5, 2016, 853-871.
Hwang et al., "Efficient In Vivo Genome Editing Using RNA-Guided Nucleases," Nat Biotechnol., vol. 31, No. 3, Mar. 2013, 227-229.
International Search Report and Written Opinion dated Apr. 19, 2016 for PCT Application No. PCT/US2015/000143, 12 pages.
International Search Report dated Jul. 22, 2016 for corresponding PCT Application No. PCT/US2016/026028, 7 pages.
Iyer et al., "Off-target Mutations are Rare in Cas9-modified Mice," Nature Methods, vol. 12, No. 6, Jun. 2015, 479.
James Poole Limited, Timeline of European Patent No. 3280803 B1 and priority and filing dates for International Patent Application Publication No. WO 2016/089433 A1, submitted in James Poole Limited's opposition to European Patent No. 3280803 B1 on Feb. 28, 2022, 1 page.
Jiang et al., "A Cas9-guide RNA Complex Preorganized for Target DNA Recognition," Science, vol. 348, Issue 6242, Jun. 26, 2015, 1477-1481.
Jinek et al., "A Programmable Dual-RNA-Guided DNA Endonuclease in Adaptive Bacterial Immunity," Science, vol. 337, 2012, 816-821.
Jinek et al., "RNA-Programmed Genome Editing in Human Cells," eLife Research Article, Genomics and evolutionary biology, Human biology and medicine, Jan. 29, 2013, 1-9.
Jinek et al., "Supplementary Materials for a Programmable Dual-RNA-Guided DNA Endonuclease in Adaptive Bacterial Immunity," Science, vol. 337, 2012, 37 pages.
Jinek, M. et al., "Structures of Cas9 Endonucleases Reveal RNA-Mediated Conformational Activation," Science; 343(6176), 2014.
Jinek, M. et al., Supplementary materials for "Structures of Cas9 Endonucleases Reveal RNA-Mediated Conformational Activation," Science; 343(6176), 2014.
Karvelis et al., "crRNA and tracrRNA guide Cas9-mediated DNA Interference *Streptococcus thermophilus*," RNA Biology, vol. 10, No. 5, May 2013, 841-851.
Kim et al., "Digenome-seq: Genome-wide Profiling of CRISPR-Cas9 off-target Effects in Human Cells," Nature Methods, vol. 12, No. 3, Mar. 2015, 237-243.
Kim et al., "Genome-wide Analysis Reveals Specificities of Cpf1 Endonucleases in Human Cells," Nature Biotechnology, vol. 34, No. 8, Aug. 2016, 863-868.
Kim et al., "Genome-Wide Target Specificities of CRISPR-Cas9 Nucleases Revealed by Multiplex Digenome-seq," Genome Research, vol. 26, 2016, 406-415.
Kim et al., "Highly Efficient RNA-Guided Genome Editing in Human Cells via Delivery of Purified Cas9 Ribonucleoproteins," Genome Research, vol. 24, 2014, 1012-1019.
Kleinstiver et al., "Genome-wide Specificities of CRISPR-Cas Cpf1 Nucleases in Human Cells," Nature Biotechnology, vol. 34, No. 8, Aug. 2016, 869-874.
Kleinstiver et al., "High-fidelity CRISPR-Cas9 Nucleases with no Detectable Genome-wide off-target Effects," Nature, vol. 529, Jan. 28, 2016, 490-495.
Knight et al., "Dynamics of CRISPR-Cas9 Genome Interrogation in Living Cells," Science, vol. 350, Issue. 6262, Nov. 13, 2015, 823-826.
Komor et al., "Programmable Editing of a Target Base in Genomic DNA without Double-stranded DNA Cleavage," Nature, vol. 533, May 19, 2016, 420-424.
Koo et al., "Measuring and Reducing Off-Target Activities of Programmable Nucleases Including CRISPR-Cas9," Mol. Cells, vol. 38, No. 6, 2015, 475-481.
Krueger et al., "Synthesis and Properties of Size-expanded DNAs: Toward Designed, Functional Genetic Systems," Acc. Chem. Res., vol. 40, No. 2, Feb. 2007, 141-150.

Krützfeld, T et al., "Specificity, duplex degradation and subcellular localization of antagomirs," Nucleic Acids Res., 35(9):2885-92, 2007.
Kumar et al., "Template-Directed Oligonucleotide Strand Ligation, Covalent Intramolecular DNA Circularization and Catenation Using Click Chemistry," J. Am. Chem. Soc., vol. 129, No. 21, 2007, 6859-6864.
Kurreck, J. "Antisense technologies—Improvement through novel chemical modifications," Eur. J. Biochem., 270:1628-1644, 2003.
Kuscu et al., "Genome-wide Analysis Reveals Characteristics of Off-target Sites Bound by the Cas9 Endonuclease," Nature Biotechnology, vol. 32, No. 7, Jul. 2014, 677-683.
Kuznetsova, "Synthesis and properties of DNA duplexes containing hydrocarbon bridges instead of a nucleoside residue", Bioorganicheskaia khimiia/Akademiia nauk SSSR, vol. 14:12, 1988, 1656-1662.
Laganà, A. et al., "Synthetic RNAs for gene regulation: design principles and computational tools," Front. Bioeng. Biotechnol., 2:65, 2014.
Lahoud et al., "Enzymatic Synthesis of Structure-Free DNA with Pseudo Complementary Properties", Nucl. Acids Res. vol. 36, 2008, 3409-3419.
Lange et al., "Classical Nuclear Localization Signals: Definition, Function, and Interaction with Importin $\alpha^*$", J Biol. Chem., vol. 282, 2007, 5101-5105.
Larson et al., Real-Time Observation of Transcription Initiation and Elongation on an Endogenous Yeast Gene, Science, vol. 332, No. 6028, Apr. 22, 2011, 475-478.
Latorre, A. et al., "Modified RNAs in CRISPR/Cas9: An Old Trick Works Again," Angew. Chem. Int. Ed., 55(11):3548-50, 2016.
Ledford, "CRISPR, the Disruptor," Nature, vol. 522, 2015, 20-24.
Lee et al., "Nuclease target site selection for maximizing on-target activity and minimizing off-target effects in genome editing," Mol. Ther. vol. 24, 2016, 475-487.
Lennox, K. and M. Behlke, "Chemical modification and design of anti-miRNA oligonucleotides," Gene Therapy, 18:1111-20, 2011.
Li, B. et al., "Engineering CRISPR-Cpf1 crRNAs and mRNAs to maximize genome editing efficiency," Nat. Biomed. Eng., 1(5), doi:10.1038/s41551-017-0066, Epub May 10, 2017.
Li, Z. and T. Rana, "Therapeutic targeting of microRNAs: current status and future challenges," Nat. Rev. Drug Discov., 13(8):622-38, 2014.
Lim et al., "Structural Roles of Guide RNAs in the Nuclease Activity of Cas9 Endonuclease," Nature Communications, vol. 7, No. 13350, 2016, 1-8.
Lin et al., "CRISPR/Cas9 Systems have off-target Activity with Insertions or Deletions Between Target DNA and Guide RNA Sequences," Nucleic Acids Research, vol. 42, No. 11, 2014, 7473-7485.
Lonza, BioResearch NucleofectorTM 2b Manual, 2015, 20 pages.
Lujambio et al., "Genetic Unmasking of an Epigenetically Silenced MicroRNA in Human Cancer Cells," (Spanish National Cancer Centre) Cancer Res., vol. 67, No. 4, Feb. 15, 2007, 1424-1429.
Ma et al., "CRISPR-Cas9 Nuclear Dynamics and Target Recognition in Living Cells," J. Cell Biol, vol. 214, No. 5, 2016, 529-537.
Mali et al., "CAS9 Transcriptional Activators for Target Specificity Screening and Paired Nickases for Cooperative Genome Engineering," Nature Biotechnology, vol. 31, No. 9, 2013, 833-838.
Mali et al., "RNA-Guided Human Genome Engineering via Cas9," Science, vol. 339, No. 6121, 2013, 823-826.
Mali, P. et al., Supplementary materials for "CAS9 transcriptional activators for target specificity screening and paired nickcases for cooperative genome engineering," Nature Biotechnology, 31(9):833-38, 2013.
Mali, P. et al., "Cas9 as versatile tool for engineering biology," Nature Methods, 10(10):957-963, 2013.
Miller et al., "An Improved Zinc-finger Nuclease Architecture for Highly Specific Genome Editing," Nature Biotechnology, vol. 25, No. 7, Jul. 2007, 778-785.
Mojibul et al., "DNA-associated click chemistry," Sci. China Chem, The Frontiers of Chemical Biology and Synthesis, vol. 57, No. 2, Feb. 2014, 215-231.
New England Biolabs Inc., "Restriction Endonucleases," New England Biolabs Catalog, 1996, 1-23.

(56) References Cited

OTHER PUBLICATIONS

Nishimasu et al., "Crystal Structure of Cas9 in Complex with Guide RNA and Target DNA," Cell, vol. 156, Feb. 27, 2014, 935-949.
O'Reilly, D. et al., "Extensive CRISPR RNA modification reveals chemical compatibility and structure-activity relationships for Cas9 biochemical activity," Nucleic Acids Res, 47(2):546-558, 2019.
Pattanayak et al., "High-throughput profiling of off-target DNA cleavage reveals RNA-programmed Cas9 nuclease specificity," Nat. Biotechnol, vol. 31, 2013, 839-843.
Peterson et al., "Genome-Wide Assessment of Efficiency and Specificity in CRISPR/Cas9 Mediated Multiple Site Targeting in *Arabidopsis*," PLOS ONE 11, e0162169 (Cas9 Specificity in *Arabidopsis*), Sep. 13, 2016, 1-11.
Piccirilli et al., "Enzymatic Incorporation of a New Base Pair into DNA and RNA Extends the Genetic Alphabet," Nature, vol. 343, Jan. 4, 1990, 33-37.
Polstein et al., "Genome-wide Specificity of DNA Binding, Gene Regulation, and Chromatin Remodeling by TALE- and CRISPR/Cas9-based Transcriptional Activators," Genome Research, vol. 25, 2015, 1158-1169.
Qiu et al., "Mutation Detection Using Surveyor™ Nuclease," Biotechniques, vol. 36, No. 4, Apr. 2004, 702-707.
Rahdar et al., "Synthetic CRISPR RNA-Cas9-guided genome editing in human cells," Proceedings of the National Academy of Sciences, vol. 112, No. 51, Nov. 16, 2015, pp. E7110-E7117.
Ran et al., "Double nicking by RNA-guided CRISPR Cas9 for enhanced genome editing specificity," Cell, vol. 154, No. 6, Sep. 12, 2013, 1380-1389.
Ran et al., "In Vivo Genome Editing Using *Staphylococcus aureus* Cas9," Nature, vol. 520, No. 7546, Apr. 9, 2015, 186-191.
Ran, F. et al., "Genome engineering using the CRISPR-Cas9 system," Nature Protocols, 8(11):2281-2308, 2013.
Rappaport, "Replication of the Base Pair6-Thioguanine/ 5-Methyl-2-pyrimidinone with the Large Klenow Fragment of *Escherichia coli* DNA Polymerase I," Biochemistry, vol. 32, No. 12, 1993, 3047-3057.
Ren et al., "Enhanced Specificity and Efficiency of the CRISPR/Cas9 System with Optimized sgRNA Parameters in *Drosophila*," Cell Rep, vol. 9, No. 3, Nov. 6, 2014, 1151-1162.
Rgenome.net, "Cas-OFFinder," CRISPR RGEN Tools, http://www.rgenome.net/Cas-OFFinder, Apr. 18, 2017, 4 pages.
Ryan, D. et al., "Improving CRISPR-Cas specificity with chemical modifications in single-guide RNAs," Nucleic Acids Res., 46(2):792-803, 2018.
Ryan, D. et al., U.S. Appl. No. 62/087,211, filed Dec. 3, 2014.
Ryan, D. et al., U.S. Appl. No. 62/146,189, filed Apr. 10, 2015.
Ryan, D. et al., U.S. Appl. No. 62/256,095, filed Nov. 16, 2015.
Sander, J. and J. Joung, "CRISPR-Cas systems for genome editing, regulating and targeting," Nat. Biotechnol., 32(4):347-355, 2014.
Sanghvi, Y., "A Status Update of Modified Oligonucleotides for Chemotherapeutics Applications," Curr. Protoc. Nucleic Acid Chem., 46:4.1.1-4.1.22, 2011.
Schechner et al., "CRISPR Display: A Modular Method for Locus-specific Targeting of Long Noncoding RNAs and Synthetic RNA Devices in Vivo," Nat. Methods, vol. 12, No. 7, Jul. 2015, 664-670.
Schneider et al., "Information Content of Binding Sites on Nucleotide Sequences," J. Mol. Biol., vol. 188, 1986, 415-431.
Semenova et al., "Interference by Clustered Regularly Interspaced Short Palindromic Repeat (CRISPR) RNA is Governed by a Seed Sequence," Proc. Natl. Acad. Sci, vol. 108, No. 25, Jun. 21, 2011, 10098-10103.
Sharma, V. et al., "Antisense oligonucleotides: modifications and clinical trials," Med. Chem. Commun., 5:1454-1471, 2014.
Shen et al., "Efficient Genome Modification by CRISPR-Cas9 Nickase with Minimal off-target Effects," Nature Methods, vol. 11, No. 4, Apr. 2014, 399-402.
Singh et al., "Cas9-chromatin Binding Information Enables More Accurate CRISPR off-target Prediction," Nucleic Acids Research, vol. 43, No. 18, 2015, 1-8.

Singh et al., "Real-Time Observation of DNA Recognition and Rejection by the RNA-Guided Endonuclease Cas9," Nature Communications, vol. 7, No. 12778, 2016, 1-8.
Slaymaker et al., "Rationally Engineered Cas9 Nucleases with Improved Specificity," Science vol. 351, Dec. 1, 2015, 84-88.
Smith et al., "Whole-Genome Sequencing Analysis Reveals High Specificity of CRISPR/Cas9 and TALEN-Based Genome Editing in Human iPSCs," Cell Stem Cell, vol. 15, No. 1, Jul. 3, 2014, 12-13.
Soutschek, J. et al., "Therapeutic silencing of an endogenous gene by systemic administration of modified siRNAs," Nature, 432:173-178, 2004.
Szczpek et al., "Structure-based Redesign of the Dimerization Interface Reduces the Toxicity of Zinc-finger Nucleases," Nature Biotechnology, vol. 25, No. 7, Jul. 2007, 786-793.
Thomas Jefferson University, "Off-Spotter," https://cm.jefferson.edu/Off-Spotter, 2017, 1 page.
Threlfall et al., "Synthesis and Biological Activity of Phosphonoacetate- and Thiophosphonoacetate-Modified 2'-O-Methyl Oligoriboucleotides," Organic & Biomolecular Chemistry, vol. 10, 2012, 746-754.
Tietze et al., "Squaric Acid Diethyl Ester: A New Coupling Reagent for the Formation of Drug Biopolymer Conjugates. Synthesis of Squaric Acid Ester Amides and Diamides," Chem. Ber., vol. 124, 1991, 1215-1221.
Tsai et al., "Defining and Improving the Genome-wide Specificities of CRISPR-Cas9 Nucleases," Nat. Rev. Genetics, vol. 17, May 2016, 300-312.
Tsai et al., "Dimeric CRISPR RNA-Guided FokI Nucleases for Highly Specific Genome Editing," Nat. Biotechnol, vol. 32, No. 6, Jun. 2014, 569-576.
Tsai et al., "GUIDE-seq Enables Genome-wide Profiling of off-target Cleavage by CRISPR-Cas Nucleases," Nature Biotechnology, vol. 33, No. 2, Feb. 2015, 187-197.
Tycko et al., "Methods for Optimizing CRISPR-Cas9 Genome Editing Specificity," Molecular Cell, vol. 63, Aug. 4, 2016, 355-370.
Wang et al., "Unbiased Detection of off-target Cleavage by CRISPR-Cas9 and TALENs using Integrase-defective Entiviral Vectors," Nature Biotechnology, vol. 33, No. 2, Feb. 2015, 175-178.
Wang, H. et al., "Antitumor activity and pharmacokinetics of a mixed-backbone antisense oligonucleotide targeted to the RI-α subunit of protein kinase A after oral administration," PNAS, 96(24):13989-13994, 1999.
Wu et al., "Genome-wide Binding of the CRISPR Endonuclease Cas9 in Mammalian Cells," Nature Biotechnology, vol. 32, No. 7, Jul. 2014, 670-676.
Wu et al., "Target Specificity of the CRISPR-Cas9 System," Quantitative Biology, vol. 2, No. 2, Jun. 2014, 1-19.
Wyvekens et al., "Dimeric CRISPR RNA-Guided FokI-dCas9 Nucleases Directed by Truncated gRNAs for Highly Specific Genome Editing," Human Gene Therapy, vol. 26, No. 7, 2015, 425-431.
Yamada et al., "Synthesis and Biochemical Evaluation of Phosphonoformate Oligodeoxyribonucleotides," J. Am. Chem. Soc., vol. 128, No. 15, 2006, 5251-5261.
Yang et al., "Artificially Expanded Genetic Information System: A New Base Pair With an Alternative Hydrogen Bonding Pattern," Nucleic Acids Research, vol. 34, No. 21, 2006, 6095-6101.
Yang et al., "Targeted and Genome-Wide Sequencing Reveal Single Nucleotide Variations Impacting Specificity of Cas9 in Human Stem Cells," Nature Communications, vol. 5, No. 5507, 2014, 1-6.
Yoo, B. et al., "2'-O-methyl-modified phosphorothioate antisense oligonucleotides have reduced non-specific effects in vitro," Nucleic Acids Research, 32(6): 2008-2016, 2004.
Yu, D. et al., "Single-Stranded RNAs Use RNAi to Potently and Allele-Selectively Inhibit Mutant Huntingtin Expression," Cell, 150:895-908, 2012.
Zetsche et al., "Cpf1 is a Single RNA-Guided Endonuclease of a Class 2 CRISPR-Cas System," Cell, vol. 163, No. 3, Oct. 22, 2015, 759-771.
Zhang et al., "Evolution of Functional Six-Nucleotide DNA," J. Am. Chem. Soc., vol. 137, No. 21, 2015, 6734-6737.
Zheng et al., "Profiling Single-guide RNA Specificity Reveals a Mismatch Sensitive Core Sequence," Scientific Reports, vol. 7, No. 40638, 2017, 1-8.

(56) References Cited

OTHER PUBLICATIONS

Zischewski et al., "Detection of on-target and off-target Mutations Generated by CRISPR/Cas9 and Other Sequence-specific Nucleases," Biotechnology Advances, vol. 35, 2017, 95-104.

Davis, S. et al., "Improved targeting of miRNA with antisense oligonucleotides," Nucleic Acids Research, 34(8):2294-2304, 2006.

Genscript, "GenCRISPR Synthetic sgRNA," webpage printout of <https://www.genscript.com/crispr-synthetic-sgrna.html#FAQs>, 2022, 8 pages.

GlobeNewswire, "Synthego Announces Modified Synthetic sgRNA—Critical for Editing Primary and Stem Cells, and Other Challenging Cell Types," webpage printout of <https://www.globenewswire.com/news-release/2017/03/21/1228773/0/en/Synthego-Announces-Modified-Synthetic-sgRNA-Critical-for-Editing-Primary-and-Stem-Cells-and-other-Challenging-Cell-Types.html>, Mar. 21, 2017, 2 pages.

Integrated DNA Technologies, Inc., "Custom CRISPR gRNA ordering," webpage printout of <https://eu.idtdna.com/pages/products/crispr-genome-editing/custom-guide-rna>, 2022, 2 pages.

News Medical, "Synthetic sgRNA for CRISPR genome editing," webpage printout of <https://www.news-medical.net/news/20161208/Synthetic-sgRNA-for-CRISPR-genome-editing.aspx>, Dec. 8, 2016, 6 pages.

Sampson, J., Declaration of Jeffrey R. Sampson in support of patent owner Agilent Technologies, Inc.'s response in IPR2022-00402 concerning U.S. Pat. No. 10,337,001 (*Synthego Corporation* v. *Agilent Technologies, Inc.*), Sep. 19, 2022, 7 pages.

Synthego, "Inspiring New Therapies in Biomedicine: CRISPR Editing in Primary Cells," webpage printout of <https://www.synthego.com/crispr-primary-cells?utm_campaign=Fast-tr>, Sep. 28, 2022, 10 pages.

Synthego, "CRISPRevolution sgRNA EZ kit," webpage printout of <https://orders.synthego.com/products/crisprevolution-sgrna-ez-kit-13/#/tubes?mod_code=1>, 2022, 2 pages.

Watts, J. et al., "Chemically modified siRNA: tools and applications," Drug Discovery Today, 13(19/20):842-855, Oct. 2008.

U.S. Appl. No. 18/074,781, filed Dec. 5, 2022.

U.S. Appl. No. 18/332,464, filed Jun. 9, 2023.

B = Adenine, Guanine, Cytosine, Uracil

|  sgRNA (µg) \ Cas9 (µg) | 1 | 5 | 10 | 15 |
|---|---|---|---|---|
| 1 | 70 | 86 | 86 | 85 |
| 2.5 | 81 | 86 | 82 | 89 |
| 5 | 84 | 85 | 87 | 88 |
| 10 | 83 | 88 | 89 | 90 |
| 20 | 86 | 89 | 89 | 90 |

FIG. 6

| | T cells | | CD34+ HSPCs | |
|---|---|---|---|---|
| Total cloned PCR fragments analyzed | 181 | 186 | 222 | 216 |
| % allele modification ±SEM | 73.9 (±2.8) | 93.1 (±1.1) | 37.8 (±6.5) | 43.0 (±4.3) |
| % WT alleles ±SEM | 26.1 (±2.8) | 6.9 (±1.1) | 62.2 (±6.5) | 57.0 (±4.3) |
| % alleles with deletion between the cut sites ±SEM | 53.4 (±4.2) | 69.7 (±2.1) | 21.1 (±1.8) | 23.1 (±3.1) |
| % alleles with inverted sequence between the cut sites ±SEM | 5.3 (±2.2) | 9.6 (±2.0) | 5.9 (±2.6) | 6.9 (±3.1) |
| % in/del at both sites ±SEM | 12.7 (±2.4) | 12.6 (±1.6) | 3.6 (±1.2) | 7.9 (±1.9) |
| % in/del at right site only ±SEM | 2.4 (±1.7) | 1.1 (±0.8) | 3.6 (±0.9) | 2.3 (±1.2) |
| % in/del at left site only ±SEM | 0 | 0 | 3.6 (±0.5) | 2.8 (±0.8) |

COMPOSITIONS COMPRISING CHEMICALLY MODIFIED GUIDE RNAS FOR CRISPR/CAS-MEDIATED EDITING OF HBB

CROSS-REFERENCE TO RELATED APPLICATIONS

The present application is a continuation of U.S. patent application Ser. No. 15/724,073 filed Oct. 3, 2017, now U.S. Pat. No. 11,306,309 B2, which is a continuation of PCT/US2016/026028 filed Apr. 5, 2016, which claims priority to U.S. Provisional Application Nos. 62/143,729 filed Apr. 6, 2015 and 10 62/160,545 filed May 12, 2015, the full disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support under contracts EY018244 and A1097320 awarded by the National Institutes of Health. The Government has certain rights in this invention.

SEQUENCE LISTING

The present application is being filed along with a Sequence Listing in electronic format. The Sequence Listing file, entitled 2022-03-14_SEQLST.txt, was created on Mar. 8, 2022, and is 54,808 bytes in size. The information in electronic format of the Sequence Listing is incorporated herein by reference in its entirety.

BACKGROUND OF THE INVENTION

Genome editing with engineered nucleases is a breakthrough technology for modifying essentially any genomic sequence of interest (Porteus, M. H. & Carroll, D., *Nature Biotechnology* 23, 967-973 (2005)). This technology exploits engineered nucleases to generate site-specific double-strand breaks (DSBs) followed by resolution of DSBs by endogenous cellular repair mechanisms. The outcome can be either mutation of a specific site through mutagenic nonhomologous end-joining (NHEJ), creating insertions or deletions (in/dels) at the site of the break, or precise change of a genomic sequence through homologous recombination (HR) using an exogenously introduced donor template (Hendel et al., *Trends in Biotechnology* 33, 132-140 (2015). A recent major addition to this platform is the clustered regularly interspaced palindromic repeat (CRISPR)/Cas system consisting of an RNA-guided nuclease (Cas) and a short guide RNA (sgRNA) Jinek, M. et al., *Science* 337, 816-821 (2012), Mali, P. et al., *Science* 339, 823-826 (2013), Cong, L. et al., *Science* 339, 819-823 (2013), Hsu et al., *Cell* 157, 1262-1278 (2014)). The guide RNA is composed of two RNAs termed CRISPR RNA (crRNA) and trans-activating crRNA (tracrRNA), which are typically fused in a chimeric single guide RNA (sgRNA).

sgRNAs for genome editing can consist of 100 nucleotides (nt) of which 20 nt at the 5' end hybridize to a target DNA sequence by means of Watson-Crick base pairing and guide the Cas endonuclease to cleave the target genomic DNA.

The CRISPR/Cas system has also been adapted for sequence-specific control of gene expression, e.g., inhibition or activation of gene expression. Using particular Cas9 polypeptide variants that lack endonuclease activity, target genes can be repressed or activated (Qi et al., *Cell*, 2013, 152(5):1173-7783, Perez-Pinera et al., *Nat Methods*, 2013, 10(10):973-976, Maeder et al., *Nat Methods*, 2013, 10(10): 977-979, Gilbert et al., *Cell*, 2014, 159:647-661, O'Connell et al., *Nature*, 2014, 516:263-266).

Unfortunately, genome editing and modulating gene expression using the CRISPR/Cas system remain inefficient, especially in primary cells. As such, there remains a need in the art for improved compositions and methods based on the CRISPR/Cas system that can be used for gene regulation, e.g., genome editing, inhibiting gene expression, and activating gene expression. The present invention satisfies this need and provides additional advantages as well.

BRIEF SUMMARY OF THE INVENTION

The present invention provides methods for inducing (e.g., initiating, modulating, enhancing, etc.) gene regulation of a target nucleic acid in a cell. The invention includes using modified single guide RNAs (sgRNAs) that enhance genome editing and/or inhibition or activation of gene expression of a target nucleic acid in a primary cell (e.g., cultured in vitro for use in ex vivo therapy) or in a cell in a subject such as a human (e.g., for use in in vivo therapy). The present invention also provides methods for preventing or treating a disease in a subject by enhancing precise genome editing to correct a mutation in a target gene associated with the disease. The present invention can be used with any cell type and at any gene locus that is amenable to nuclease-mediated genome editing technology.

In a first aspect, the present invention provides a method for inducing gene regulation of a target nucleic acid in a primary cell, the method comprising:
  introducing into the primary cell:
    (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/ or the second nucleotide sequence are modified nucleotides; and
    (b) a Cas polypeptide, an mRNA encoding a Cas polypeptide, and/or a recombinant expression vector comprising a nucleotide sequence encoding a Cas polypeptide,
  wherein the modified sgRNA guides the Cas polypeptide to the target nucleic acid, and
  wherein the modified sgRNA induces gene regulation of the target nucleic acid with an enhanced activity relative to a corresponding unmodified sgRNA.

In a related aspect, the present invention provides a method for enhancing genome editing of a target DNA in a primary cell, the method comprising:
  introducing into the primary cell:
    (a) a modified single guide RNA (sgRNA) comprising a first nucleotide sequence that is complementary to the target DNA and a second nucleotide sequence that interacts with a CRISPR-associated protein (Cas) polypeptide, wherein one or more of the nucleotides in the first nucleotide sequence and/or the second nucleotide sequence are modified nucleotides; and (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target DNA, and wherein the modified sgRNA enhances genome editing of the target DNA (e.g., via increased stability of the modified sgRNA and/or increased specificity of the modified sgRNA for the target DNA) relative to a corresponding unmodified sgRNA.

In a second aspect, the present invention provides a method for preventing or treating a genetic disease in a subject, the method comprising:

administering to the subject a modified single guide RNA (sgRNA) in a sufficient amount to correct a mutation in a target gene associated with the genetic disease, wherein the modified sgRNA comprises a first nucleotide sequence that is complementary to the target gene and a second nucleotide sequence that interacts with a CRISPR-associated protein (Cas) polypeptide, and wherein one or more of the nucleotides in the first nucleotide sequence and/or the second nucleotide sequence are modified nucleotides.

Other objects, features, and advantages of the present invention will be apparent to one of skill in the art from the following detailed description and figures.

BRIEF DESCRIPTION OF THE DRAWINGS

FIG. 1A shows the sequence and schematic of the secondary structure of the IL2RG sgRNA loaded into Cas9 and bound to its genomic target site. Nucleotides with chemical modifications are marked with white flags. FIG. 1B depicts structures of chemical modifications incorporated during chemical synthesis of sgRNAs (Table 1 for sequences). When present, chemical modifications comprising: 2'-O-methyl (M), 2'-O-methyl, 3'phosphorothioate (MS) or 2'-O-methyl, 3'thioPACE (MSP) (shown in grey) were incorporated at three terminal nucleotides at both 5' and 3' ends. FIG. 1C shows gene disruption by mutagenic NHEJ as measured by deep sequencing of PCR amplicons. FIG. 1D shows gene addition by HR at the three loci IL2RG, HBB, and CCR5 in K562 cells induced by Cas9 in combination with synthetic sgRNAs. The synthetic sgRNAs were delivered at 1 (light shade) or 20 μg (dark shade) per 1 million cells. Cas9 was expressed from a plasmid (2 μg) and for HR experiments 5 μg of GFP-encoding donor plasmid was included. As a positive control, 2 μg of sgRNA plasmid encoding both the sgRNA and the Cas9 protein was used (gray bars). Bars represent average values +SEM, n=3. FIG. 1E shows specificity of targeted cleavage mediated by synthetic sgRNAs as performed in FIG. 1C for 20 μg of sgRNA. In/del frequencies were measured by deep sequencing of PCR amplicons of the targeted genomic loci and three bioinformatically predicted off-target loci for each gene. Bars represent average values +SEM, n=3. FIG. 1F shows the staggered delivery of 15 μg Cas9 mRNA and 10 μg IL2RG synthetic sgRNAs into 1 million K562 cells using electroporation. Bars represent average in/del frequencies +SEM, n=3 as measured by TIDE analysis of PCR amplicons spanning the sgRNA target sites, using a mock-treated sample as reference control. In FIG. 1G, Cas9 protein was pre-complexed with a 2.5 molar excess of the indicated synthetic IL2RG sgRNAs and nucleofected into 1 million K562 cells at the indicated amounts. In/del frequencies were measured by TIDE analysis as above and bars represent average in/del frequencies +SEM, n=3.

In FIG. 2B, stimulated T cells were nucleofected as above, but with 15 Cas9 protein pre-complexed with a 2.5 molar excess of the indicated synthetic CCR5 sgRNAs. In/del frequencies were measure by TIDE analysis as above. Bars represent average in/del frequencies for three different donors +SEM, n=6. In FIG. 2C, 500,000 mobilized human peripheral blood CD34+ HSPCs were nucleofected with 10 μg of the indicated synthetic sgRNAs targeting IL2RG or HBB and either 15 μg Cas9 mRNA or 1 μg Cas9 plasmid. 1 μg of sgRNA plasmid encoding both the sgRNA and Cas9 protein was included for comparison. Bars represent average in/del frequencies +SEM, n=3 as measured by T7 endonuclease cleavage assay. In FIG. 2D, 1 million stimulated T cells or mobilized human peripheral blood CD34+ HSPCs were nucleofected with 15 μg Cas9 mRNA and 10 μg of the indicated synthetic CCR5 sgRNAs. When used in combination the amount of each sgRNA was 5 μg. In/del frequencies for samples with single sgRNAs were measured by TIDE analysis as above and in/del frequencies for samples with two sgRNAs were measured by sequencing of cloned PCR products (see, FIGS. 18A-B). Bars represent average in/del frequencies +SEM, n=3.

FIG. 6 shows the titration of the MSP sgRNA targeting IL2RG and Cas9 mRNA in K562 cells. Measured in/del frequencies are averages from three replicates and values are indicated in a heat map. SEM of replicates (n=3) is not indicated for clarity, but are all less than 4% of measured indicated values. In/del frequencies were measured by TIDE analysis of PCR amplicons spanning the sgRNA target sites and using a mock-treated sample as reference control.

DETAILED DESCRIPTION OF THE INVENTION

I. Introduction

Figure 1A:
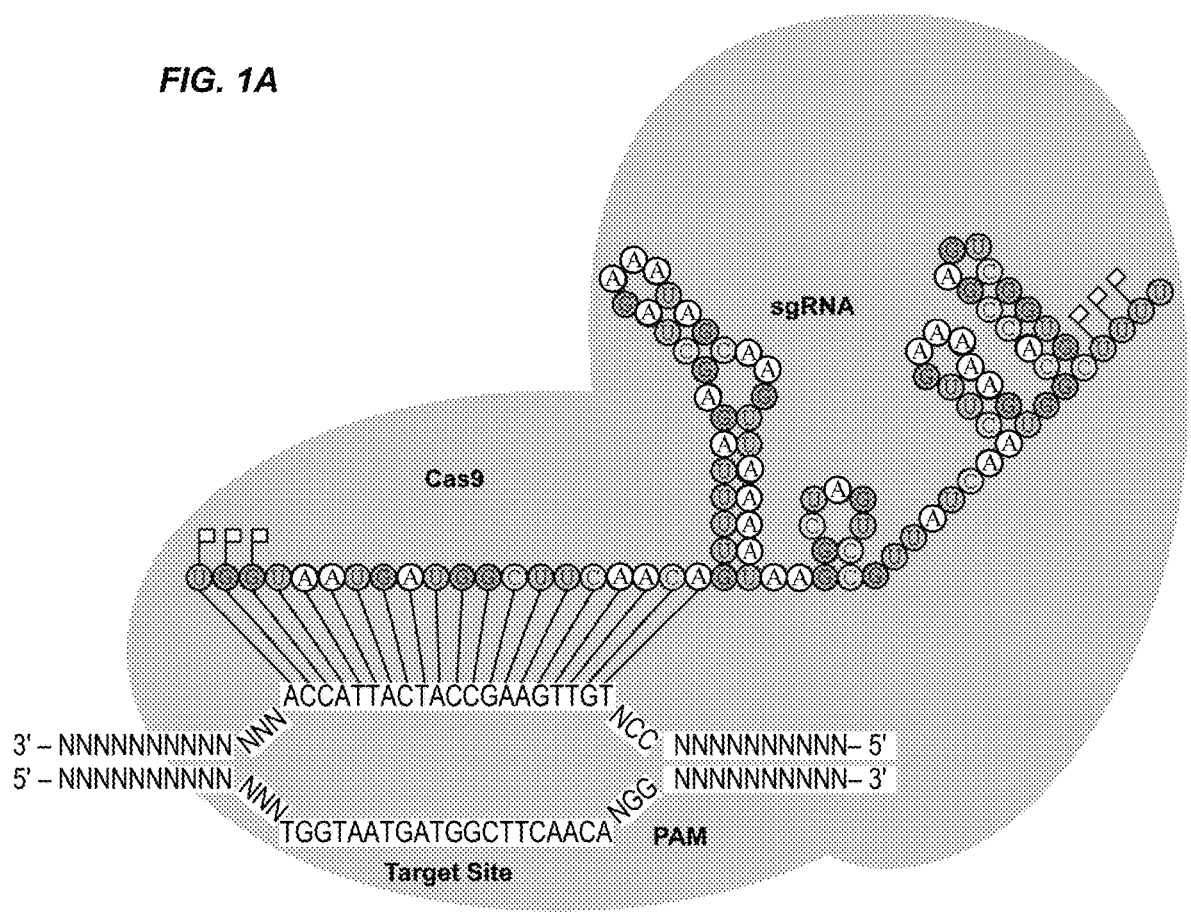
FIGS. 1A-G show that synthesized and chemically modified sgRNAs facilitate high levels of DNA cleavage in vitro and high frequencies of in/dels in a human cell line (K562).

Provided herein are methods for CRISPR/Cas-based genome editing and/or modulation of gene expression in an in vitro cell (e.g., a primary cell for use in ex vivo therapy) or an in vivo cell (e.g., a cell in an organ or tissue of a subject such as a human). In particular, the methods provided herein utilize chemically modified single guide RNAs (sgRNAs) having enhanced activity during gene regulation (e.g., genome editing, inhibition of gene expression, and activation of gene expression) compared to corresponding unmodified sgRNAs. In certain aspects, the present invention provides methods for gene regulation of a target nucleic acid in a cell by introducing a chemically modified sgRNA that hybridizes to the target nucleic acid together with either a Cas nuclease (e.g., Cas9 polypeptide) or a variant or fragment thereof, an mRNA encoding a Cas nuclease (e.g., Cas9 polypeptide) or a variant or fragment thereof, or a recombinant expression vector comprising a nucleotide sequence encoding a Cas nuclease (e.g., Cas9 polypeptide) or a variant or fragment thereof. In certain other aspects, the present invention provides methods for preventing or treating a genetic disease in a subject by administering a sufficient amount of the chemically modified sgRNA to correct a genetic mutation associated with the disease.

II. General

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, *Molecular Cloning: A Laboratory Manual*, 2nd edition (1989), *Current Protocols in Molecular Biology* (F. M. Ausubel, et al. eds., (1987)), the series *Methods in Enzymology* (Academic Press, Inc.): PCR 2: A Practical Approach (M. J. MacPherson, B. D. Hames and G. R. Taylor eds. (1995)), Harlow and Lane, eds. (1988) Antibodies, *A Laboratory Manual*, and *Animal Cell Culture* (R. I. Freshney, ed. (1987)).

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

III. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "primary cell" refers to a cell isolated directly from a multicellular organism. Primary cells typically have undergone very few population doublings and are therefore more representative of the main functional component of the tissue from which they are derived in comparison to continuous (tumor or artificially immortalized) cell lines. In some cases, primary cells are cells that have been isolated and then used immediately. In other cases, primary cells cannot divide indefinitely and thus cannot be cultured for long periods of time in vitro.

The term "genome editing" refers to a type of genetic engineering in which DNA is inserted, replaced, or removed from a target DNA, e.g., the genome of a cell, using one or more nucleases and/or nickases. The nucleases create specific double-strand breaks (DSBs) at desired locations in the genome, and harness the cell's endogenous mechanisms to repair the induced break by homology-directed repair (HDR) (e.g., homologous recombination) or by nonhomologous end joining (NHEJ). The nickases create specific single-strand breaks at desired locations in the genome. In one non-limiting example, two nickases can be used to create two single-strand breaks on opposite strands of a target DNA, thereby generating a blunt or a sticky end. Any suitable nuclease can be introduced into a cell to induce genome editing of a target DNA sequence including, but not limited to, CRISPR-associated protein (Cas) nucleases, zinc finger nucleases (ZFNs), transcription activator-like effector nucleases (TALENs), meganucleases, other endo- or exonucleases, variants thereof, fragments thereof, and combinations thereof. In particular embodiments, nuclease-mediated genome editing of a target DNA sequence can be "induced" or "modulated" (e.g., enhanced) using the modified single guide RNAs (sgRNAs) described herein in combination with Cas nucleases (e.g., Cas9 polypeptides or Cas9 mRNA), e.g., to improve the efficiency of precise genome editing via homology-directed repair (HDR).

The term "homology-directed repair" or "HDR" refers to a mechanism in cells to accurately and precisely repair double-strand DNA breaks using a homologous template to guide repair. The most common form of HDR is homologous recombination (HR), a type of genetic recombination in which nucleotide sequences are exchanged between two similar or identical molecules of DNA.

The term "nonhomologous end joining" or "NHEJ" refers to a pathway that repairs double-strand DNA breaks in which the break ends are directly ligated without the need for a homologous template.

The term "nucleic acid," "nucleotide," or "polynucleotide" refers to deoxyribonucleic acids (DNA), ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated.

Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate.

The term "gene" or "nucleotide sequence encoding a polypeptide" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "variant" refers to a form of an organism, strain, gene, polynucleotide, polypeptide, or characteristic that deviates from what occurs in nature.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "stringent conditions" for hybridization refers to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

The term "hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these.

A "recombinant expression vector" is a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector.

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide).

The term "single nucleotide polymorphism" or "SNP" refers to a change of a single nucleotide with a polynucleotide, including within an allele. This can include the replacement of one nucleotide by another, as well as deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position.

The terms "culture," "culturing," "grow," "growing," "maintain," "maintaining," "expand," "expanding," etc., when referring to cell culture itself or the process of culturing, can be used interchangeably to mean that a cell (e.g., primary cell) is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce. Cells are typically cultured in media, which can be changed during the course of the culture.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "sufficient amount" refers to the amount of an agent (e.g., Cas nuclease, modified single guide RNA, etc.) that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other agents, timing of administration, and the physical delivery system in which it is carried.

The term "pharmaceutically acceptable carrier" refers to a substance that aids the administration of an agent (e.g., Cas nuclease, modified single guide RNA, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention.

The term "increasing stability," with respect to components of the CRISPR system, refers to modifications that stabilize the structure of any molecular component of the CRISPR system. The term includes modifications that decrease, inhibit, diminish, or reduce the degradation of any molecular component of the CRISPR system.

The term "increasing specificity," with respect to components of the CRISPR system, refers to modifications that increase the specific activity (e.g., the on-target activity) of any molecular component of the CRISPR system. The term includes modifications that decrease, inhibit, diminish, or reduce the non-specific activity (e.g., the off-target activity) of any molecular component of the CRISPR system.

The term "decreasing toxicity," with respect to components of the CRISPR system, refers to modifications that decrease, inhibit, diminish, or reduce the toxic effect of any molecular component of the CRISPR system on a cell, organism, subject, and the like.

The term "enhanced activity," with respect to components of the CRISPR system and in the context of gene regulation, refers to an increase or improvement in the efficiency and/or the frequency of inducing, modulating, regulating, or controlling genome editing and/or gene expression.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

IV. Description of the Embodiments

The present invention provides methods for inducing gene regulation of a target nucleic acid in a cell. The invention includes using modified single guide RNAs (sgRNAs) that enhance genome editing and/or inhibition or activation of gene expression of a target nucleic acid in a primary cell (e.g., cultured in vitro for use in ex vivo therapy) or in a cell in a subject such as a human (e.g., for use in in vivo therapy). The present invention also provides methods for preventing or treating a disease in a subject by enhancing precise genome editing to correct a mutation in a target gene associated with the disease. The present invention can be used with any cell type and at any gene locus that is amenable to nuclease-mediated genome editing technology.

In a first aspect, the present invention provides a method for inducing (e.g., initiating, modulating, enhancing, etc.) gene regulation of a target nucleic acid in a primary cell, the method comprising:
    introducing into the primary cell:
        (a) a modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are modified nucleotides; and (b) a Cas polypeptide, an mRNA encoding a Cas polypeptide, and/or a recombinant expression vector comprising a nucleotide sequence encoding a Cas polypeptide, wherein the modified sgRNA guides the Cas polypeptide to the target nucleic acid, and wherein the modified sgRNA induces gene regulation of the target nucleic acid with an enhanced activity relative to a corresponding unmodified sgRNA.

In some embodiments, the enhanced activity comprises increased stability of the modified sgRNA and/or increased specificity of the modified sgRNA for the target nucleic acid.

In some embodiments, the target nucleic acid comprises a target DNA or a target RNA. Gene regulation of a target nucleic acid encompasses any mechanism used by cells to increase or decrease the production of a specific gene product (e.g., protein or RNA) by the target nucleic acid and includes genome editing of the target nucleic acid or modulation (e.g., inhibition or activation) of gene expression of the target nucleic acid. In some instances, the gene regulation comprises genome editing of the target DNA. The genome editing can be homologous-directed repair (HDR) or nonhomologous end joining (NHEJ) of the target DNA. In other instances, the gene regulation comprises modulating (e.g., inhibiting or activating) gene expression of the target DNA or the target RNA using an endonuclease-deficient Cas polypeptide.

In some embodiments, the method further comprises introducing a recombinant donor repair template into the primary cell. In certain instances, the recombinant donor repair template comprises two nucleotide sequences comprising two non-overlapping, homologous portions of the target DNA, wherein the nucleotide sequences are located at the 5' and 3' ends of a nucleotide sequence corresponding to the target DNA to undergo genome editing. In other instances, the recombinant donor repair template comprises a synthetic single-stranded oligodeoxynucleotide (ssODN) template comprising a nucleotide sequence encoding a mutation to correct a single nucleotide polymorphism (SNP) and two nucleotide sequences comprising two non-overlapping, homologous portions of the target DNA, wherein the nucleotide sequences are located at the 5' and 3' ends of the nucleotide sequence encoding the mutation.

In some embodiments, the primary cell is isolated from a multicellular organism prior to introducing the modified sgRNA and the Cas polypeptide into the primary cell. The multicellular organism can be a plant, a multicellular protist, a multicellular fungus, or an animal such as a mammal (e.g., human). In certain instances, the primary cell is selected from the group consisting of a stem cell, an immune cell, and a combination thereof. Non-limiting examples of stem cells include hematopoietic stem and progenitor cells (HSPCs) such as CD34+ HSPCs, mesenchymal stem cells, neural stem cells, organ stem cells, and combinations thereof. Non-limiting examples of immune cells include T cells (e.g., CD3+ T cells, CD4+ T cells, CD8+ T cells, tumor infiltrating cells (TILs), memory T cells, memory stem T cells, effector T cells), natural killer cells, monocytes, peripheral blood mononuclear cells (PBMCs), peripheral blood lymphocytes (PBLs), and combinations thereof. In other embodiments, the primary cell or a progeny thereof (e.g., a cell derived from the primary cell) is returned (e.g., administered via any acceptable delivery system and delivery route) to the multicellular organism (e.g., human) after introducing the modified sgRNA and the Cas polypeptide into the primary cell.

In some embodiments, the primary cell comprises a population of primary cells. In some instances, the modified sgRNA induces gene regulation of the target nucleic acid in at least about 5%, 10%, 15%, 20%, 25%, 30%, 35%, 40%, 45%, 50%, 55%, 60%, 65%, 70%, 75%, 80%, 85%, 90%, or 95% of the population of primary cells. In other instances, the population of primary cells comprises at least about 10, $10^2$, $10^3$, $10^4$, $10^5$, $10^6$, $10^7$, $10^8$, or $10^9$ primary cells. In certain instances, the gene regulation comprises genome editing (e.g., HDR or NHEJ) of the target DNA in the population of primary cells. In certain other instances, the gene regulation comprises modulating (e.g., inhibiting or activating) gene expression of the target DNA or the target RNA in the population of primary cells using an endonuclease-deficient Cas polypeptide. As a non-limiting example, the modified sgRNA can induce HDR (e.g., in/del frequencies) in at least about 30%, 35%, 40%, 45%, 50%, 55%, or 60% of a population of primary T cells after introducing a modified sgRNA into the primary T cells with a Cas polypeptide (e.g., as a ribonucleoprotein (RNP) complex) or an mRNA encoding a Cas polypeptide. As another non-limiting example, the modified sgRNA can induce HDR (e.g., in/del frequencies) in at least about 10%, 15%, 20%, 25%, 30%, 35%, 40%, 45%, 50%, 55%, or 60% of a population of primary hematopoietic stem and progenitor cells (HSPCs) after introducing a modified sgRNA into the primary HSPCs with a Cas polypeptide (e.g., as an RNP complex) or an mRNA encoding a Cas polypeptide.

In some embodiments, the one or more modified nucleotides in the first nucleotide sequence and/or the second nucleotide sequence of the modified sgRNA comprise a modification in the ribose group, phosphate group, nucleobase, or combinations thereof. The modification in the ribose group can be a modification at the 2' position of the ribose group. In some instances, the modification at the 2' position of the ribose group is selected from the group consisting of 2'-O-methyl, 2'-fluoro, 2'-deoxy, and 2'-O-(2-methoxyethyl). The modification in the phosphate group can be a phosphorothioate modification.

In particular embodiments, the one or more modified nucleotides in the first nucleotide sequence and/or the second nucleotide sequence of the modified sgRNA comprise 2'-O-methyl (M) nucleotides, 2'-O-methyl 3'-phosphorothioate (MS) nucleotides, 2'-O-methyl 3'-thioPACE (MSP) nucleotides, or combinations thereof. In some cases, the modified sgRNA includes one or more MS nucleotides in the first nucleotide sequence and/or the second nucleotide sequence. In some cases, the modified sgRNA includes one or more MSP nucleotides in the first nucleotide sequence and/or the second nucleotide sequence. In some cases, the modified sgRNA includes one or more MS nucleotides and one or more MSP nucleotides in the first nucleotide sequence and/or the second nucleotide sequence. In some cases, the modified sgRNA does not include M nucleotides in the first nucleotide sequence and/or the second nucleotide sequence. In some cases, the modified sgRNA includes only MS nucleotides and/or MSP nucleotides as the modified nucleotides in the first nucleotide sequence and/or the second nucleotide sequence. In other cases, the modified sgRNA includes one or more MS nucleotides and/or one or more MSP nucleotides in the first nucleotide sequence and/or the second nucleotide sequence, and may further include one or more M nucleotides in the first nucleotide sequence and/or the second nucleotide sequence.

In some embodiments, the first nucleotide sequence of the modified sgRNA is about 20 nucleotides in length. In some instances, at least two, three, four, five, six, seven, eight, nine, ten, or more of the nucleotides in the first nucleotide sequence are modified nucleotides. In certain instances, about 2, 3, 4, 5, 6, 7, 8, 9, 10, 11, 12, 13, 14, 15, 16, 17, 18, 19, or 20 of the nucleotides in the first nucleotide sequence (e.g., a first nucleotide sequence of about 20 nucleotides in length) are modified nucleotides. In other instances, all of the nucleotides in the first nucleotide sequence (e.g., a first nucleotide sequence of about 20 nucleotides in length) are modified nucleotides. In some instances, the modified nucleotides are located at the 5'-end (e.g., the terminal nucleotide at the 5'-end) or near the 5'-end (e.g., within 1, 2, 3, 4, or 5 nucleotides of the terminal nucleotide at the 5'-end) of the first nucleotide sequence and/or at internal positions within the first nucleotide sequence. In other instances, from about 10% to about 30% of the nucleotides in the first nucleotide sequence are modified nucleotides.

In some embodiments, the second nucleotide sequence of the modified sgRNA is about 80 nucleotides in length. In some instances, at least two, three, four, five, six, seven, eight, nine, ten, or more of the nucleotides in the second nucleotide sequence are modified nucleotides. In certain instances, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 of the nucleotides in the second nucleotide sequence (e.g., a second nucleotide sequence of about 80 nucleotides in length) are modified nucleotides. In other instances, all of the nucleotides in the second nucleotide sequence (e.g., a second nucleotide sequence of about 80 nucleotides in length) are modified nucleotides. In some instances, the modified nucleotides are located at the 3'-end (e.g., the terminal nucleotide at the 3'-end) or near the 3'-end (e.g., within 1, 2, 3, 4, or 5 nucleotides of the 3'-end) of the second nucleotide sequence and/or at internal positions within the second nucleotide sequence. In other instances, from about 1% to about 10% of the nucleotides in the second nucleotide sequence are modified nucleotides.

In certain embodiments, the modified sgRNA comprises one, two, or three consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the first nucleotide sequence and one, two, or three consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the second nucleotide sequence.

In some instances, the modified sgRNA comprises one modified nucleotide at the 5'-end (e.g., the terminal nucleotide at the 5'-end) or near the 5'-end (e.g., within 1, 2, 3, 4, or 5 nucleotides of the terminal nucleotide at the 5'-end) of the first nucleotide sequence and one modified nucleotide at the 3'-end (e.g., the terminal nucleotide at the 3'-end) or near the 3'-end (e.g., within 1, 2, 3, 4, or 5 nucleotides of the 3'-end) of the second nucleotide sequence.

In other instances, the modified sgRNA comprises two consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the first nucleotide sequence and two consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the second nucleotide sequence.

In yet other instances, the modified sgRNA comprises three consecutive or non-consecutive modified nucleotides starting at the 5'-end (e.g., the terminal nucleotide at the 5'-end) or near the 5'-end (e.g., within 1, 2, 3, 4, or 5 nucleotides of the terminal nucleotide at the 5'-end) of the first nucleotide sequence and three consecutive or non-consecutive modified nucleotides starting at the 3'-end (e.g., the terminal nucleotide at the 3'-end) or near the 3'-end (e.g., within 1, 2, 3, 4, or 5 nucleotides of the 3'-end) of the second nucleotide sequence.

In particular embodiments, the modified sgRNA comprises three consecutive modified nucleotides at the 5'-end of the first nucleotide sequence and three consecutive modified nucleotides at the 3'-end of the second nucleotide sequence.

In some embodiments, the modified sgRNA is chemically synthesized. In other embodiments, the method for inducing gene regulation comprises multiplexed gene regulation (e.g., genome editing or modulating gene expression) of a single target nucleic acid sequence or different target nucleic acid sequences using a plurality of modified sgRNAs. In particular embodiments, the multiplexed gene regulation is more efficient and/or consistent relative to the use of corresponding unmodified sgRNAs. In certain instances, the plurality of modified sgRNAs comprises at least two, three, four, five, ten, fifteen, twenty, or more different modified sgRNAs, wherein each modified sgRNA is directed to a different target nucleic acid. In other instances, the plurality of modified sgRNAs comprises at least two, three, four, five, ten, fifteen, twenty, or more different modified sgRNAs, wherein each modified sgRNA is directed to the same target nucleic acid.

In certain embodiments, the Cas polypeptide is a Cas polypeptide variant or a Cas polypeptide fragment. In particular embodiments, the Cas polypeptide is a Cas9 polypeptide, a variant thereof, or a fragment thereof. In other embodiments, the step of introducing into the primary cell comprises electroporating (e.g., via nucleofection) the primary cell.

In a second aspect, the present invention provides a method for preventing or treating a genetic disease in a subject, the method comprising:

administering to the subject a modified single guide RNA (sgRNA) in a sufficient amount to correct a mutation in a target gene associated with the genetic disease, wherein the modified sgRNA comprises a first nucleotide sequence that is complementary to the target gene and a second nucleotide sequence that interacts with a CRISPR-associated protein (Cas) polypeptide, and wherein one or more of the nucleotides in the first nucleotide sequence and/or the second nucleotide sequence are modified nucleotides.

In some embodiments, the genetic disease is selected from the group consisting of X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disease or disorders, inflammation, immune-related diseases or disorders, metabolic diseases, liver diseases and disorders, kidney diseases and disorders, muscular/skeletal diseases and disorders, neurological and neuronal diseases and disorders, cardiovascular diseases and disorders, pulmonary diseases and disorders, ocular diseases and disorders, and viral infections (e.g., HIV infection).

In some embodiments, the method further comprises administering to the subject a Cas polypeptide, an mRNA encoding a Cas polypeptide, and/or a recombinant expression vector comprising a nucleotide sequence encoding a Cas polypeptide.

In some embodiments, the method further comprises administering to the subject a recombinant donor repair template. In certain instances, the recombinant donor repair template comprises two nucleotide sequences comprising two non-overlapping, homologous portions of the target gene, wherein the nucleotide sequences are located at the 5' and 3' ends of a nucleotide sequence corresponding to the target gene to undergo genome editing. In other instances, the recombinant donor repair template comprises a synthetic single-stranded oligodeoxynucleotide (ssODN) template comprising a nucleotide sequence encoding a mutation to correct a single nucleotide polymorphism (SNP) in the target gene, and two nucleotide sequences comprising two non-overlapping, homologous portions of the target gene, wherein the nucleotide sequences are located at the 5' and 3' ends of the nucleotide sequence encoding the mutation.

In certain embodiments, administering the modified sgRNA enhances the effect of the Cas polypeptide to correct the mutation in the target gene compared to administering the corresponding unmodified sgRNA. Non-limiting embodiments related to the modified sgRNA used in the method for preventing or treating a genetic disease in a subject are described above.

In some embodiments, the modified sgRNA, Cas polypeptide, and/or recombinant donor repair template is administered to the subject with a pharmaceutically acceptable carrier.

In some embodiments, the modified sgRNA, Cas polypeptide, and/or recombinant donor repair template is administered to the subject via a delivery system selected from the group consisting of a nanoparticle, a liposome, a micelle, a virosome, a nucleic acid complex, and a combination thereof. In certain instances, the nucleic acid complex comprises the modified sgRNA complexed with the Cas polypeptide.

In some embodiments, the modified sgRNA, Cas polypeptide, and/or recombinant donor repair template is administered to the subject via a delivery route selected from the group consisting of oral, intravenous, intraperitoneal, intramuscular, intradermal, subcutaneous, intra-arteriole, intraventricular, intracranial, intralesional, intrathecal, topical, transmucosal, intranasal, and a combination thereof.

It is contemplated that the chemically modified sgRNA described herein can be used with any CRISPR-associated technology, including, but not limited to, the CRISPRi for inhibition of gene expression, CRISPRa for activation of gene expression, CRISPR imaging tools for dynamic visualization of genomic loci, and CRISPR-mediated RNA recognition and cleavage. In some cases, the sgRNA can be used for imaging and/or delivery of small molecules or proteins into in vitro cells or in vivo cells. Accordingly, the sgRNAs may be used in research and therapeutic applications.

A. CRISPR/Cas System

The CRISPR/Cas system of genome modification includes a Cas nuclease (e.g., Cas9 nuclease) or a variant or fragment thereof, a DNA-targeting RNA (e.g., modified sgRNA) containing a guide sequence that targets the Cas nuclease to the target genomic DNA and a scaffold sequence that interacts with the Cas nuclease (e.g., tracrRNA), and optionally, a donor repair template. In some instances, a variant of a Cas nuclease such as a Cas9 mutant containing one or more of the following mutations: D10A, H840A, D839A, and H863A, or a Cas9 nickase can be used. In other instances, a fragment of a Cas nuclease or a variant thereof with desired properties (e.g., capable of generating single- or double-strand breaks and/or modulating gene expression) can be used. The donor repair template can include a nucleotide sequence encoding a reporter polypeptide such as a fluorescent protein or an antibiotic resistance marker, and homology arms that are homologous to the target DNA and flank the site of gene modification. Alternatively, the donor repair template can be a single-stranded oligodeoxynucleotide (ssODN).

1. Cas Nucleases and Variants Thereof

The CRISPR (Clustered Regularly Interspaced Short Palindromic Repeats)/Cas (CRISPR-associated protein) nuclease system is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide guide sequence contained within the crRNA transcript. The Cas (e.g., Cas9) nuclease requires both the crRNA and the tracrRNA for site-specific DNA recognition and cleavage. This system has now been engineered such that the crRNA and tracrRNA can be combined into one molecule (the "single guide RNA" or "sgRNA"), and the crRNA equivalent portion of the single guide RNA can be engineered to guide the Cas (e.g., Cas9) nuclease to target any desired sequence (see, e.g., Jinek et al. (2012) Science, 337:816-821; Jinek et al. (2013) eLife, 2:e00471; Segal (2013) eLife, 2:e00563). Thus, the CRISPR/Cas system can be engineered to create a double-strand break at a desired target in a genome of a cell, and harness the cell's endogenous mechanisms to repair the induced break by homology-directed repair (HDR) or non-homologous end-joining (NHEJ).

In some embodiments, the Cas nuclease has DNA cleavage activity. The Cas nuclease can direct cleavage of one or both strands at a location in a target DNA sequence. For example, the Cas nuclease can be a nickase having one or more inactivated catalytic domains that cleaves a single strand of a target DNA sequence.

Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, variants thereof, fragments thereof, mutants thereof, and derivatives thereof. There are three main types of Cas nucleases (type I, type II, and type III), and 10 subtypes including 5 type I, 3 type II, and 2 type III proteins (see, e.g., Hochstrasser and Doudna, Trends Biochem Sci, 2015:40(1): 58-66). Type II Cas nucleases include Cas1, Cas2, Csn2, and Cas9. These Cas nucleases are known to those skilled in the art. For example, the amino acid sequence of the Strepto-

*coccus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470. CRISPR-related endonucleases that are useful in the present invention are disclosed, e.g., in U.S. Application Publication Nos. 2014/0068797, 2014/0302563, and 2014/0356959.

Cas nucleases, e.g., Cas9 polypeptides, can be derived from a variety of bacterial species including, but not limited to, *Veillonella* atypical, *Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes,* and *Francisella novicida.*

"Cas9" refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor,* and *Campylobacter.* In some embodiments, the two catalytic domains are derived from different bacteria species.

Useful variants of the Cas9 nuclease can include a single inactive catalytic domain, such as a RuvC⁻ or HNH⁻ enzyme or a nickase. A Cas9 nickase has only one active functional domain and can cut only one strand of the target DNA, thereby creating a single-strand break or nick. In some embodiments, the mutant Cas9 nuclease having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A double-nicked induced double-strand break can be repaired by NHEJ or HDR (Ran et al., 2013, *Cell,* 154:1380-1389). This gene editing strategy favors HDR and decreases the frequency of indel mutations at off-target DNA sites. Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the target cell or target organism.

In some embodiments, the Cas nuclease can be a Cas9 polypeptide that contains two silencing mutations of the RuvC1 and HNH nuclease domains (D10A and H840A), which is referred to as dCas9 (Jinek et al., *Science,* 2012, 337:816-821; Qi et al., *Cell,* 152(5):1173-1183). In one embodiment, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983 or D986, as well as a mutation at H840 or N863. In some instances, the dCas9 enzyme contains a D10A or D10N mutation. Also, the dCas9 enzyme can include a H840A, H840Y, or H840N. In some embodiments, the dCas9 enzyme of the present invention comprises D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target DNA.

In certain embodiments, the dCas9 polypeptide is catalytically inactive such as defective in nuclease activity. In some instances, the dCas9 enzyme or a variant or fragment thereof can block transcription of a target sequence, and in some cases, block RNA polymerase. In other instances, the dCas9 enzyme or a variant or fragment thereof can activate transcription of a target sequence.

For genome editing methods, the Cas nuclease can be a Cas9 fusion protein such as a polypeptide comprising the catalytic domain of the type IIS restriction enzyme, FokI, linked to dCas9. The FokI-dCas9 fusion protein (fCas9) can use two guide RNAs to bind to a single strand of target DNA to generate a double-strand break.

For gene regulation (e.g., modulating transcription of target DNA), a nuclease-deficient Cas protein, such as but not limited to dCas9, can be used for transcriptional activation or transcriptional repression. Methods of inactivating gene expression using a nuclease-null Cas protein are described, for example, in Larson et al., *Nat. Protoc.,* 2013, 8(11):2180-2196.

In some embodiments, a nucleotide sequence encoding the Cas nuclease is present in a recombinant expression vector. In certain instances, the recombinant expression vector is a viral construct, e.g., a recombinant adeno-associated virus construct, a recombinant adenoviral construct, a recombinant lentiviral construct, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Useful expression vectors are known to those of skill in the art, and many are commercially available. The following vectors are provided by way of example for eukaryotic host cells: pXT1, pSG5, pSVK3, pBPV, pMSG, and pSVLSV40. However, any other vector may be used if it is compatible with the host cell. For example, useful expression vectors containing a nucleotide sequence encoding a Cas9 enzyme are commercially available from, e.g., Addgene, Life Technologies, Sigma-Aldrich, and Origene.

Depending on the target cell/expression system used, any of a number of transcription and translation control elements, including promoter, transcription enhancers, transcription terminators, and the like, may be used in the expression vector. Useful promoters can be derived from viruses, or any organism, e.g., prokaryotic or eukaryotic organisms. Suitable promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc.

The Cas nuclease and variants or fragments thereof can be introduced into a cell (e.g., an in vitro cell such as a primary cell for ex vivo therapy, or an in vivo cell such as in a patient) as a Cas polypeptide or a variant or fragment thereof, an mRNA encoding a Cas polypeptide or a variant or fragment thereof, or a recombinant expression vector comprising a nucleotide sequence encoding a Cas polypeptide or a variant or fragment thereof.

2. Modified Single Guide RNA (sgRNA)

The modified sgRNAs for use in the CRISPR/Cas system of genome modification typically include a guide sequence (e.g., crRNA) that is complementary to a target nucleic acid sequence and a scaffold sequence (e.g., tracrRNA) that interacts with a Cas nuclease (e.g., Cas9 polypeptide) or a variant or fragment thereof. The present inventors have discovered that modified sgRNAs containing one or more chemical modifications can increase the activity, stability, and specificity, and/or decrease the toxicity of the modified sgRNAs compared to corresponding unmodified sgRNAs when used for CRISPR-based gene regulation (e.g., genome editing or modulating gene expression) in primary cells (e.g., T cells or hematopoietic stem and progenitor cells). The advantages of the modified sgRNAs over the prior art include, but are not limited to, greater ease of delivery into target cells such as primary cells, as well as increased stability, increased duration of activity, and reduced toxicity in the target cells. In some cases, the modified sgRNAs as part of the CRISPR/Cas system provide higher frequencies of on-target gene regulation compared to other systems. In other cases, the modified sgRNAs provide improved activity and/or specificity compared to their unmodified sequence equivalents.

In certain instances, the modified sgRNA is complexed with a Cas nuclease (e.g., Cas9 polypeptide) or a variant or fragment thereof to form a ribonucleoprotein (RNP)-based delivery system for introduction into a cell (e.g., an in vitro cell such as a primary cell for ex vivo therapy, or an in vivo cell such as in a patient). In other instances, the modified sgRNA is introduced into a cell (e.g., an in vitro cell such as a primary cell for ex vivo therapy, or an in vivo cell such as in a patient) with an mRNA encoding a Cas nuclease (e.g., Cas9 polypeptide) or a variant or fragment thereof. In yet other instances, the modified sgRNA is introduced into a cell (e.g., an in vitro cell such as a primary cell for ex vivo therapy, or an in vivo cell such as in a patient) with a recombinant expression vector comprising a nucleotide sequence encoding a Cas nuclease (e.g., Cas9 polypeptide) or a variant or fragment thereof.

In some instances, a plurality of modified sgRNAs can be used for efficient multiplexed CRISPR-based gene regulation (e.g., genome editing or modulating gene expression) in target cells such as primary cells. The plurality of modified sgRNAs can include at least about 2, 3, 4, 5, 6, 7, 8, 9, 10, 15, 20, 25, 30, 35, 40, 45, 50, or more modified sgRNAs that hybridize to the same target nucleic acid sequence or to different target nucleic acid sequences. The plurality of modified sgRNAs can be introduced into a cell (e.g., an in vitro cell such as a primary cell for ex vivo therapy, or an in vivo cell such as in a patient) in a complex with a Cas nuclease (e.g., Cas9 polypeptide) or a variant or fragment thereof, or as a nucleotide sequence (e.g., mRNA or recombinant expression vector) encoding a Cas nuclease (e.g., Cas9 polypeptide) or a variant or fragment thereof.

The nucleic acid sequence of the modified sgRNA can be any polynucleotide sequence having sufficient complementarity with a target polynucleotide sequence (e.g., target DNA sequence) to hybridize with the target sequence and direct sequence-specific binding of a CRISPR complex to the target sequence. In some embodiments, the degree of complementarity between a guide sequence of the modified sgRNA and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some instances, a guide sequence is about 20 nucleotides in length. In other instances, a guide sequence is about 15 nucleotides in length. In other instances, a guide sequence is about 25 nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

The nucleotide sequence of a modified sgRNA can be selected using any of the web-based software described above. Considerations for selecting a DNA-targeting RNA include the PAM sequence for the Cas nuclease (e.g., Cas9 polypeptide) to be used, and strategies for minimizing off-target modifications. Tools, such as the CRISPR Design Tool, can provide sequences for preparing the modified sgRNA, for assessing target modification efficiency, and/or assessing cleavage at off-target sites. Another consideration for selecting the sequence of a modified sgRNA includes reducing the degree of secondary structure within the guide sequence. Secondary structure may be determined by any suitable polynucleotide folding algorithm. Some programs are based on calculating the minimal Gibbs free energy. Examples of suitable algorithms include mFold (Zuker and Stiegler, *Nucleic Acids Res,* 9 (1981), 133-148), UNAFold package (Markham et al., Methods Mol Biol, 2008, 453:3-31) and RNAfold form the ViennaRNa Package.

One or more nucleotides of the guide sequence and/or one or more nucleotides of the scaffold sequence of the modified sgRNA can be a modified nucleotide. For instance, a guide sequence that is about 20 nucleotides in length may have 1 or more, e.g., 1, 2, 3, 4, 5, 6, 7, 8, 9, 10, 11, 12, 13, 14, 15, 16, 17, 18, 19, 20, or more modified nucleotides. In some cases, the guide sequence includes at least 2, 3, 4, 5, 6, 7, 8, 9, 10, or more modified nucleotides. In other cases, the guide sequence includes at least 2, 3, 4, 5, 6, 7, 8, 9, 10, 11, 12, 13, 14, 15, 16, 17, 19, 20, or more modified nucleotides. The modified nucleotides can be located at any nucleic acid position of the guide sequence. In other words, the modified nucleotides can be at or near the first and/or last nucleotide of the guide sequence, and/or at any position in between. For example, for a guide sequence that is 20 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, and/or position 20 of the guide sequence. In certain instances, from about 10% to about 30%, e.g., about 10% to about 25%, about 10% to about 20%, about 10% to about 15%, about 15% to about 30%, about 20% to about 30%, or about 25% to about 30% of the guide sequence can comprise modified nucleotides. In other instances, from about 10% to about 30%, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% of the guide sequence can comprise modified nucleotides.

In some embodiments, the scaffold sequence of the modified sgRNA contains one or more modified nucleotides. For example, a scaffold sequence that is about 80 nucleotides in length may have 1 or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 76, 77, 78, 79, 80, or more modified nucleotides. In some instances, the scaffold sequence includes at least 2, 3, 4, 5, 6, 7, 8, 9, 10, or more modified nucleotides. In other instances, the scaffold sequence includes at least 2, 3, 4, 5, 6, 7, 8, 9, 10, 11, 12, 13, 14, 15, 16, 17, 19, 20, or more modified nucleotides. The modified nucleotides can be located at any nucleic acid position of the scaffold sequence. For example, the modified nucleotides can be at or near the first and/or last nucleotide of the scaffold sequence, and/or at any position in between. For example, for a scaffold sequence that is about 80 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, position 36, position 37, position 38, position 39, position 40, position 41, position 42, position 43, position 44, position 45, position 46, position 47, position 48, position 49, position 50, position 51, position 52, position 53, position 54, position 55, position 56, position 57, position 58, position 59, position 60, position 61, position 62, position 63, position 64, position 65, position 66, position 67, position 68, position 69, position 70, position 71, position 72, position 73, position 74, position 75, position 76, position 77, position 78, position 79, and/or position 80 of the sequence. In some instances, from about 1% to about 10%, e.g., about 1% to about 8%, about 1% to about 5%, about 5% to about 10%, or about 3% to about 7% of the scaffold sequence can comprise modified nucleotides. In other instances, from about 1% to about 10%, e.g., about 1%, about 2%, about 3%, about 4%, about 5%, about 6%, about 7%, about 8%, about 9%, or about 10% of the scaffold sequence can comprise modified nucleotides.

The modified nucleotides of the sgRNA can include a modification in the ribose (e.g., sugar) group, phosphate group, nucleobase, or any combination thereof. In some embodiments, the modification in the ribose group comprises a modification at the 2' position of the ribose.

In some embodiments, the modified nucleotide includes a 2'fluoro-arabino nucleic acid, tricycle-DNA (tc-DNA), peptide nucleic acid, cyclohexene nucleic acid (CeNA), locked nucleic acid (LNA), ethylene-bridged nucleic acid (ENA), a phosphodiamidate morpholino, or a combination thereof.

Modified nucleotides or nucleotide analogues can include sugar- and/or backbone-modified ribonucleotides (i.e., include modifications to the phosphate-sugar backbone). For example, the phosphodiester linkages of a native or natural RNA may be modified to include at least one of a nitrogen or sulfur heteroatom. In some backbone-modified ribonucleotides the phosphoester group connecting to adjacent ribonucleotides may be replaced by a modified group, e.g., of phosphothioate group. In preferred sugar-modified ribonucleotides, the 2' moiety is a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In some embodiments, the modified nucleotide contains a sugar modification. Non-limiting examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof.

In some embodiments, the modified sgRNA contains one or more 2'-fluro, 2'-amino and/or 2'-thio modifications. In some instances, the modification is a 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, 5-amino-allyl-uridine, 5-bromo-uridine, 5-iodo-uridine, 5-methyl-cytidine, ribo-thymidine, 2-aminopurine, 2'-amino-butyryl-pyrene-uridine, 5-fluoro-cytidine, and/or 5-fluoro-uridine.

There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art and described in, e.g., U.S. Pat. Nos. 4,373,071, 4,458,066, 4,500,707, 4,668,777, 4,973,679, 5,047,524, 5,132,418, 5,153,319, 5,262,530, and 5,700,642. Numerous modified nucleosides and modified nucleotides that are suitable for use as described herein are commercially available. The nucleoside can be an analogue of a naturally occurring nucleoside. In some cases, the analogue is dihydrouridine, methyladenosine, methylcytidine, methyluridine, methylpseudouridine, thiouridine, deoxycytodine, and deoxyuridine.

In some cases, the modified sgRNA described herein includes a nucleobase-modified ribonucleotide, i.e., a ribonucleotide containing at least one non-naturally occurring nucleobase instead of a naturally occurring nucleobase. Non-limiting examples of modified nucleobases which can be incorporated into modified nucleosides and modified nucleotides include m5C (5-methylcytidine), m5U (5-methyluridine), m6A (N6-methyladenosine), s2U (2-thiouridine), Um (2'-O-methyluridine), m1A (1-methyl adenosine), m2A (2-methyladenosine), Am (2-1-O-methyladenosine), ms2m6A (2-methylthio-N6-methyladenosine), i6A (N6-isopentenyl adenosine), ms2i6A (2-methylthio-N6isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A(N6.-hydroxynorvalylcarbamoyl adenosine), ms2hn6A (2-methylthio-N6-hydroxynorvalyl carbamoyladenosine), Ar(p) (2'-O-ribosyladenosine(phosphate)), I (inosine), m1I (1-methylinosine), m'Im (1,2'-O-dimethylinosine), m3C (3-methylcytidine), Cm (2T-O-methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-O-methyl-guanosine), m22G (N2,N2-dimethylguanosine), m2Gm (N2,2'-O-dimethylguanosine), m22Gm (N2,N2,2'-O-trimethylguanosine), Gr(p) (2'-O-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-O-dimethyluridine), s4U (4-thiouridine), m5 s2U (5-methyl-2-thiouridine), s2Um (2-thio-2'-O-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5s2U (5-methoxycarbonylmethyl-2-thiouridine), nm5 s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-O-methyluridine), cmnm5U (5-carboxymethylaminomethyluridine), cmnm5Um (5-carboxymethylaminomethyl-2-L-Omethyluridine), cmnm5s2U (5-carboxymethylaminomethyl-2-thiouridine), m62A (N6,N6-dimethyladenosine), Tm (2'-O-methylinosine), m4C (N4-methylcytidine), m4Cm (N4,2-O-dimethylcytidine), hm5C (5-hydroxymethylcytidine), m3U (3-methyluridine), cm5U (5-carboxymethyluridine), m6Am (N6,T-O-dimethyladenosine), rn62Am (N6,N6,O-2-trimethyladenosine), m2'7G (N2,7-dimethylguanosine), m2'2'7G (N2,N2,7-trimethylguanosine), m3Um (3,2T-O-dimethyluridine), m5D (5-methyldihydrouridine), f5Cm (5-formyl-2'-O-methylcytidine), m1Gm (1,2'-O-dimethylguanosine), m'Am (1,2-O-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-($C_2$-$C_6$) alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

In some embodiments, the phosphate backbone of the modified sgRNA is altered. The modified sgRNA can include one or more phosphorothioate, phosphoramidate (e.g., N3'-P5'-phosphoramidate (NP)), 2'-O-methoxy-ethyl (2'MOE), 2'-O-methyl-ethyl (2'ME), and/or methylphosphonate linkages.

In particular embodiments, one or more of the modified nucleotides of the guide sequence and/or one or more of the modified nucleotides of the scaffold sequence of the modified sgRNA include a 2'-O-methyl (M) nucleotide, a 2'-O-methyl 3'-phosphorothioate (MS) nucleotide, a 2'-O-methyl 3'thioPACE (MSP) nucleotide, or a combination thereof. In some instances, the modified sgRNA includes one or more MS nucleotides. In other instances, the modified sgRNA includes one or more MSP nucleotides. In yet other instances, the modified sgRNA includes one or more MS nucleotides and one or more MSP nucleotides. In further instances, the modified sgRNA does not include M nucleotides. In certain instances, the modified sgRNA includes one or more MS nucleotides and/or one or more MSP nucleotides, and further includes one or more M nucleotides. In certain other instances, MS nucleotides and/or MSP nucleotides are the only modified nucleotides present in the modified sgRNA.

It should be noted that any of the modifications described herein may be combined and incorporated in the guide sequence and/or the scaffold sequence of the modified sgRNA.

In some cases, the modified sgRNA also includes a structural modification such as a stem loop, e.g., M2 stem loop or tetraloop.

The modified sgRNA can be synthesized by any method known to one of ordinary skill in the art. In some embodiments, the modified sgRNA is chemically synthesized. Modified sgRNAs can be synthesized using 2'-O-thionocarbamate-protected nucleoside phosphoramidites. Methods are described in, e.g., Dellinger et al., *J.American Chemical Society* 133, 11540-11556 (2011); Threlfall et al., *Organic & Biomolecular Chemistry* 10, 746-754 (2012); and Dellinger et al., *J. American Chemical Society* 125, 940-950 (2003).

The chemically modified sgRNAs can be used with any CRISPR-associated technology, e.g., and RNA-guided technology. As described herein, the modified sgRNA can serve as a guide for any Cas nuclease or variant or fragment thereof, including any engineered or man-made Cas9 polypeptide. The modified sgRNAs can target DNA and/or RNA molecules in isolated primary cells for ex vivo therapy or in vivo (e.g., in an animal). The methods disclosed herein can be applied to genome editing, gene regulation, imaging, and any other CRISPR-based applications.

3. Donor Repair Template

In some embodiments, the present invention provides a recombinant donor repair template comprising two homology arms that are homologous to portions of a target DNA sequence (e.g., target gene or locus) at either side of a Cas nuclease (e.g., Cas9 nuclease) cleavage site. In certain instances, the recombinant donor repair template comprises a reporter cassette that includes a nucleotide sequence encoding a reporter polypeptide (e.g., a detectable polypeptide, fluorescent polypeptide, or a selectable marker), and two homology arms that flank the reporter cassette and are homologous to portions of the target DNA at either side of the Cas nuclease cleavage site. The reporter cassette can further comprise a sequence encoding a self-cleavage peptide, one or more nuclear localization signals, and/or a fluorescent polypeptide, e.g. superfolder GFP (sfGFP).

In some embodiments, the homology arms are the same length. In other embodiments, the homology arms are different lengths. The homology arms can be at least about 10 base pairs (bp), e.g., at least about 10 bp, 15 bp, 20 bp, 25 bp, 30 bp, 35 bp, 45 bp, 55 bp, 65 bp, 75 bp, 85 bp, 95 bp, 100 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1000 bp, 1.1 kilobases (kb), 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3.0 kb, 3.1 kb, 3.2 kb, 3.3 kb, 3.4 kb, 3.5 kb, 3.6 kb, 3.7 kb, 3.8 kb, 3.9 kb, 4.0 kb, or longer. The homology arms can be about 10 bp to about 4 kb, e.g., about 10 bp to about 20 bp, about 10 bp to about 50 bp, about 10 bp to about 100 bp, about 10 bp to about 200 bp, about 10 bp to about 500 bp, about 10 bp to about 1 kb, about 10 bp to about 2 kb, about 10 bp to about 4 kb, about 100 bp to about 200 bp, about 100 bp to about 500 bp, about 100 bp to about 1 kb, about 100 bp to about 2 kb, about 100 bp to about 4 kb, about 500 bp to about 1 kb, about 500 bp to about 2 kb, about 500 bp to about 4 kb, about 1 kb to about 2 kb, about 1 kb to about 4 kb, or 2 kb to about 4 kb.

The donor repair template can be cloned into an expression vector. Conventional viral and non-viral based expression vectors known to those of ordinary skill in the art can be used.

In place of a recombinant donor repair template, a single-stranded oligodeoxynucleotide (ssODN) donor template can be used for homologous recombination-mediated repair. An ssODN is useful for introducing short modifications within a target DNA. For instance, ssODN are suited for precisely correcting genetic mutations such as SNPs. ssODNs can contain two flanking, homologous sequences on each side of the target site of Cas nuclease cleavage and can be oriented in the sense or antisense direction relative to the target DNA. Each flanking sequence can be at least about 10 base pairs (bp), e.g., at least about 10 bp, 15 bp, 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 950 bp, 1 kb, 2 kb, 4 kb, or longer. In some embodiments, each homology arm is about 10 bp to about 4 kb, e.g., about 10 bp to about 20 bp, about 10 bp to about 50 bp, about 10 bp to about 100 bp, about 10 bp to about 200 bp, about 10 bp to about 500 bp, about 10 bp to about 1 kb, about 10 bp to about 2 kb, about 10 bp to about 4 kb, about 100 bp to about 200 bp, about 100 bp to about 500 bp, about 100 bp to about 1 kb, about 100 bp to about 2 kb, about 100 bp to about 4 kb, about 500 bp to about 1 kb, about 500 bp to about 2 kb, about 500 bp to about 4 kb, about 1 kb to about 2 kb, about 1 kb to about 4 kb, or about 2 kb to about 4 kb. The ssODN can be at least about 25 nucleotides (nt) in length, e.g., at least about 25 nt, 30 nt, 35 nt, 40 nt, 45 nt, 50 nt, 55 nt, 60 nt, 65 nt, 70 nt, 75 nt, 80 nt, 85 nt, 90 nt, 95 nt, 100 nt, 150 nt, 200 nt, 250 nt, 300 nt, or longer. In some embodiments, the ssODN is about 25 to about 50; about 50 to about 100; about 100 to about 150; about 150 to about 200; about 200 to about 250; about 250 to about 300; or about 25 nt to about 300 nt in length.

In some embodiments, the ssODN template comprises at least one, e.g., 1, 2, 3, 4, 5, 6, 7, 8, 9, 10, 20, 30, 40, 50, 60, 70, 80, 90, 100, 200, 300, 400, 500, or more modified nucleotides described herein. In some instances, at least 1%, 5%, 10%, 20%, 30%, 40%, 50%, 60%, 70%, 80%, 90%, or 99% of the sequence of the ssODN includes a modified nucleotide. In some embodiments, the modified nucleotides are located at one or both of the terminal ends of the ssODN. The modified nucleotides can be at the first, second, third, fourth, fifth, sixth, seventh, eighth, ninth, or tenth terminal nucleotide, or any combination thereof. For instance, the modified nucleotides can be at the three terminal nucleotides at both ends of the ssODN template. Additionally, the modified nucleotides can be located internal to the terminal ends.

4. Target DNA

In the CRISPR/Cas system, the target DNA sequence can be complementary to a fragment of a DNA-targeting RNA (e.g., modified sgRNA) and can be immediately followed by a protospacer adjacent motif (PAM) sequence. The target DNA site may lie immediately 5' of a PAM sequence, which is specific to the bacterial species of the Cas9 used. For instance, the PAM sequence of *Streptococcus pyogenes*-derived Cas9 is NGG; the PAM sequence of *Neisseria meningitidis*-derived Cas9 is NNNNGATT; the PAM sequence of *Streptococcus thermophilus*-derived Cas9 is NNAGAA; and the PAM sequence of *Treponema denticola*-derived Cas9 is NAAAAC. In some embodiments, the PAM sequence can be 5'-NGG, wherein N is any nucleotide; 5'-NRG, wherein N is any nucleotide and R is a purine; or 5'-NNGRR, wherein N is any nucleotide and R is a purine. For the *S. pyogenes* system, the selected target DNA sequence should immediately precede (e.g., be located 5') a 5'NGG PAM, wherein N is any nucleotide, such that the guide sequence of the DNA-targeting RNA (e.g., modified sgRNA) base pairs with the opposite strand to mediate cleavage at about 3 base pairs upstream of the PAM sequence.

In some embodiments, the degree of complementarity between a guide sequence of the DNA-targeting RNA (e.g., modified sgRNA) and its corresponding target DNA sequence, when optimally aligned using a suitable alignment algorithm, is about or more than about 50%, 55%, 60%, 65%, 70%, 75%, 80%, 85%, 90%, 91%, 92%, 93%, 94%, 95%, 96%, 97%, 98%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, Selangor, Malaysia), and ELAND (Illumina, San Diego, Calif.).

The target DNA site can be selected in a predefined genomic sequence (gene) using web-based software such as ZiFiT Targeter software (Sander et al., 2007, *Nucleic Acids Res*, 35:599-605; Sander et al., 2010, *Nucleic Acids Res*, 38:462-468), E-CRISP (Heigwer et al., 2014, *Nat Methods*, 11:122-123), RGEN Tools (Bae et al., 2014, *Bioinformatics*, 30(10):1473-1475), CasFinder (Aach et al., 2014, bioRxiv), DNA2.0 gNRA Design Tool (DNA2.0, Menlo Park, Calif.), and the CRISPR Design Tool (Broad Institute, Cambridge, Mass.). Such tools analyze a genomic sequence (e.g., gene or locus of interest) and identify suitable target site for gene editing. To assess off-target gene modifications for each DNA-targeting RNA (e.g., modified sgRNA), computationally predictions of off-target sites are made based on quantitative specificity analysis of base-pairing mismatch identity, position and distribution.

5. Modulating Gene Expression

The CRISPR/Cas system of regulating gene expression, such as inhibiting gene expression or activating gene expression, can include a variant or fragment of the wild-type or native Cas nuclease (e.g., Cas9 polypeptide variant or fragment) and either a DNA-targeting sgRNA or an RNA-targeting sgRNA. As a non-limiting example, a complex comprising a Cas9 variant or fragment and an sgRNA that can bind to a target DNA sequence complementary to a portion of the sgRNA can block or hinder transcription initiation and/elongation by RNA polymerase. This, in turn, can inhibit or repress gene expression of the target DNA. Alternatively, a complex comprising a different Cas9 variant or fragment and an sgRNA that can bind to a target DNA sequence complementary to a portion of the sgRNA can induce or activate gene expression of the target DNA.

Detailed descriptions of methods for performing CRISPR interference (CRISPRi) to inactivate or reduce gene expression are found in, e.g., Larson et al., *Nature Protocols*, 2013, 8(11):2180-2196, and Qi et al., *Cell*, 152, 2013, 1173-1183. In CRISPRi, the sgRNA-Cas9 variant complex can bind to a nontemplate DNA strand of a protein coding region and block transcription elongation. In some cases, when the sgRNA-Cas9 variant complex binds to a promoter region of a gene, the complex prevents or hinders transcription initiation.

Detailed descriptions of methods for performing CRISPR activation to increase gene expression are found in, e.g., Cheng et al., *Cell Research*, 2013, 23:1163-1171, Konerman et al., *Nature*, 2015, 517:583-588, and U.S. Pat. No. 8,697, 359.

Detailed descriptions of methods for CRISPR-based RNA binding and/or cleavage for modulating gene expression are found in, e.g., O'Connell et al., *Nature*, 2014, 516:263-266, and U.S. Patent Application Publication No. 2014/0302563.

For CRISPR-based control of gene expression, a catalytically inactive variant of the Cas nuclease (e.g., Cas9 polypeptide) that lacks endonucleolytic activity can be used. In some embodiments, the Cas nuclease is a Cas9 variant that contains at least two point mutations in the RuvC-like and HNH nuclease domains. In some embodiments, the Cas9 variant has D10A and H840A amino acid substitutions, which is referred to as dCas9 (Jinek et al., *Science*, 2012, 337:816-821; Qi et al., *Cell*, 152(5):1173-1183). In some cases, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983 or D986, as well as a mutation at H840 or N863. In some cases, the dCas9 enzyme contains a D10A or D10N mutation. Also, the dCas9 enzyme can include a H840A, H840Y, or H840N. In some cases, the dCas9 enzyme comprises D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target DNA.

In certain embodiments, the dCas9 polypeptide is catalytically inactive such as defective in nuclease activity. In some instances, the dCas9 enzyme or a variant or fragment thereof can block transcription of a target sequence, and in some cases, block RNA polymerase. In other instances, the dCas9 enzyme or a variant or fragment thereof can activate transcription of a target sequence.

In certain embodiments, the Cas9 variant lacking endonucleolytic activity (e.g., dCas9) can be fused to a transcriptional repression domain, e.g., a Kruppel associated box (KRAB) domain, or a transcriptional activation domain, e.g., a VP16 transactivation domain. In some embodiments, the Cas9 variant is a fusion polypeptide comprising dCas9 and a transcription factor, e.g., RNA polymerase omega factor, heat shock factor 1, or a fragment thereof. In other embodiments, the Cas9 variant is a fusion polypeptide comprising dCas9 and a DNA methylase, histone acetylase, or a fragment thereof.

For CRISPR-based control of gene expression mediated by RNA binding and/or RNA cleavage, a suitable Cas nuclease (e.g., Cas9 polypeptide) variant having endoribonuclease activity, as described in, e.g., O'Connell et al., *Nature*, 2014, 516:263-266, can be used. Other useful Cas nuclease (e.g., Cas9) variants are described in, e.g., U.S. Patent Application Publication No. 2014/0302563. Other CRISPR-related enzymes that can cleave RNA include a Csy4 endoribonuclease, a CRISPR-related Cas6 enzyme, a Cas5 family member enzyme, a Cas6 family member enzyme, a Type I CRISPR system endoribonuclease, a Type II CRISPR system endoribonuclease, a Type III CRISPR system endoribonuclease, and variants thereof.

In some embodiments of CRISPR-based RNA cleavage, a DNA oligonucleotide containing a PAM sequence (e.g., PAMmer) is used with the modified sgRNA and Cas nuclease (e.g., Cas9) variant described herein to bind to and cleave a single-stranded RNA transcript. Detailed descriptions of suitable PAMmer sequences are found in, e.g., O'Connell et al., *Nature*, 2014, 516:263-266.

The Cas nuclease (e.g., Cas9 polypeptide) or variants or fragments thereof can be provided as a polypeptide, an mRNA encoding the polypeptide or a recombinant expression vector comprising a nucleotide sequence encoding the polypeptide. Additional details can be found above.

In some embodiments, a plurality of modified sgRNAs is used to target different regions of a target gene to regulate gene expression of that target gene. The plurality of modified sgRNAs can provide synergistic modulation (e.g., inhibition or activation) of gene expression of a single target gene compared to each modified sgRNA alone. In other embodiments, a plurality of modified sgRNAs is used to regulate gene expression of at least two target genes.

B. Primary Cells

The present invention can be used to induce gene regulation of a target nucleic acid in any primary cell of interest. The primary cell can be a cell isolated from any multicellular organism, e.g., a plant cell (e.g., a rice cell, a wheat cell, a tomato cell, an *Arabidopsis thaliana* cell, a *Zea mays* cell, and the like), a cell from a multicellular protist, a cell from a multicellular fungus, an animal cell such as a cell from an invertebrate animal (e.g., fruit fly, cnidarian, echinoderm, nematode, etc.) or a cell from a vertebrate animal (e.g., fish, amphibian, reptile, bird, mammal, etc.), a cell from a human, a cell from a healthy human, a cell from a human patient, a cell from a cancer patient, etc. In some cases, the primary cell with induced gene regulation can be transplanted to a subject (e.g., patient). For instance, the primary cell can be derived from the subject (e.g., patient) to be treated.

Any type of primary cell may be of interest, such as a stem cell, e.g., embryonic stem cell, induced pluripotent stem cell, adult stem cell (e.g., mesenchymal stem cell, neural stem cell, hematopoietic stem cell, organ stem cell), a progenitor cell, a somatic cell (e.g., fibroblast, hepatocyte, heart cell, liver cell, pancreatic cell, muscle cell, skin cell, blood cell, neural cell, immune cell), and any other cell of the body, e.g., human body. The cells can be primary cells or primary cell cultures derived from a subject, e.g., an animal subject or a human subject, and allowed to grow in vitro for a limited number of passages. In some embodiments, the cells are disease cells or derived from a subject with a disease. For instance, the cells can be cancer or tumor cells.

Primary cells can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma or serum. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem and progenitor cell (HSPC) such as CD34+ HSPCs, or a non-pluripotent stem cell. In some cases, the cell can be any immune cell including, but not limited to, any T cell such as tumor infiltrating cells (TILs), CD3+ T cells, CD4+ T cells, CD8+ T cells, or any other type of T cell. The T cell can also include memory T cells, memory stem T cells, or effector T cells. The T cells can also be skewed towards particular populations and phenotypes. For example, the T cells can be skewed to phenotypically comprise CD45RO(−), CCR7(+), CD45RA(+), CD62L(+), CD27(+), CD28(+) and/or IL-7Rα (+). Suitable cells can be selected that comprise one of more markers selected from a list comprising CD45RO(−), CCR7 (+), CD45RA(+), CD62L(+), CD27(+), CD28(+) and/or IL-7Rα(+). Induced pluripotent stem cells can be generated from differentiated cells according to standard protocols described in, for example, U.S. Pat. Nos. 7,682,828, 8,058, 065, 8,530,238, 8,871,504, 8,900,871 and 8,791,248.

In some embodiments, the primary cell is in vitro. In other embodiments, the primary cell is ex vivo.

C. Ex Vivo Therapy

The methods described herein can be used in ex vivo therapy. Ex vivo therapy can comprise administering a composition (e.g., a cell) generated or modified outside of an organism to a subject (e.g., patient). In some embodiments, the composition (e.g., a cell) can be generated or modified by the methods disclosed herein. For example, ex vivo therapy can comprise administering a primary cell generated or modified outside of an organism to a subject (e.g., patient), wherein the primary cell has been cultured in vitro in accordance with the methods of the present invention that includes contacting the target nucleic acid in the primary cell with one or more modified sgRNAs described herein and a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof.

In some embodiments, the composition (e.g., a cell) can be derived from the subject (e.g., patient) to be treated by ex vivo therapy. In some embodiments, ex vivo therapy can include cell-based therapy, such as adoptive immunotherapy.

In some embodiments, the composition used in ex vivo therapy can be a cell. The cell can be a primary cell, including but not limited to, peripheral blood mononuclear cells (PBMCs), peripheral blood lymphocytes (PBLs), and other blood cell subsets. The primary cell can be an immune cell. The primary cell can be a T cell (e.g., CD3+ T cells, CD4+ T cells, and/or CD8+ T cells), a natural killer cell, a monocyte, a natural killer T cell, a monocyte-precursor cell, a hematopoietic stem cell or a non-pluripotent stem cell, a stem cell, or a progenitor cell. The primary cell can be a hematopoietic stem or progenitor cell (HSPC) such as CD34+ HSPCs. The primary cell can be a human cell. The primary cell can be isolated, selected, and/or cultured. The primary cell can be expanded ex vivo. The primary cell can be expanded in vivo. The primary cell can be CD45RO(−), CCR7(+), CD45RA(+), CD62L(+), CD27(+), CD28(+), and/or IL-7Rα(+). The primary cell can be autologous to a subject in need thereof. The primary cell can be non-autologous to a subject in need thereof. The primary cell can be a good manufacturing practices (GMP) compatible reagent. The primary cell can be a part of a combination therapy to treat diseases, including cancer, infections, autoimmune disorders, or graft-versus-host disease (GVHD), in a subject in need thereof.

As a non-limiting example of ex vivo therapy, a primary cell can be isolated from a multicellular organism (e.g., a plant, multicellular protist, multicellular fungus, invertebrate animal, vertebrate animal, etc.) prior to contacting a target nucleic acid within the primary cell with a Cas nuclease and a modified sgRNA. After contacting the target nucleic acid with the Cas nuclease and the modified sgRNA, the primary cell or its progeny (e.g., a cell derived from the primary cell) can be returned to the multicellular organism.

D. Methods for Introducing Nucleic Acids into Target Cells

Methods for introducing polypeptides and nucleic acids into a target cell (host cell) are known in the art, and any known method can be used to introduce a nuclease or a nucleic acid (e.g., a nucleotide sequence encoding the nuclease, a DNA-targeting RNA (e.g., a modified single guide RNA), a donor repair template for homology-directed repair (HDR), etc.) into a cell, e.g., a primary cell such as a stem cell, a progenitor cell, or a differentiated cell. Non-limiting examples of suitable methods include electroporation, viral or bacteriophage infection, transfection, conjugation, protoplast fusion, lipofection, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

In some embodiments, the components of CRISPR/Cas-mediated gene regulation can be introduced into a cell using a delivery system. In certain instances, the delivery system comprises a nanoparticle, a microparticle (e.g., a polymer micropolymer), a liposome, a micelle, a virosome, a viral particle, a nucleic acid complex, a transfection agent, an electroporation agent (e.g., using a NEON transfection system), a nucleofection agent, a lipofection agent, and/or a buffer system that includes a nuclease component (as a polypeptide or encoded by an expression construct) and one or more nucleic acid components such as a DNA-targeting RNA (e.g., a modified single guide RNA) and/or a donor repair template. For instance, the components can be mixed with a lipofection agent such that they are encapsulated or packaged into cationic submicron oil-in-water emulsions. Alternatively, the components can be delivered without a delivery system, e.g., as an aqueous solution.

Methods of preparing liposomes and encapsulating polypeptides and nucleic acids in liposomes are described in, e.g., Methods and Protocols, Volume 1: Pharmaceutical Nanocarriers: Methods and Protocols. (ed. Weissig). Humana Press, 2009 and Heyes et al. (2005)*J Controlled Release* 107:276-87. Methods of preparing microparticles and encapsulating polypeptides and nucleic acids are described in, e.g., Functional Polymer Colloids and Microparticles volume 4 (Microspheres, microcapsules & liposomes). (eds. Arshady & Guyot). Citus Books, 2002 and *Microparticulate Systems for the Delivery of Proteins and Vaccines*. (eds. Cohen & Bernstein). CRC Press, 1996.

E. Methods for Assessing the Efficiency of Genome Editing

To functionally test the presence of the correct genomic editing modification, the target DNA can be analyzed by standard methods known to those in the art. For example, indel mutations can be identified by sequencing using the SURVEYOR® mutation detection kit (Integrated DNA Technologies, Coralville, Iowa) or the Guide-It™ Indel Identification Kit (Clontech, Mountain View, Calif.). Homology-directed repair (HDR) can be detected by PCR-based methods, and in combination with sequencing or RFLP analysis. Non-limiting examples of PCR-based kits include the Guide-it Mutation Detection Kit (Clontech) and the GeneArt® Genomic Cleavage Detection Kit (Life Technologies, Carlsbad, Calif.). Deep sequencing can also be used, particularly for a large number of samples or potential target/off-target sites.

In certain embodiments, the efficiency (e.g., specificity) of genome editing corresponds to the number or percentage of on-target genome cleavage events relative to the number or percentage of all genome cleavage events, including on-target and off-target events.

In some embodiments, the modified sgRNAs described herein are capable of enhancing genome editing of a target DNA sequence in a cell such as a primary cell relative to the corresponding unmodified sgRNAs. The genome editing can comprise homology-directed repair (HDR) (e.g., insertions, deletions, or point mutations) or nonhomologous end joining (NHEJ).

In certain embodiments, the nuclease-mediated genome editing efficiency of a target DNA sequence in a cell is enhanced by at least about 0.5-fold, 0.6-fold, 0.7-fold, 0.8-fold, 0.9-fold, 1-fold, 1.1-fold, 1.2-fold, 1.3-fold, 1.4-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 25-fold, 30-fold, 35-fold, 40-fold, 45-fold, 50-fold, or greater in the presence of a modified sgRNA described herein compared to the corresponding unmodified sgRNA sequence.

F. Methods for Gene Regulation of a Target Nucleic Acid in a Cell

Provided herein is a method for inducing gene regulation, e.g., genome editing and/or modulating (e.g., inhibiting or activating) gene expression, of a target nucleic acid in a cell. The cell can be in vitro (e.g., a primary cell for use in ex vivo therapy) or in vivo (e.g., a cell in an organ or tissue of a subject such as a human).

The method for inducing genome editing includes introducing into a cell the modified sgRNA described herein and either a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof. The modified sgRNA guides the Cas nuclease (e.g., Cas9 polypeptide) or variant or fragment thereof to the target nucleic acid (e.g., target DNA). The modified sgRNA has enhanced activity, stability, and/or specificity for the target DNA compared to a corresponding unmodified sgRNA sequence. In some cases, the genome editing is nonhomologous end joining (NHEJ) of the target DNA. In other cases, the genome editing is homologous-directed repair (HDR) of the target DNA. In some embodiments of HDR, a recombinant donor repair template is added to the cell. The recombinant donor repair template can include two nucleotide sequences comprising two non-overlapping, homologous portions of the target DNA, wherein the nucleotide sequences are located at the 5' and 3' ends of a nucleotide sequence corresponding to the target DNA. In some embodiments, the recombinant donor repair template comprises a synthetic single stranded oligodeoxynucleotide (ssODN) template comprising a nucleotide sequence encoding a mutation to correct a single nucleotide polymorphism (SNP) and two nucleotide sequences comprising two non-overlapping, homologous portions of the target DNA, wherein the nucleotide sequences are located at the 5' and 3' ends of nucleotide sequence encoding the mutation. The modified sgRNA and/or either a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof are introduced into the cell using any suitable method such as by electroporation.

The method for modulating (e.g., inhibiting or activating) gene expression of a target nucleic acid, e.g., a target DNA, in a cell includes introducing (e.g., electroporating) into the cell the modified sgRNA described herein and either a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof. In some embodiments, the Cas nuclease (e.g., Cas9) variant is an endonuclease-deficient Cas (e.g., dCas9) polypeptide. In some instances, the Cas9 variant can have two or more amino acid substitutions compared to the wild-type Cas9 polypeptide. In other instances, the Cas9 variant cannot cleave double-stranded DNA. The Cas nuclease variant can be a Cas (e.g., dCas9) fusion polypeptide. In some embodiments, the fusion polypeptide includes a transcriptional repression domain, a transcriptional activation domain, transcription factor, histone modifying enzyme (e.g., histone deacetylase, histone methyltransferase, histone acetyltransferase), a DNA modifying enzyme (e.g., DNA methyltransferase), and the like.

The method for modulating (e.g., inhibiting or activating) gene expression of a target nucleic acid, e.g., a target RNA, in a cell includes introducing (e.g., electroporating) into the cell the modified sgRNA described herein and either a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof. In some embodiments, the Cas nuclease (e.g., Cas9) variant has reduced or lacks endonucleolytic activity. The Cas nuclease variant can contain two or more amino acid substitutions such that the polypeptide is unable to cleave double-stranded DNA. The Cas nuclease (e.g., Cas9) variant can have endoribonuclease activity and can cleave target RNA.

G. Methods for Preventing or Treating a Genetic Disease in a Subject

The modified sgRNAs described herein can be used to modulate the efficiency of gene regulation. For example, the modified sgRNA can induce gene regulation with an enhanced activity relative to a corresponding unmodified sgRNA. In some cases, the enhanced activity comprises increased stability of the modified sgRNA and/or increased specificity of the modified sgRNA for a target nucleic acid. As another example, the modified sgRNA can induce gene regulation with a decrease in cellular toxicity relative to a corresponding unmodified sgRNA.

The modified sgRNAs can be applied to targeted nuclease-based therapeutics of genetic diseases. Current approaches for precisely correcting genetic mutations in the genome of primary patient cells have been very inefficient (less than 1 percent of cells can be precisely edited). The modified sgRNAs provided herein can enhance the activity of genome editing and increase the efficacy of genome editing-based therapies. In particular embodiments, the modified sgRNAs may be used for in vivo gene editing of genes in subjects with a genetic disease. The modified sgRNAs can be administered to a subject via any suitable route of administration and at doses or amounts sufficient to enhance the effect (e.g., improve the genome editing efficiency) of the nuclease-based therapy.

Provided herein is a method for preventing or treating a genetic disease in a subject in need thereof by correcting a genetic mutation associated with the disease. The method includes administering to the subject a modified sgRNA described herein in an amount that is sufficient to correct the mutation. Also provided herein is the use of a modified sgRNA described herein in the manufacture of a medicament for preventing or treating a genetic disease in a subject in need thereof by correcting a genetic mutation associated with the disease. The modified sgRNA can be contained in a composition that also includes a Cas nuclease (e.g., Cas9 polypeptide) or variant or fragment thereof, an mRNA encoding a Cas nuclease (e.g., Cas9 polypeptide) or variant or fragment thereof, or a recombinant expression vector comprising a nucleotide sequence encoding a Cas nuclease (e.g., Cas9 polypeptide) or variant or fragment thereof. In some instances, the modified sgRNA is included in a delivery system described above.

The genetic diseases that may be corrected by the method include, but are not limited to, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disease or disorders, inflammation, immune-related diseases or disorders, metabolic diseases, liver diseases and disorders, kidney diseases and disorders, muscular/skeletal diseases and disorders (e.g., muscular dystrophy, Duchenne muscular dystrophy), neurological and neuronal diseases and disorders, cardiovascular diseases and disorders, pulmonary diseases and disorders, ocular diseases and disorders, viral infections (e.g., HIV infection), and the like.

V. Examples

The following examples are offered to illustrate, but not to limit, the claimed invention.

Example 1. Chemically Modified Guide RNAs Enhance CRISPR/Cas Genome Editing in Human Primary Cells CRISPR/Cas-mediated genome editing relies on guide RNAs that direct site-specific DNA cleavage facilitated by the Cas endonuclease. Here we report on the use of chemically synthesized single guide RNAs (sgRNAs) and show that modification of the sgRNAs by chemical alterations dramatically enhances genome editing in human primary T cells and CD34+ hematopoietic stem and progenitor cells. This approach is a simple and highly effective way to streamline the development of genome editing with the potential to accelerate a wide array of biotechnological and therapeutic applications of the CRISPR/Cas technology.

Genome editing with engineered nucleases is a breakthrough technology for modifying essentially any genomic sequence of interest (Porteus, M. H. & Carroll, D., *Nature biotechnology* 23, 967-973 (2005)). This technology exploits engineered nucleases to generate site-specific double-strand breaks (DSBs) followed by resolution of DSBs by endogenous cellular repair mechanisms. The outcome can be either mutation of a specific site through mutagenic nonhomologous end-joining (NHEJ), creating insertions or deletions (in/dels) at the site of the break, or precise change of a genomic sequence through homologous recombination (HR) using an exogenously introduced donor template (Hendel et al., *Trends in Biotechnology* 33, 132-140 (2015). A recent major addition to this technology is the clustered regularly interspaced palindromic repeat (CRISPR)/Cas system consisting of an RNA-guided nuclease (Cas) and a short guide RNA (sgRNA) Jinek, M. et al., Science 337, 816-821 (2012), Mali, P. et al., Science 339, 823-826 (2013), Cong, L. et al., Science 339, 819-823 (2013), Hsu et al., Cell 157, 1262-1278 (2014)). The guide RNA is composed of two RNAs termed CRISPR RNA (crRNA) and trans-activating crRNA (tracrRNA), which for gene editing purposes are typically fused in a chimeric single guide RNA (sgRNA). The sgRNAs consist of 100 nucleotides (nt) of which 20 nt at the 5' end can hybridize to a target DNA sequence by means of Watson-Crick base pairing and guide the Cas endonuclease to cleave the target genomic DNA (FIG. 1A). The sgRNA can be delivered into cells as RNA, e.g. prepared by in vitro transcription, or by using a DNA vector with the sgRNA expressed from an RNA polymerase III promoter. While genome editing using the CRISPR/Cas system is highly efficient in human cell lines, CRISPR/Cas genome editing in primary human cells is generally more challenging. The reasons for this decreased activity remain elusive, but contributing factors may involve differences in transfection rates, promoter activity, exonuclease activity, innate interferon immune response when delivering nucleic acids, and DNA repair fidelity. Here we demonstrate that chemically synthesized sgRNAs can induce high levels of genome editing and further show that chemical alterations of the sgRNAs can dramatically enhance genome editing in both human primary T cells and CD34+ hematopoietic stem and progenitor cells (HSPCs). The increase in genome editing in these cell types using chemically modified sgRNAs is further improved by delivering Cas9 as mRNA or protein rather than through a DNA expression plasmid, thus generating a simple and complete RNA or ribonucleoprotein (RNP)-based delivery system for the CRISPR/Cas system.

Results

Figure 1B:
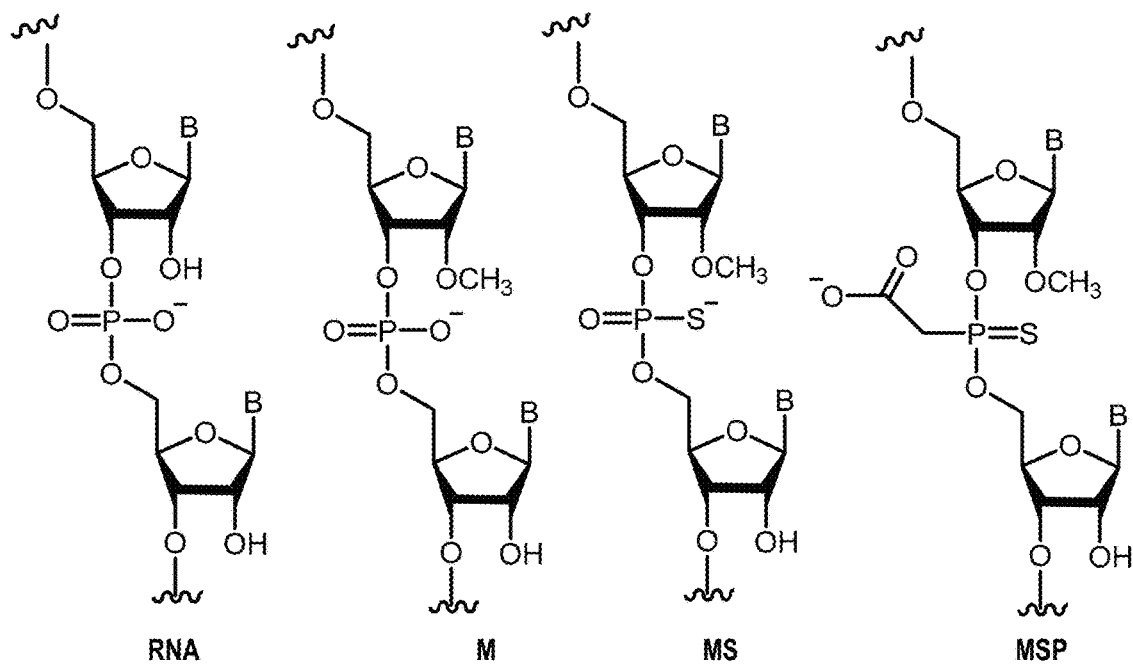
Figure 3:
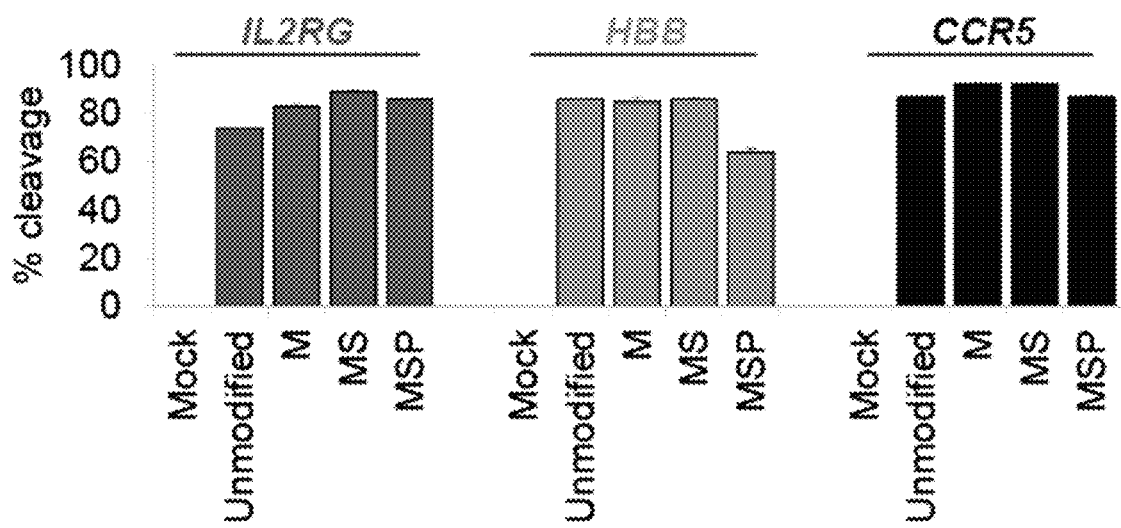
FIG. 3 shows Cas9 cleavage of dsDNA targets directed by chemically modified sgRNAs in vitro. Bars indicate percent yield of cleavage products of target DNA fragments (see, FIG. 4) treated with Cas9 protein and sgRNA. Average values +SEM for three independent syntheses of each sgRNA are shown.
Figure 4:
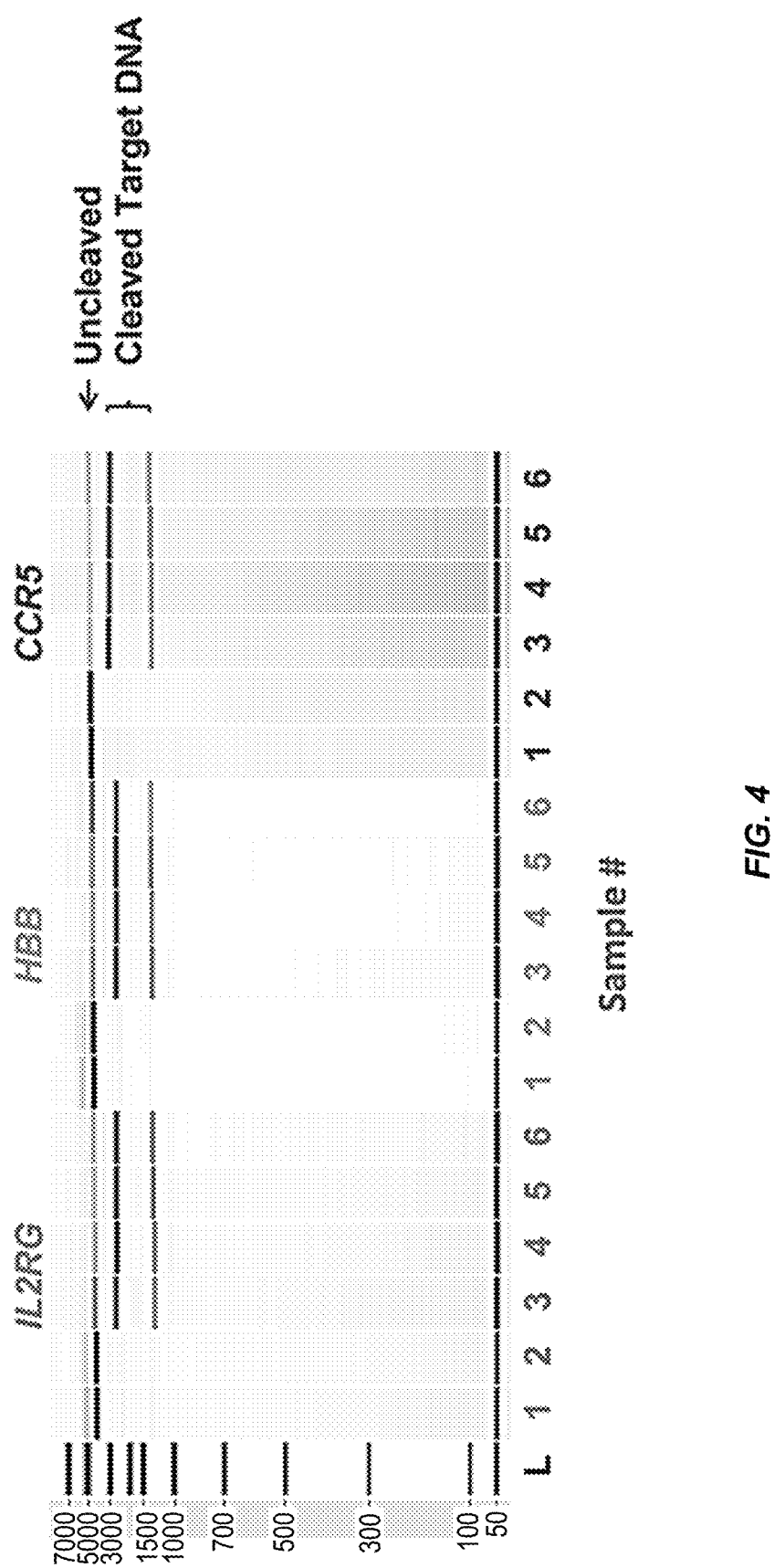
FIG. 4 shows Cas9 cleavage of dsDNA targets directed by chemically modified sgRNAs in vitro. Cleavage products from biochemical cleavage of dsDNA targets were assayed on DNA 7500 LabChips on a Bioanalyzer 2200. Representative gels are shown for each target, and additional replicates are included in the results plotted in FIG. 3. The samples were as follows: (L): ladder, (1): Unmodified sgRNA+target DNA (–Cas9 mock treated), (2): Target DNA+Cas9 protein (–sgRNA mock treated), (3): Unmodified sgRNA+arget DNA+Cas9 protein, (4): M sgRNA+target DNA+Cas9 protein, (5): MS sgRNA+target DNA+Cas9 protein, and (6): MSP sgRNA+target DNA+Cas9 protein.

A recent advancement in RNA synthesis technology made it practical to chemically synthesize RNAs of more than 100 nt in length (Dellinger, D. J. et al., Journal of the American Chemical Society 133, 11540-11556 (2011)). To test the utility of chemically synthesized sgRNAs for genome editing, we synthesized full-length sgRNAs of 100 nt using an ABI 394 synthesizer and 2'-O-thionocarbamate-protected nucleoside phosphoramidites according to previously described procedures (Dellinger, D. J. et al., Journal of the American Chemical Society 133, 11540-11556 (2011)). We also synthesized sgRNAs with a variety of chemical modifications at both termini to evaluate their effects on efficacy (FIGS. 1A and 1B, and Table 1). When present, chemical modifications comprising 2'-O-methyl (M), 2'-O-methyl 3'phosphorothioate (MS), or 2'-O-methyl 3'thioPACE (MSP) were incorporated at three terminal nucleotides at both 5' and 3' ends. These three modifications were selected for evaluation due to their previously reported stability to serum and snake venom phosphordiesterases as well as their wide range of reported effects on the immunostimulatory properties of nucleic acids (Deleavey, G. F. & Damha, M. J., Journal of the American Chemical Society 125, 940-950 (2003), Hendel et al., Cell Reports 7, 293-305 (2014)). We selected three sgRNAs previously reported to yield high gene editing rates in cell lines of each of the following human genes (Hendel et al., Cell Reports 7, 293-305 (2014), Cradick et al., Nucleic Acids Research 41, 9584-9592 (2013)): (i) IL2RG, mutations in which are responsible for the congenital primary immunodeficiency SCID-X1, (ii) HBB, mutations in which are responsible for sickle cell anemia and thalassemia, and (iii) CCR5, which encodes a co-receptor of HIV and is currently being investigated as a target for therapeutic gene editing in anti-HIV clinical trials (Tebas, P. et al., The New England Journal of Medicine 370, 901-910 (2014)). We first tested target DNA cleavage in the presence of purified recombinant Cas9 protein and each of the synthetic sgRNAs in vitro. All chemically synthesized and modified sgRNAs cleaved their DNA targets efficiently in the presence of Cas9 protein (FIGS. 3 and 4).

Figure 1C:
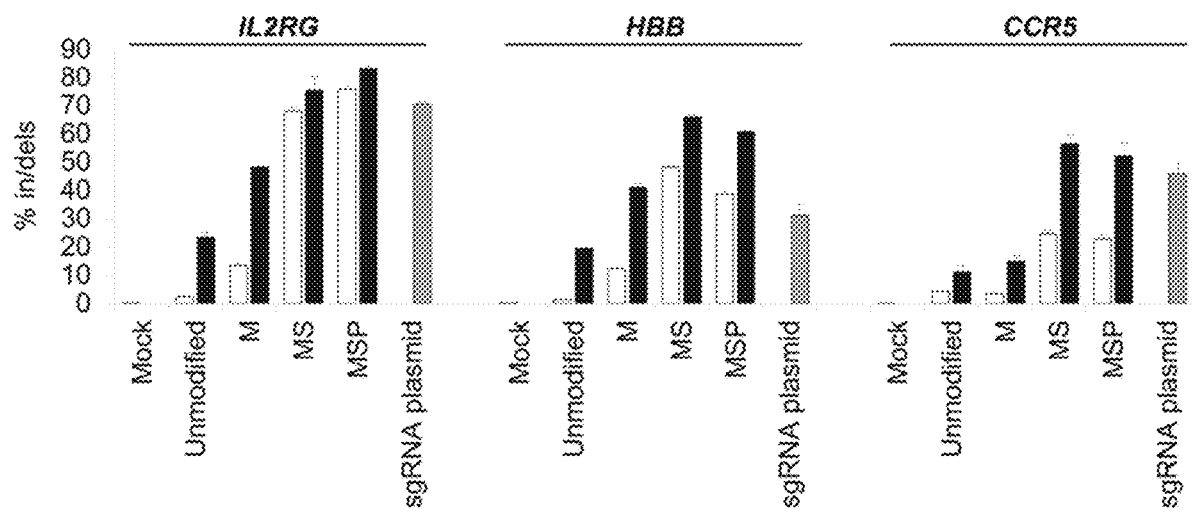
Figure 1D:
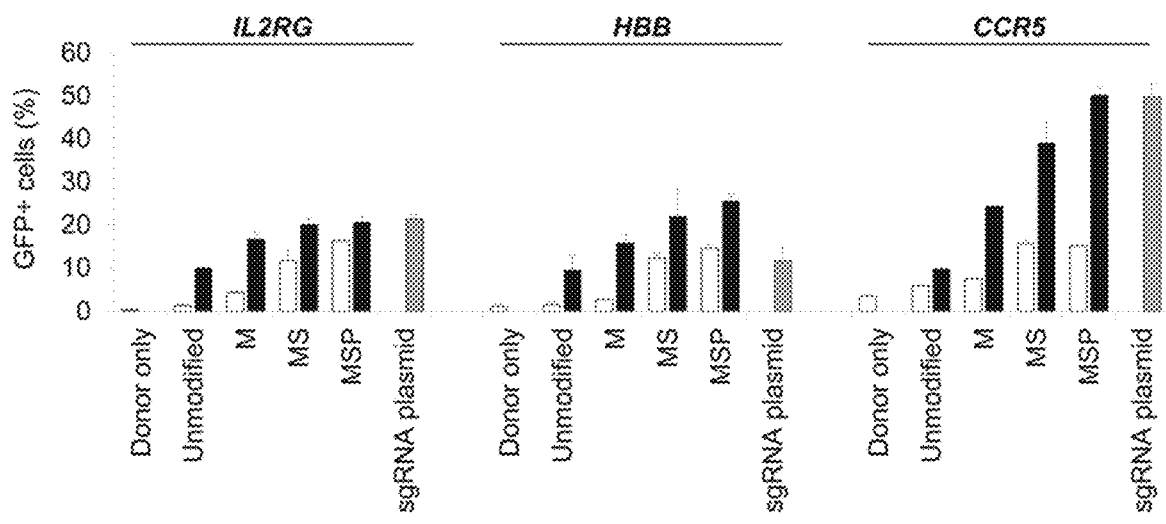

We next examined whether the synthesized sgRNAs could induce targeted in/dels indicative of mutagenic NHEJ and gene disruption in human cell lines. We delivered each sgRNA together with DNA plasmid encoding Cas9 into K562 cells by nucleofection and analyzed in/del frequencies. Delivery of 1 µg of synthetic unmodified sgRNA targeting the IL2RG locus generated targeted in/del frequencies of 2.4% demonstrating its functionality (FIG. 1c, light shade bars). For the M modified sgRNA we observed a small increase in in/del frequencies to 13.5% suggesting a modest improvement in stability over the unmodified sgRNA. Strikingly, the same amount of chemically modified sgRNAs increased the in/del frequency to 68.0% and 75.7% for the MS and for the MSP modified sgRNAs, respectively. Increasing the amount of modified sgRNAs by 20-fold further increased the in/del frequency in all cases, bringing the MS and MSP sgRNAs to 75.3% and 83.3%, respectively (FIG. 1C, dark shade bars), which was comparable to frequencies obtained by expressing the CRISPR/Cas system from a plasmid. Very similar results were obtained for the HBB and CCR5 targets (FIG. 1C), demonstrating the general ability of chemically modified sgRNAs to direct high levels of targeted gene mutations in human cells. We next determined whether these synthetic sgRNAs could stimulate gene targeting via HR. We designed targeting vectors for each of the three loci with ~0.8 kb arms of homology 5' and 3' of the CRISPR cut site. Between the homology arms, we included a GFP expression cassette that can be stably integrated upon successful HR at the targeted locus (Lombard. et al., Nature Methods, 8, 861-869 (2011); Voit et al., Nucleic Acids Research 42, 1365-1378 (2014)). At all three targeted loci, the MS and MSP sgRNAs stimulated significantly higher levels of HR than the unmodified and M modified sgRNAs (FIG. 1D). At higher sgRNA levels (20 µg) we measured HR rates of 20.6%, 25.5%, and 50.0% for the MSP sgRNAs at IL2RG, HBB, and CCR5, respectively. These frequences are comparable to or higher than those obtained by expressing the CRISPR/Cas system entirely from a plasmid.

Figure 1E:
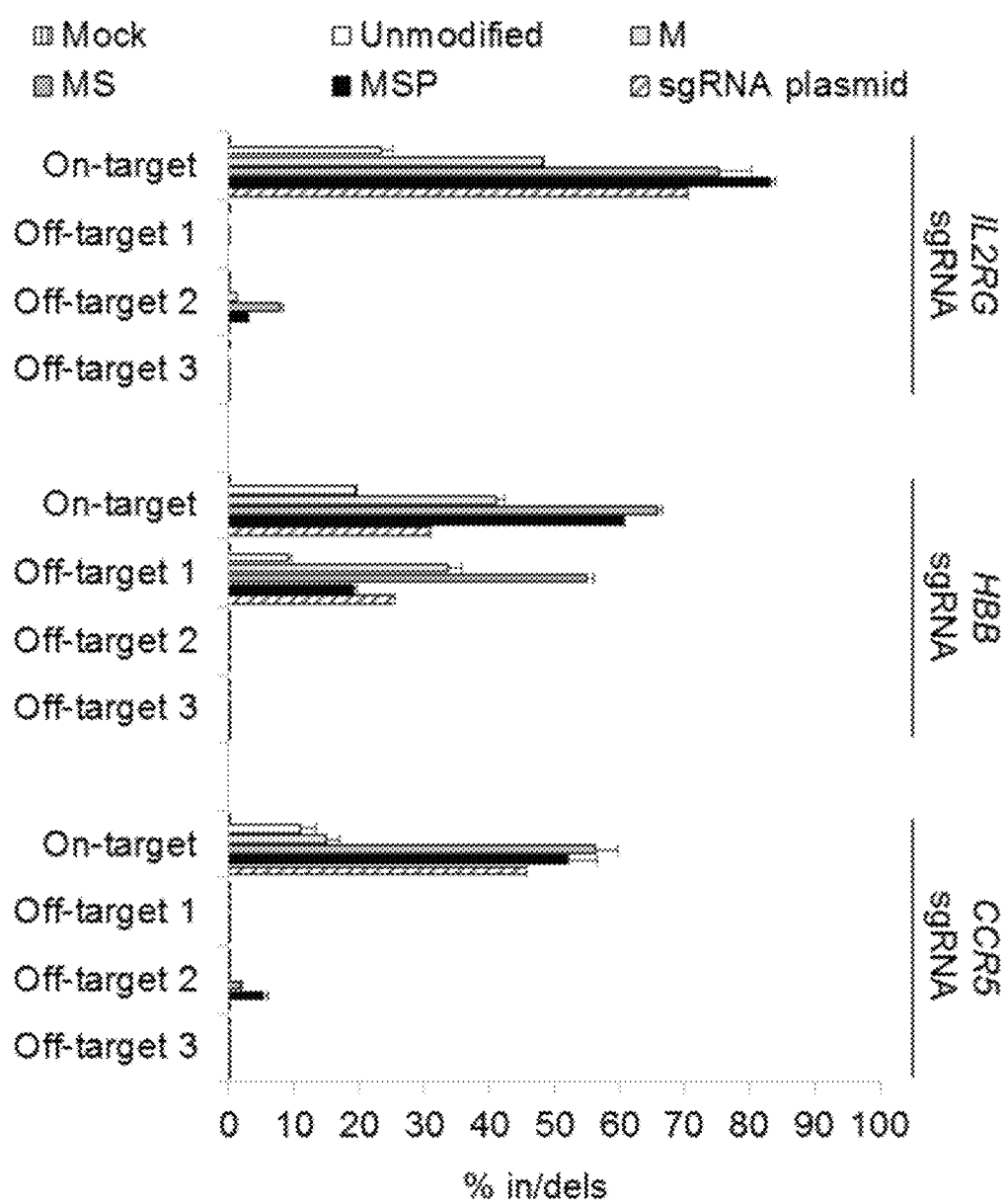
Figure 5:
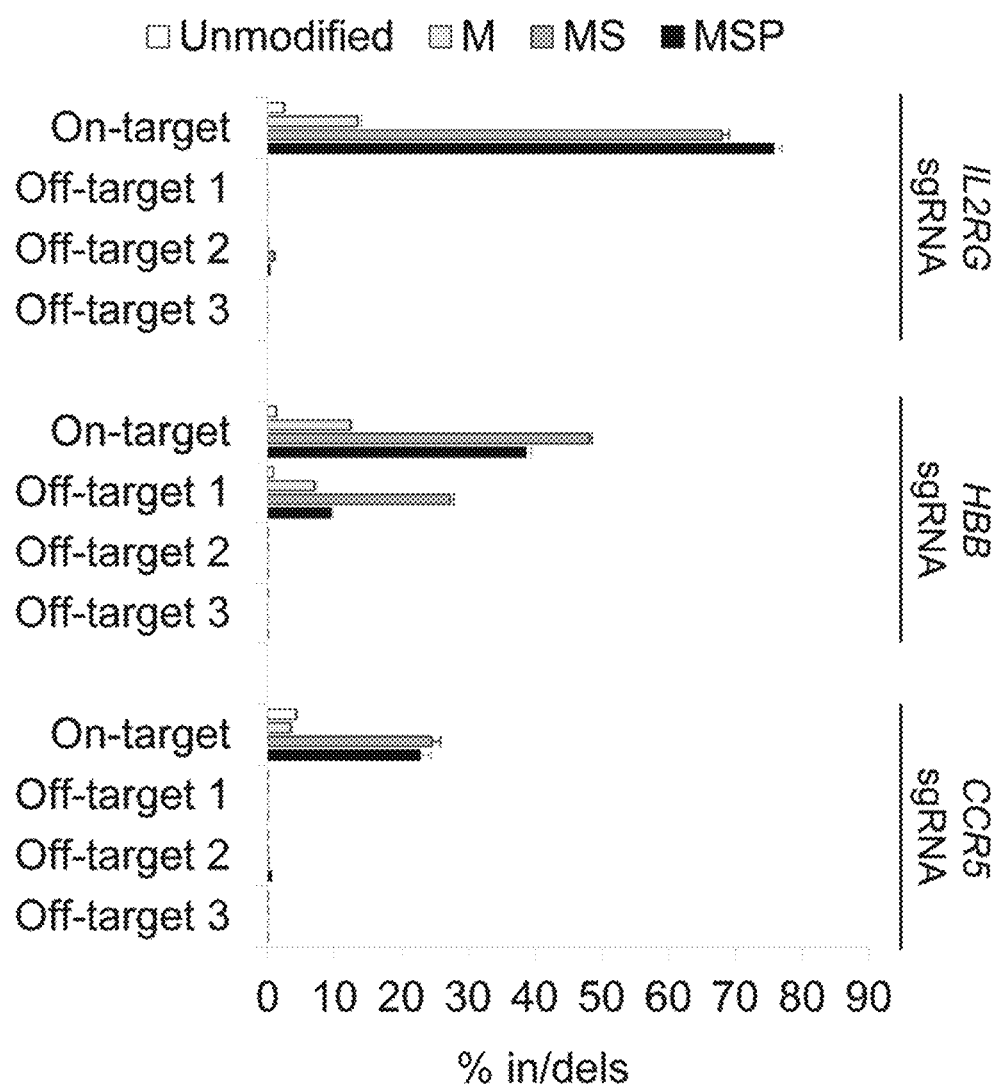
FIG. 5 illustrates the specificity of targeted cleavage mediated by synthetic sgRNAs. Target specificity was assessed as in FIG. 1E using Illumina deep sequencing, but with the samples from FIG. 1C nucleofected with 1 μg sgRNA. In/del frequencies were measured by deep sequencing of PCR amplicons from the three bioinformatically predicted off-target loci for each sgRNA. Bars represent average values +SEM, n=3, displayed on a logarithmic scale. See, Table 5 with the in/del percentages.

To investigate whether chemically modified sgRNAs affect off-target activity, we used deep sequencing to measure off-target mutation frequencies at three different loci for each sgRNA. Eight of these off-target sites were predicted by in silico prediction tools (Hsu et al., Nature Biotechnology 31, 827-832 (2013), Cradick et al., Molecular therapy. Nucleic acids, 3, e214 (2014)), and for the HBB sgRNA we included one off-target site for which the sgRNA has previously shown to have high levels of off-target activity (Cradick et al., Nucleic Acid Research, 42, 9584-9592, (2013)). For four of the eight predicted sites, we found near-background off-target activity for all chemically synthesized sgRNAs despite detecting high levels of on-target activity for the modified sgRNAs (FIGS. 1E and 5, Table 5). Chemical modification of the sgRNAs tended to result in higher off-target activity at the other four predicted sites but the levels of activity were variable. In some cases, the ratio of on-target to off-target in/del frequencies was improved with the modified sgRNAs suggesting an improved relative specificity. The details of these conclusions are summarized below. We only detected activity for the unmodified sgRNA at two off-target sites (IL2RG 'off-target 2' and HBB 'off-target 1' at which the HBB sgRNA has previously demonstrated significant off-target activity), which allowed us to compare on:off-target ratios between unmodified and modified sgRNAs. At the IL2RG site the on:off-target ratio was 5.8-fold better for the unmodified sgRNA compared to the MSP sgRNA (FIG. 1E and Table 5), whereas for the HBB site this ratio was 2.6-fold and 1.5-fold better (for 1 µg and 20 µg) for the MSP sgRNA compared to the unmodified sgRNA (FIGS. 1E and 5, Table 5). Comparing the on:off-target ratios of the modified sgRNAs to on:off-target ratios of the sgRNA plasmid, the sgRNA plasmid had a better ratio at CCR5 'off-target 2' and the IL2RG 'off-target 2', whereas for the HBB 'off-target 1' the MSP sgRNA had the better on:off-target ratio (FIG. 1E and Table 5). Except for the HBB off-target 1 site, the highest off-target frequencies measured were with the IL2RG sgRNAs at 'off-target 2' yielding in/del frequencies of 1.0% and 7.8% when using 1 μg and 20 μg MS sgRNA, respectively. Interestingly, the off-target activity of the IL2RG MSP sgRNA at the same site was 2.7-fold and 2.8-fold lower, respectively, compared to the MS sgRNA, despite having higher on-target activity. Likewise, the off-target activity of the MSP sgRNA was better compared to the MS sgRNA at the HBB off-target-1 site, at which the HBB sgRNA has previously demonstrated significant off-target activity. At the CCR5 'off-target 2' the opposite was observed, the MSP sgRNA had higher off-target activity compared to the MS sgRNA. Taken together, these results suggest that typically the chemically modified sgRNAs retain high specificity. The differences observed in on:off target ratios suggest the possibility that chemical alterations to the sgRNA may have the potential to modulate the on:off-target activities however, the impact of a given chemical alteration appears to be sequence-dependent and may also depend on other factors such as cell type and delivery conditions. Whether these observations are generalizable to other sgRNAs targeting different loci in different species will require further studies.

Figure 1F:
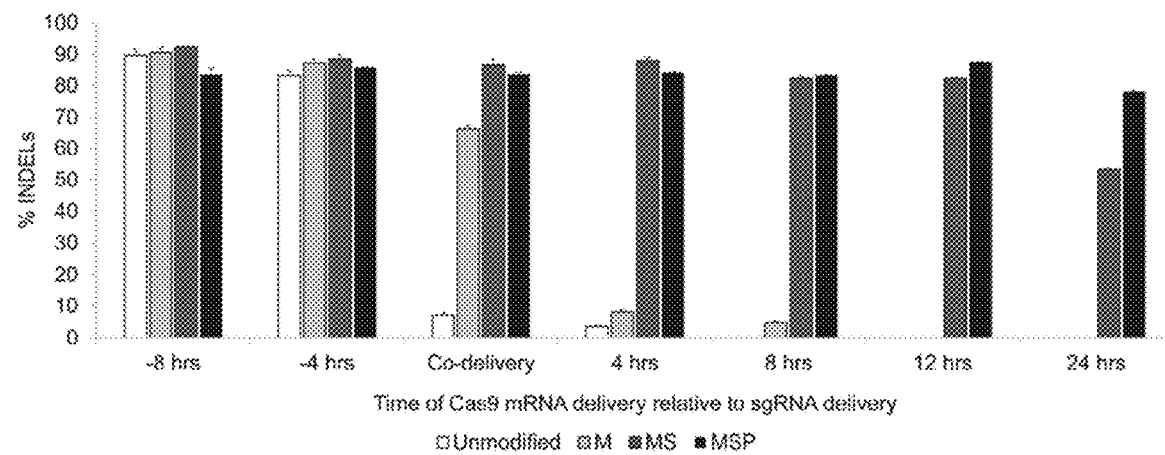
Figure 1G:
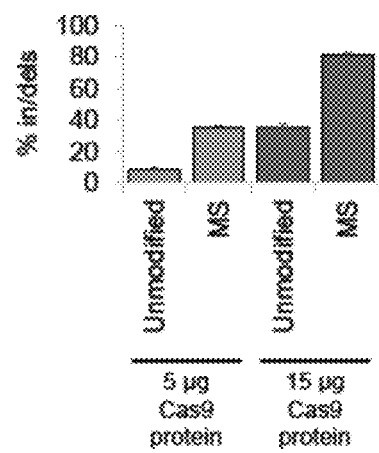
Figure 7:
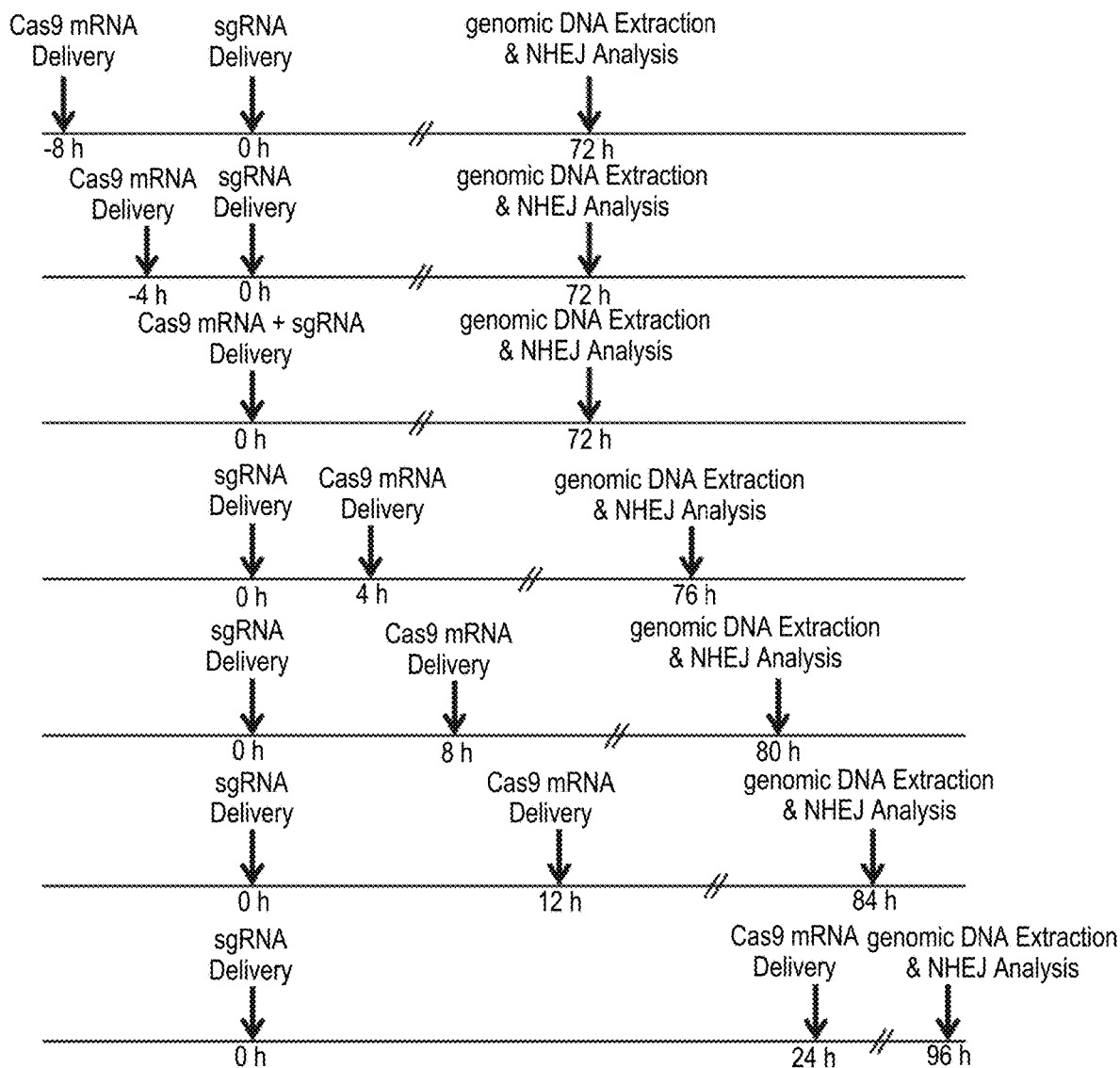
FIG. 7 provides a schematic experimental outline of staggered delivery of sgRNA and Cas9 mRNA. Schematic overview of the experiment yielding data for FIG. 1G. K562 cells were nucleofected at the indicated time points with Cas9 mRNA and/or sgRNAs targeting IL2RG. Genomic DNA was extracted 72 hrs after nucleofection of the last component and in/del frequencies were measured by TIDE using a mock-treated sample as a reference control.
Figure 8:
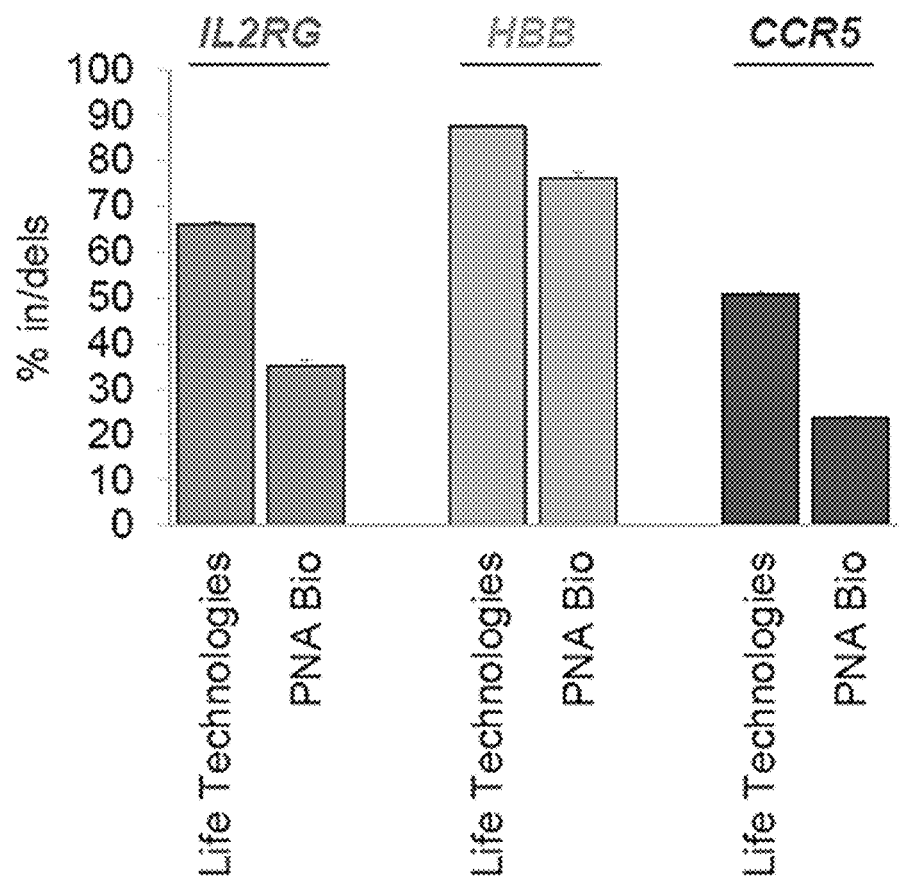
FIG. 8 compares Cas9 protein from different vendors. Three days after 1 million K562 cells were nucleofected with 15 µg Cas9 protein pre-complexed with a 2.5 molar excess of MS sgRNA, genomic DNA was extracted and in/del frequencies were measured by TIDE using a mock-treated sample as a reference control. Bars represent averages +SEM, n=3.
Figure 9B:
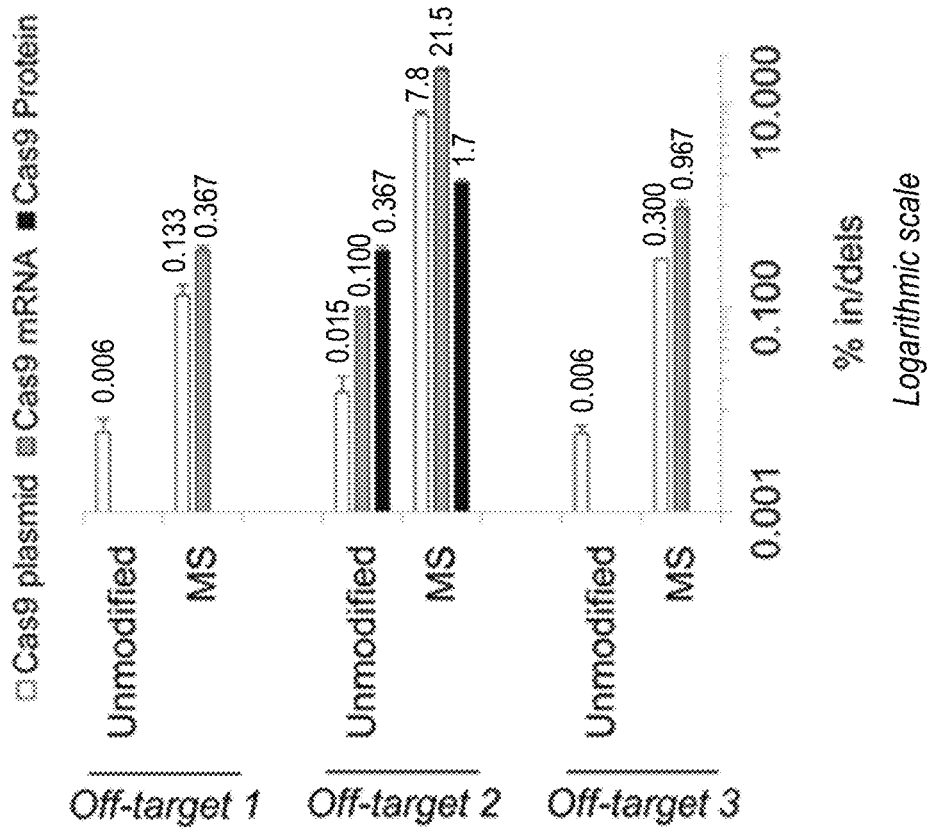
FIGS. 9A-9B show that specificity of targeted cleavage is mediated by synthetic IL2RG sgRNAs and Cas9 plasmid, mRNA, or protein. Target specificity was assessed as in FIG. 1E and FIG. 5 using Illumina deep sequencing and displayed on a linear scale (FIG. 9A) and logarithmic scale (FIG. 9B). 1 million K562 cells were nucleofected with (i) 2 µg Cas9 plasmid+20 µg sgRNA, (ii) 15 µg Cas9 mRNA+10 µg sgRNA, or (iii) 15 µg Cas9 protein pre-complexed with 7.6 µg sgRNA (protein:sgRNA molar ratio=1:2.5). Cas9 plasmid results are the same as shown in FIG. 1E. Bars represent average in/del frequencies +SEM, n=3.
Figure 9A:
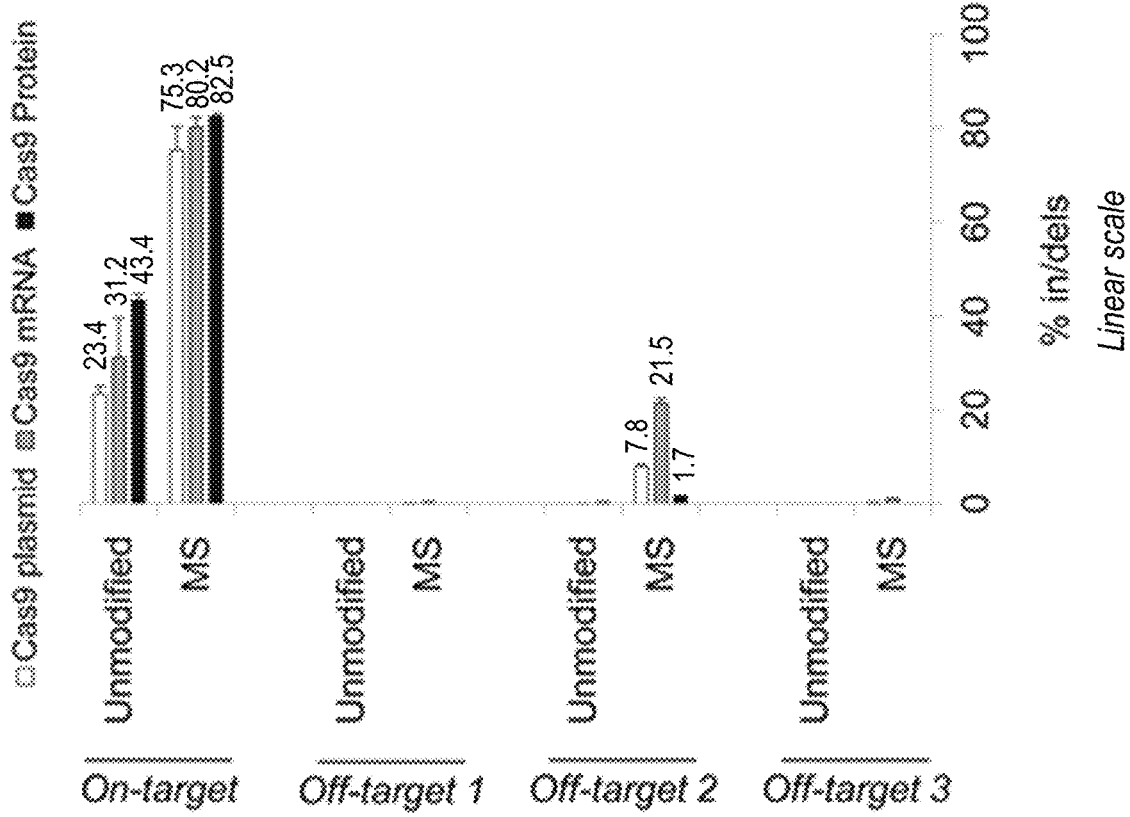

To further explore the performance of chemically modified sgRNAs in human cell lines, we turned to an 'all RNA' delivery platform co-delivering the sgRNAs with mRNA encoding Cas9. We measured in/del frequencies at the IL2RG locus using varying amounts of Cas9 mRNA (1-15 μg) together with varying amounts of the MSP sgRNA (1-20 μg) (FIG. 6). We observed similarly high rates of in/dels between 81-90% for all concentrations tested except for a modest decrease to 70% in/dels when using 1 μg each of the Cas9 mRNA and MSP sgRNA, demonstrating the high efficiency of this 'all RNA' approach. To explore whether the chemical modifications had an effect on the half-life of the sgRNA activity, we performed an experiment in which we either co-delivered or sequentially delivered Cas9 mRNA and the various synthesized sgRNAs targeting IL2RG by nucleofection (FIG. 7). Co-delivery of Cas9 mRNA and either the MS or MSP sgRNA resulted in high editing frequencies of 87% and 84% in/dels, respectively (FIG. 1F). While the M sgRNA gave rise to 66% in/dels, the unmodified sgRNA gave rise to a modest 7.0% clearly signifying the importance of the sgRNA modifications when co-delivered with Cas9 mRNA. Interestingly, delivery of Cas9 mRNA first and the sgRNAs 4 or 8 hours later produced high and comparable levels of in/dels (83.1%-92.4%) across all four sgRNAs with no difference in efficiencies between the unmodified and chemically modified sgRNAs (FIG. 1F). In contrast, when delivering the sgRNA first followed by delivery of Cas9 mRNA 4, 8, 12, or 24 hrs later, in/del frequencies obtained with the unmodified sgRNA dropped to near-background levels already by the 4-hr time point. For the M sgRNA we also observed a decrease in in/del frequencies to near-background levels, but this drop was slightly delayed suggesting a modest improvement in stability over the unmodified sgRNA. For the MS sgRNA, we did not observe a decrease in in/del frequencies until the 24-hr time point, at which rates dropped to 53%. Strikingly, for the MSP sgRNA we did not detect a significant decline in activity even after a 24-hr delay between sgRNA and Cas9 delivery. These results are consistent with our model in which sgRNA end-modifications enhance intracellular stability, thus enabling increased efficacy of genome editing when Cas9 mRNA and sgRNAs are co-delivered into human cells. The fact that in/del frequencies directed by the unmodified sgRNA were not reduced when Cas9 was delivered first, suggests that Cas9 protein protects sgRNAs from degradation. To investigate this hypothesis we complexed the unmodified or the MS IL2RG sgRNA with recombinant Cas9 protein before electroporating this active RNP into K562 cells at two different amounts (FIGS. 1G and 8). With the low amount of RNP, we observed 3.8-fold higher in/del frequencies when using the MS sgRNA compared to the unmodified sgRNA (35.7% vs. 9.5%), and for the high amount of RNP this increase was 2.3-fold (81.0% vs. 35.9%). This ratio between MS and unmodified sgRNA was, however, significantly less than that observed when co-delivering the sgRNAs with Cas9 mRNA (compare to FIG. 1F 'Co-delivery'), indicating that the Cas9 protein does partially protect the unmodified sgRNA from degradation. Nonetheless, modifications to the sgRNA still improve gene editing efficiencies when delivering the sgRNA pre-complexed with Cas9 protein. Next, we compared the off-target activity of the unmodified and MS IL2RG sgRNAs at the three previously investigated off-target sites when delivered either with Cas9 plasmid, Cas9 mRNA, or pre-complexed with Cas9 protein. With the unmodified sgRNA we detected low levels of in/dels (<0.37%) across all three Cas9 sources and all three off-target sites (FIGS. 9A-B). For the MS sgRNA, we observed improved on:off-target ratios at all three off-target sites when delivering Cas9 plasmid compared to Cas9 mRNA (2.6-3.0-fold). Notably, for Cas9 RNP delivery with MS sgRNA we detected significantly better on:off-target ratios compared to Cas9 plasmid and mRNA for all three sites, with near-background off-target activity at two of the sites. In sum, the chemically modified sgRNAs demonstrate a significant advantage over the unmodified sgRNA for gene editing in human cell lines when co-delivered with Cas9 mRNA or delivered as RNP.

Figure 2A:
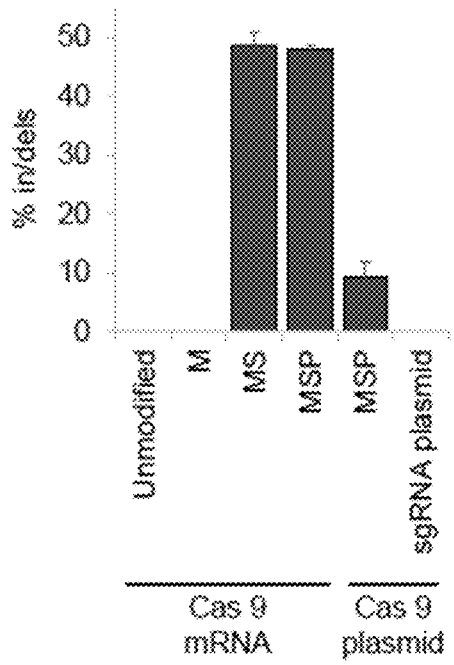
FIGS. 2A-2C show that chemically modified sgRNAs facilitate high rates of gene disruption in primary human T cells and CD34+ hematopoietic stem and progenitor cells (HSPCs). 1 million primary human T cells were nucleofected with 10 μg of the indicated synthetic sgRNAs and either 15 μg Cas9 mRNA or 1 μg Cas9-encoding plasmid (FIG. 2A). 1 plasmid encoding both the sgRNA and Cas9 protein was included for comparison. Bars represent average in/del frequencies for three different donors +SEM, n=6 as measured by TIDE analysis of PCR amplicons spanning the sgRNA target sites, and using a mock-treatment sample as a reference control.
Figure 2B:
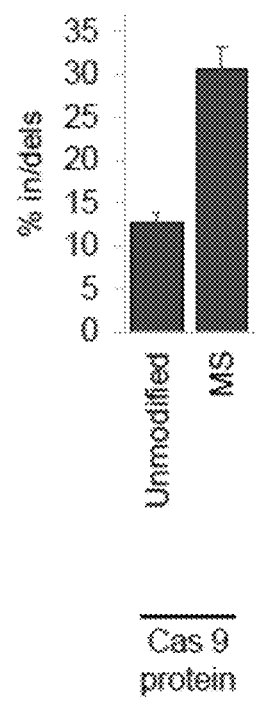
Figure 10:
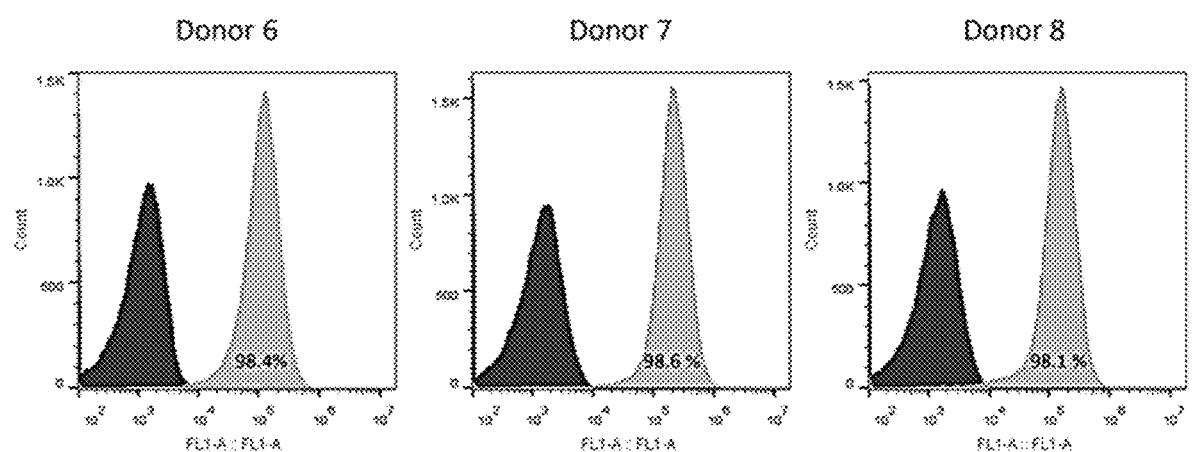
FIG. 10 shows high RNA nucleofection efficiencies in primary human T cells. Stimulated T cells from three different donors were nucleofected with GFP mRNA three days after stimulation. Expression of GFP was measured three days after nucleofection by flow cytometry. GFP expression in nucleofected cells (grey) is shown relative to mock-transfected cells (black).
Figure 11:
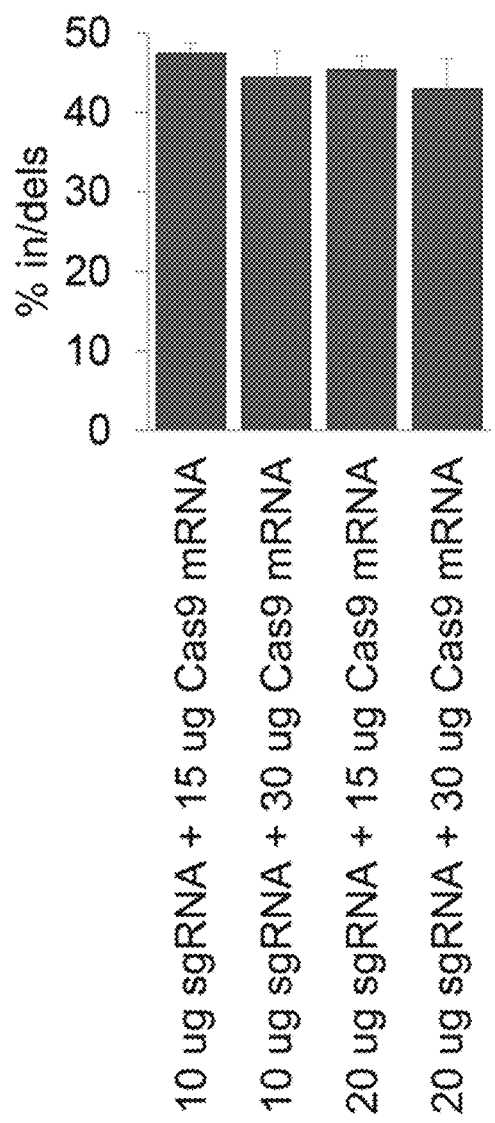
FIG. 11 shows that increasing CCR5 sgRNA and Cas9 mRNA amounts in T cell nucleofection yielded similar in/del frequencies. Stimulated T cells were nucleofected with the indicated amounts of the MSP CCR5 sgRNA and Cas9 mRNA. In/del frequencies were measured by TIDE analysis of PCR amplicons spanning the sgRNA target sites and using a mock-treated sample as a reference control. Average in/del frequencies are shown +SEM, n=6.
Figure 12:
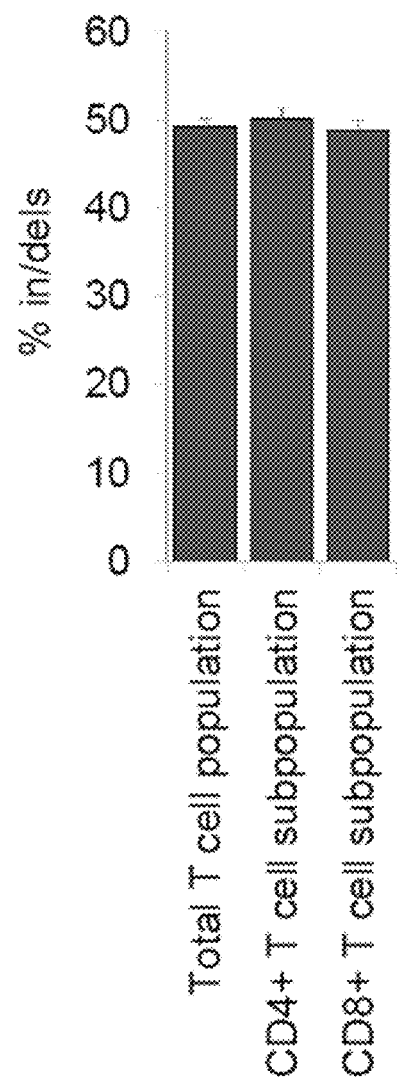
FIG. 12 shows similar in/del frequencies in CD4+, CD8+, and total T cell populations. Stimulated T cells were nucleofected with CCR5 MSP sgRNA and Cas9 mRNA and subsequently sorted into CD4+ and CD8+ subpopulations. In/del frequencies were measured by TIDE and compared to in/del frequencies in the bulk population. Bars represent average in/del frequencies for one T cell donor +SEM, n=8.
Figure 13:
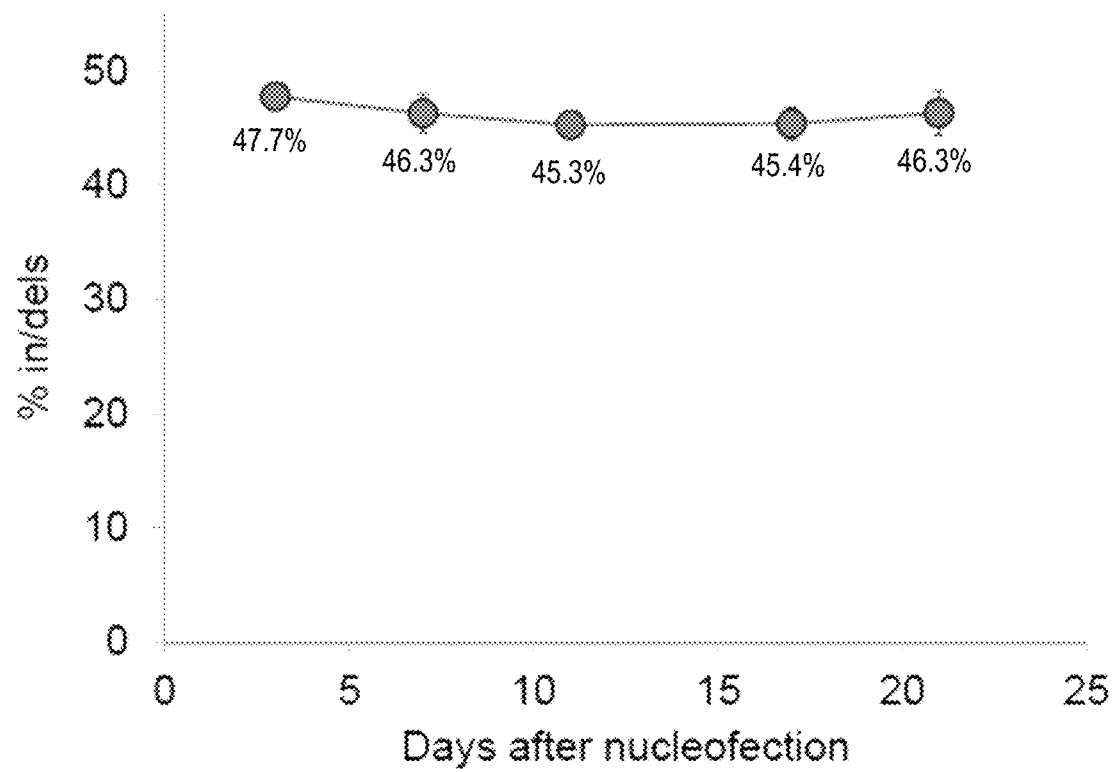
FIG. 13 shows in/del frequencies in primary human T cells are stable over time. Stimulated T cells were nucleofected with the CCR5 MSP sgRNA and Cas9 mRNA. gDNA was extracted from a subset of cells at the indicated time points, and in/del frequencies were measured by TIDE analysis of PCR amplicons spanning the sgRNA target site and using a mock-treated sample as reference control. Average in/del frequencies are shown for three different T cells donors +/−SEM, n=6.
Figure 14:
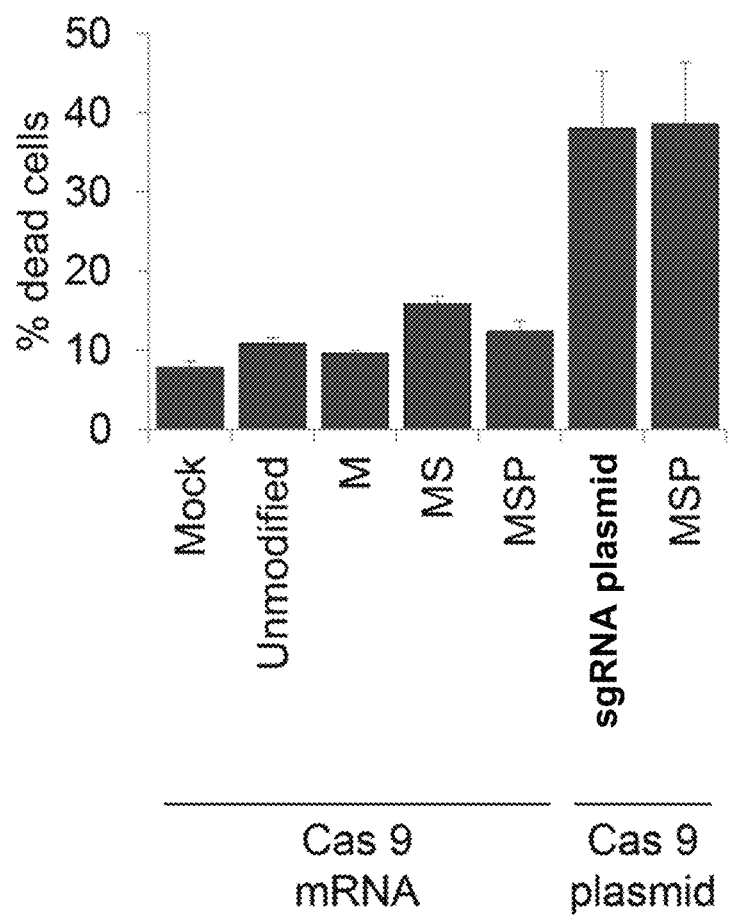
FIG. 14 shows lower frequencies of cell death in T cells nucleofected with synthetic sgRNAs and Cas9 mRNA compared to Cas9 plasmid. 1 million stimulated T cells were nucleofected 10 µg of of the indicated synthetic sgRNAs and either 15 µg Cas9 mRNA or 1 µg Cas9-encoding plasmid. 1 µg of plasmid encoding both the CCR5 sgRNA and Cas9 protein was included for comparison (sgRNA plasmid). Three days after nucleofection, cells were stained with the LIVE/DEAD cell staining. Bars represent average percentages of dead cells for three different T cell donors +SEM, n=6.
Figure 15:
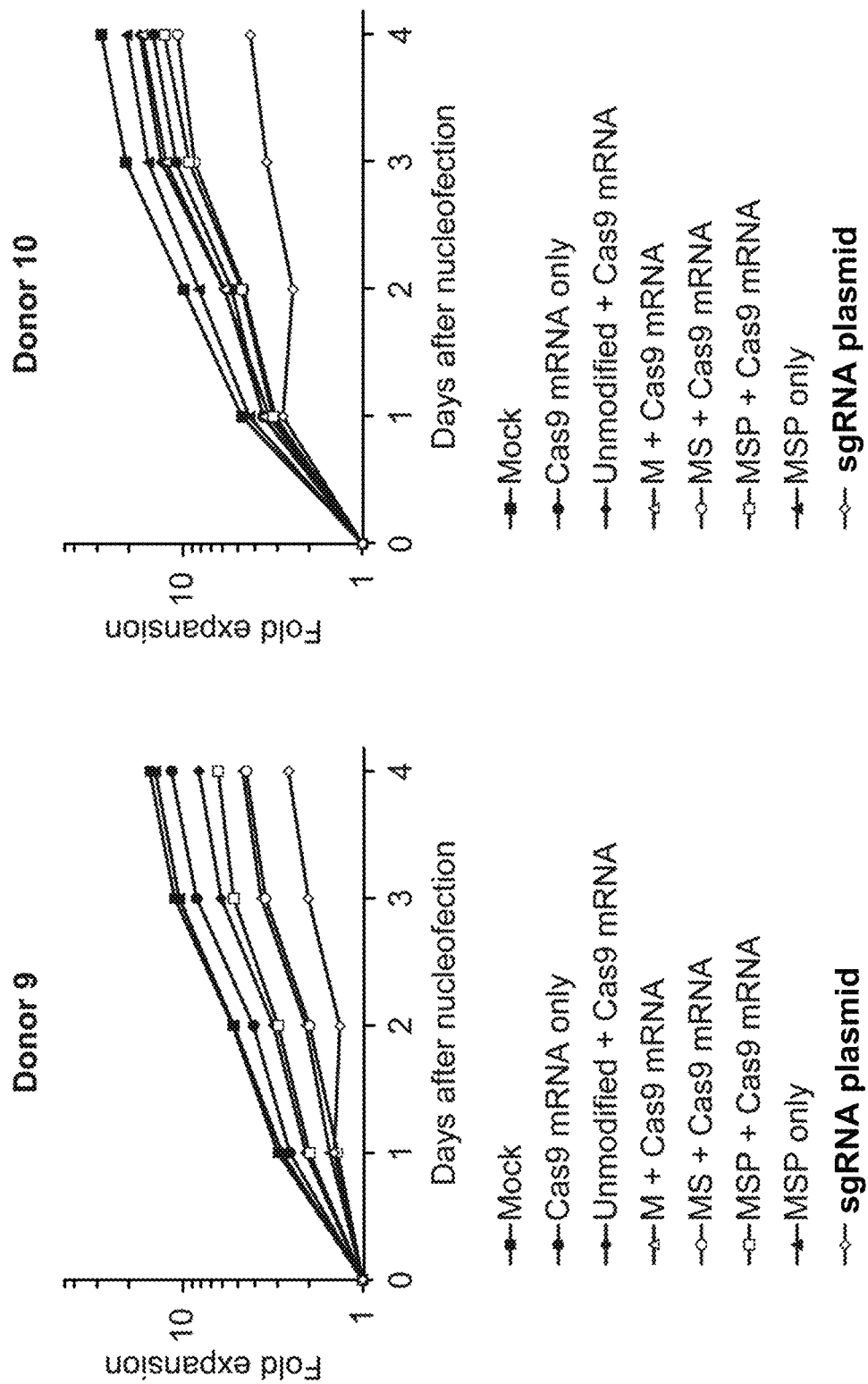
FIG. 15 shows results from a proliferation assay following nucleofection of synthtetic sgRNAs into T cells. Stimulated T cells from two different donors were nucleofected on Day 0, and cell proliferation was monitored using the CellTiter Glo assay. SEM of replicates are not indicated for clarity, but all are less than 15% of the indicated values.
Figure 16:
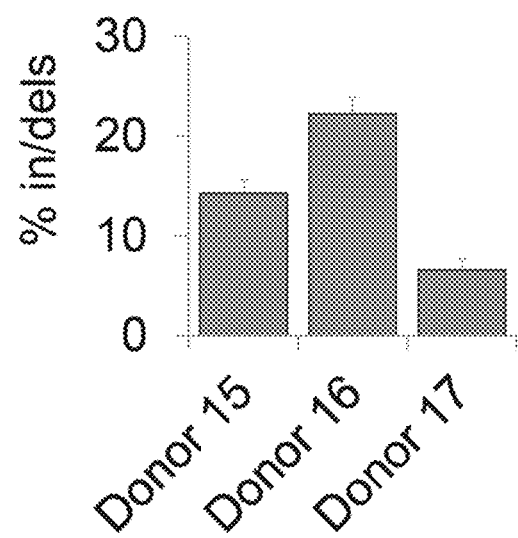
FIG. 16 shows CCR5 disruption in unstimulated T cells. Unstimulated human T cells from three different donors were nucleofected on the day of isolation with the MS sgRNA and Cas9 mRNA. gDNA was extracted three days after nucleofection and in/del frequencies were measured by TIDE using a mock-treated sample as a reference control. Bars represent average +SEM, n=2.

We next tested the chemically modified sgRNAs in primary cells. CCR5 gene disruption using zing-finger nucleases (ZFNs) in CD4+ T cells is currently being explored in clinical trials as an anti-HIV treatment (Tebas et al. *New Eng Jour of Med,* 370, 901-910 (2014)). However, a recent study found that the genome of human primary T cells is inherently difficult to edit with the CRISPR/Cas9 plasmid system using a single sgRNA, and that sgRNAs giving rise to high allele modification frequencies in cell lines have substantially reduced efficacy in T cells, even when enriching for transfected cells (Mandal et al., *Cell Stem Cell,* 15, 643-652 (2014)). We tested the chemically modified CCR5 sgRNAs in stimulated human primary T cells co-delivered with Cas9-encoding mRNA. Of note, using GFP mRNA we consistently observed more than 98% nucleofection efficiencies in T cells as measured by flow cytometry (FIG. 10), obviating the need to enrich for transfected cells. Nucleofection of the sgRNA plasmid encoding both the sgRNA and Cas9 did not give rise to allele modification frequencies above background (FIG. 2A). However, co-transfection of the MSP sgRNA with DNA expression plasmid for Cas9 was able to rescue activity to 9.3% in/del frequencies. Nucleofection of Cas9 mRNA with the unmodified or the M sgRNA did not give rise to allele modification rates above background. In contrast, nucleofection of Cas9 mRNA with either the MS or MSP sgRNA generated remarkable 48.7% and 47.9% in/del frequencies, respectively. Increasing the amounts of sgRNA or Cas9 mRNA did not yield higher in/del frequencies (FIG. 11). For cells nucleofected with Cas9 mRNA and MSP sgRNA we found comparable allele modification frequencies in the CD4+, CD8+, and total T cell populations (FIG. 12). Importantly, the observed high modification frequencies were stable when measured for the MSP sgRNA over a time course of 21 days (FIG. 13), and we only observed small impacts on cell viability and proliferation after nucleofection with the modified sgRNAs, in contrast to plasmid nucleofection, which caused significant cell death and decreased proliferative potential (FIGS. 14 and 15). We also tested the MS sgRNA in unstimulated T cells, which have been shown to be more difficult to edit than stimulated T cells (Yi et al., *Molecular Therapy Nucleic Acids*, 3, e198 (2014)). In contrast to stimulated T cells, in/del frequencies in unstimulated T cells ranged from 6.6% to 22.2%, showing higher donor variability (FIG. 16). While lower than in stimulated T cells, these editing frequencies in unstimulated T cells may still have utility, particularly in engineering T cells in which activation and prolonged culture may affect the subsequent biological functionality of the cells. We next tested RNP delivery using unmodified and MS sgRNAs in stimulated primary T cells (FIG. 2B). Similarly to the results obtained in K562 cells we observed a 2.4-fold improvement in in/del frequencies of the MS sgRNA over the unmodified sgRNA (30.7% vs. 12.8%) further supporting the use of chemically modified sgRNAs when delivered pre-complexed with Cas9 protein.

Figure 2C:
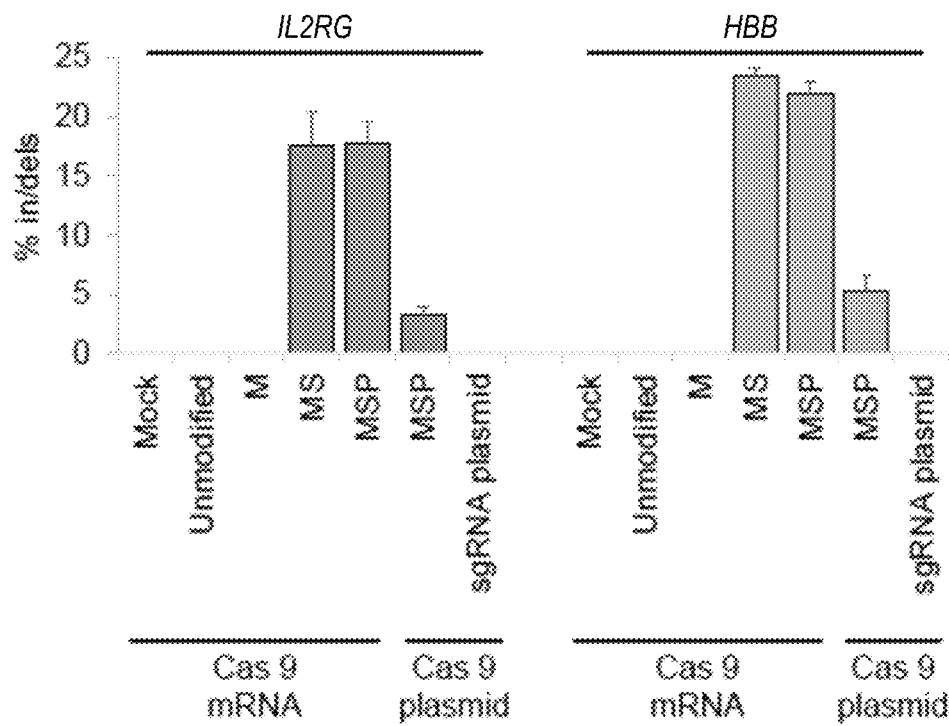
Figure 17:
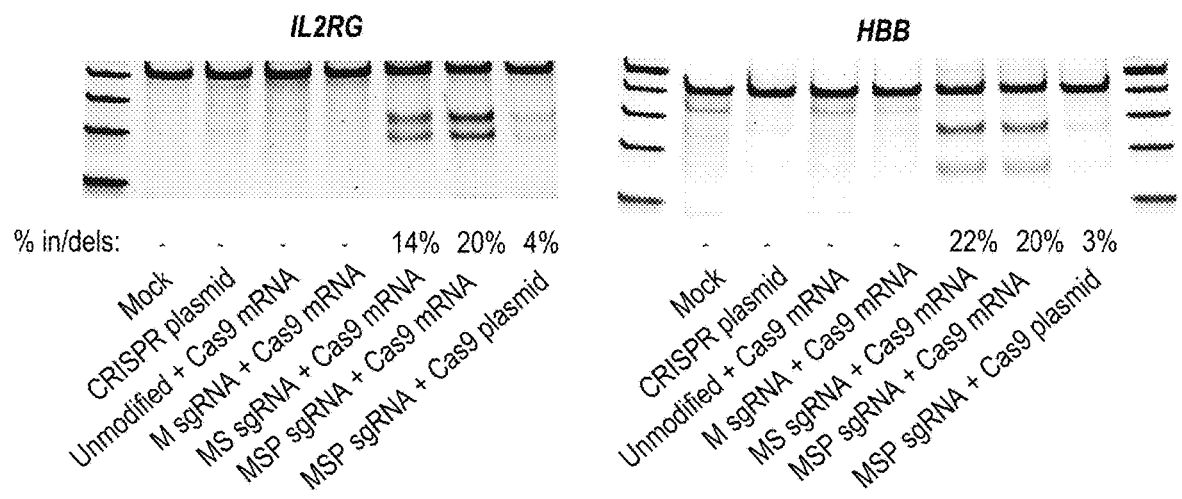
FIG. 17 illustrates in/del frequencies in mobilized PB CD34+ HSPCs for IL2RG and HBB. Three days after nucleofection of CD34+ HSPCs, genomic DNA was extracted and in/del frequencies were measured by the T7 assay. One representative gel of three biological replicates for each of IL2RG and HBB is shown. +SEM, n=2.

Gene therapy in HSPCs has been explored extensively for treating genetic or acquired disorders of the hematopoietic system. We tested whether the chemically modified sgRNAs targeting IL2RG and HBB are functional in CD34+ HSPCs isolated from mobilized peripheral blood. Again, the sgRNA plasmid expressing both sgRNA and Cas9 did not give rise to detectable in/del frequencies, but co-transfection of the MSP sgRNA with the Cas9 DNA expression plasmid rescued in/del frequencies to 3.2% and 5.2% for IL2RG and HBB, respectively (FIGS. 2C and 17). Similar to our observations in T cells, we did not detect in/dels at either loci using the unmodified or M sgRNAs when co-transfected with Cas9 mRNA, but the MS and MSP sgRNAs each gave rise to high in/del frequencies: for IL2RG we detected 17.5% and 17.7% in/del frequencies for the MS and MSP sgRNAs, respectively, and for HBB the frequencies were even higher at 23.4% and 22.0%, respectively. Further studies could elucidate whether genetic modifications of HSPCs by chemically modified sgRNAs affect their multipotency capacity, or if editing efficiencies differ between long-term repopulating stem cells and lineage-committed progenitor cells.

Figure 2D:
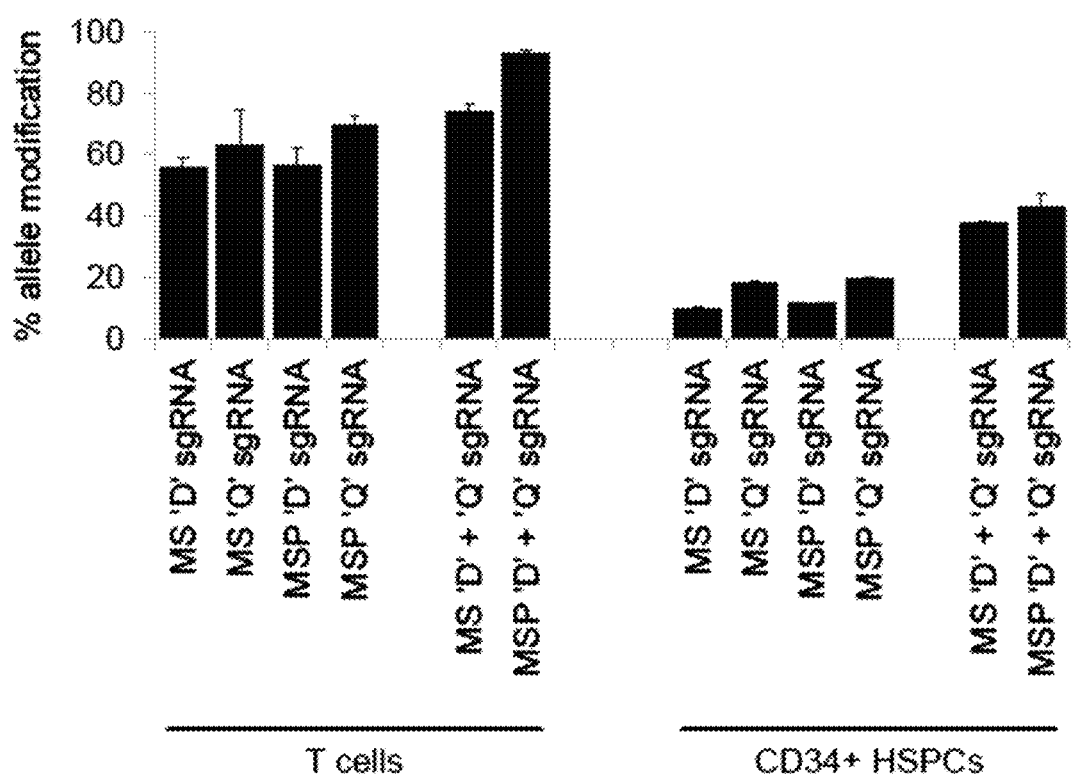
Figures 18A, 18B:
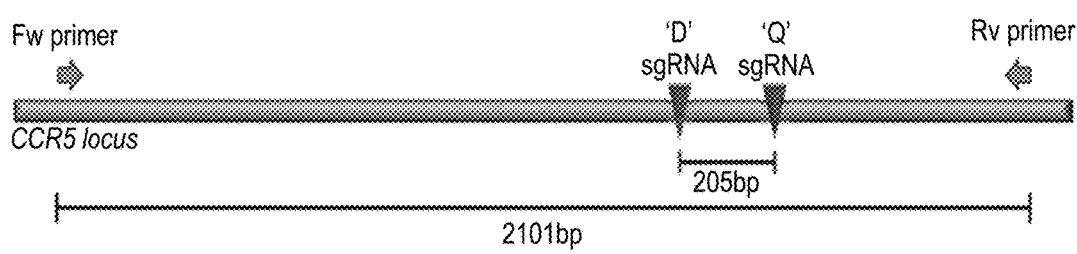
FIGS. 18A-18B show high CCR5 gene modification frequencies in primary human T cells and CD34+ HSPCs using two sgRNAs. Stimulated T cells from three different donors and PB mobilized CD34+ HSPCs were nucleofected in triplicate with both the 'D' and 'Q' sgRNA together with Cas9 mRNA. gDNA was extracted three days after nucleofection and the modified region of CCR5 was PCR-amplified using a pair of primers generating a 2.1 kb amplicon for non-modified alleles (FIG. 18A). PCR amplicons were subcloned into a plasmid for transformation, and individual colonies representing individual alleles were sequenced, referenced against the expected genomic sequence, and categorized according to the allelic genotype (FIG. 18B).

A recent study showed that the simultaneous use of two sgRNAs could improve gene disruption in human primary T cells and in CD34+ HSPCs (Mandal et al., *Cell Stem Cell*, 15, 643-652 (2014)). We chemically synthesized MS and MSP CCR5 sgRNAs having the sequences reported in that study (termed 'D' and 'Q') which cut 205 bp apart. We tested them in T cells and in CD34+ HSPCs co-delivered with Cas9 mRNA. When the two sgRNA were used individually we quantified allele modification frequencies using TIDE analysis. When both were used, we quantified allele modification frequencies by sequencing of cloned PCR products, which also allowed us to quantify the full spectrum of editing events, including the previously reported high incidence of deletions of sequence between the two sgRNA target sites. When used individually in primary T cells the 'D' sgRNA gave rise to 56.0% and 56.3% in/dels for the MS and MSP sgRNA, respectively, and the 'Q' sgRNA gave rise to 62.6% and 69.6%, respectively (FIGS. 2D and 18A). When used in combination, the frequencies of allele modification increased, as we observed 73.9% and 93.1% for the MS and MSP sgRNAs, respectively, of which the majority of the modification events were deletions between the two sgRNA target sites (FIG. 18B). In CD34+ HSPCs our observations were similar though the overall frequencies were lower. Thus, for the 'D' sgRNA we observed 9.8% and 11.2% allele modification frequencies for the MS and MSP sgRNA, respectively, and 17.8% and 19.2% for the 'Q' sgRNA (FIGS. 2D and 18B). When used in combination the frequencies increased to 37.8% and 43.0% for the MS and MSP sgRNAs, respectively. We conclude that the use of two chemically modified sgRNAs is a highly effective way to facilitate gene disruption in primary human T cells and CD34+ HSPCs.

Figure 19:
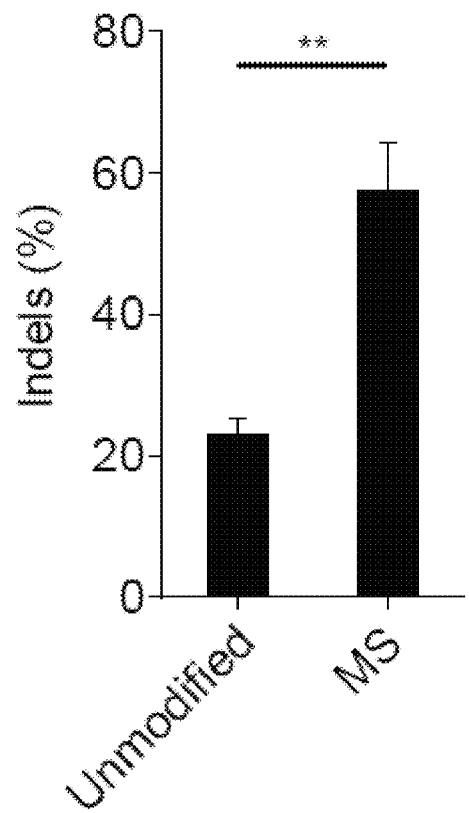
FIG. 19 shows that MS-modified sgRNAs perform better than unmodified sgRNAs in CD34+ HSPCs. CD34+ HSPCs were nucleofected with 30 µg Cas9 protein complexed with a 2.5 molar excess of the indicated synthetic HBB sgRNAs. Indel frequencies were measured by TIDE analysis four days after nucleofection. Bars represent average indel frequencies for three different donors +SEM, n=3. ** $p<0.01$, Student's t test.
Figure 20:
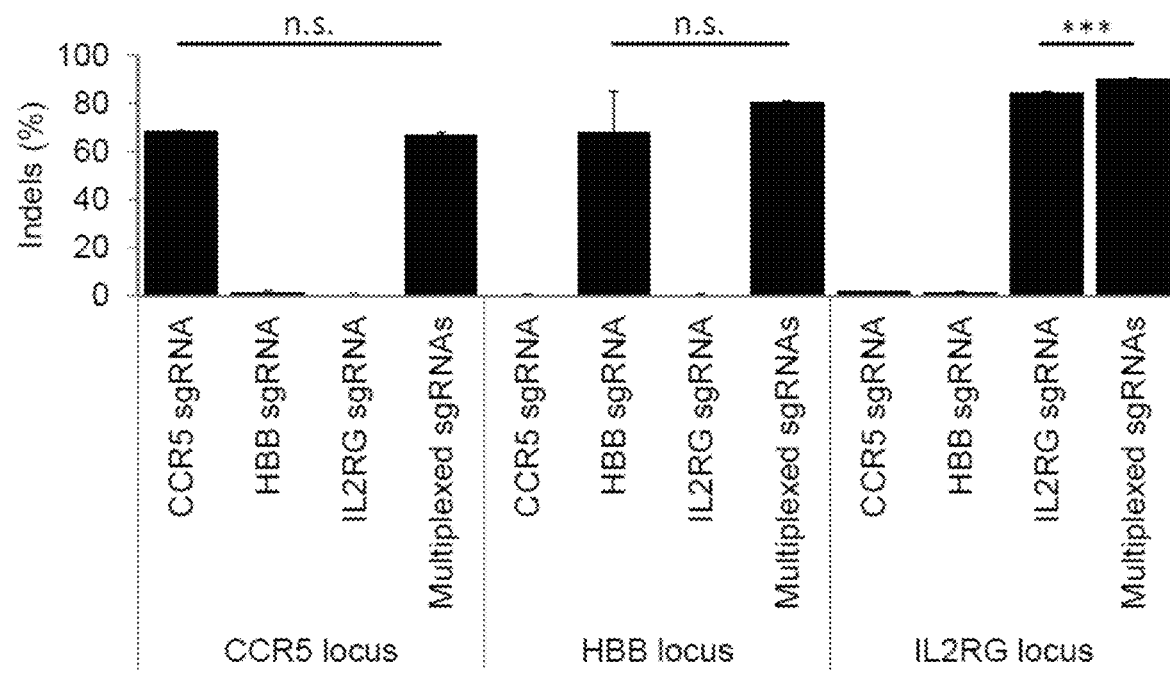
FIG. 20 shows that modified sgRNAs can be used for efficient multiplexed genome editing. 1 million K562 cells were nucleofected with 15 µg Cas9 mRNA and either 5 µg CCR5, HBB, or IL2RG MS-modified sgRNAs or all three sgRNAs (multiplexed) (3×5 µg). Indel frequencies were measured by TIDE analysis at each of the three loci three days after nucleofection. Bars represent average indel frequencies +SEM, n=3. *** $p<0.001$, n.s.=$p≥0.05$, Student's t test.

FIG. 19 provides additional experimental data showing that MS-modified sgRNAs perform better than the corresponding unmodified sgRNAs in CD34+ HSPCs. FIG. 20 shows that modified sgRNAs can be used for efficient multiplexed genome editing.

In this study, we show that chemically synthesized sgRNAs can be used effectively for targeted genome editing and demonstrate that chemically modified sgRNAs significantly enhance genome editing efficiencies in human primary T cells and CD34+ HSPCs. Chemically synthesized and modified sgRNAs offer advantages over expressed or in vitro transcribed sgRNAs, among them: (1) increased efficacy, (2) robust and scalable production of highly pure sgRNAs for biotechnological and therapeutic applications, (3) greater flexibility in the sgRNA design in contrast to constraints on the first transcribed nucleotides imposed by the U6 or T7 promoters, typically used for plasmid expression or in vitro transcription of sgRNAs, respectively and (4) enablement of a highly active 'RNA only' or RNP CRISPR platform with lower cytotoxicity in primary cells than DNA plasmid-based systems. The simplification of the CRISPR/Cas system to a purely RNA or RNP CRISPR system lends itself to formulation in different nanoparticle vectors for delivery in vivo such that the nuclease will not be expressed continuously, as it would be when delivered as part of a viral vector. Furthermore, we anticipate that chemically modified sgRNAs will enhance multiplexed genome editing as well as igh-throughput multi-well experiments. We also anticipate that modified sgRNAs will refine a wide range of CRISPR-associated technologies such as the CRISPRi/CRISPRa systems for inhibition and activation of gene expression (Gilbert, L. A. et al., *Cell* 159, 647-661 (2014)) the CRISPR imaging tool for dynamic visualization of genomic loci (Chen, B. et al., *Cell* 155, 1479-1491 (2013)), and CRISPR-mediated RNA recognition and cleavage (O'Connell, M. R. et al., *Nature* 516, 263-266 (2014)). The technology may be further developed to improve intracellular delivery to target cells or tissues, and enable conjugation to various molecules for imaging, and biochemical studies. Future studies could investigate a larger variety of chemical modifications, explore different locations of the modifications for rational design of optimized sgRNAs, as well as the mechanism for the enhanced activity of modified sgRNAs. In conclusion, we believe chemically modified sgRNAs like those presented here will significantly improve a wide array of CRISPR/Cas biotechnological and therapeutic applications.

Materials and Methods 1. sgRNA Synthesis

All RNA oligomers were synthesized on an ABI 394 Synthesizer (Life Technologies, Carlsbad, Calif., USA) using 2'-O-thionocarbamate-protected nucleoside phosphoramidites (Sigma-Aldrich, St. Louis, Mo., USA or Thermo Fisher, Waltham, Mass., USA) according to previously described procedures (Dellinger et al., *Journal of the American Chemical Society* 133, 11540-11556 (2011)).

2'-O-methyl phosphoramidites were purchased from Thermo Scientific, Grand Island, N.Y., and incorporated into RNA oligomers under the same conditions as the 2'-O-thionocarbamate protected phosphoramidites. The 2'-O-methyl-3'-O-(diisopropylamino)phosphinoacetic acid-1,1-dimethylcyanoethyl ester-5'-O-dmethoxytrityl nucleosides used for synthesis of thiophosphonoacetate (thioPACE) modified RNAs were synthesized essentially according to published methods (Threlfall et al., *Organic & biomolecular chemistry*, 10, 746-754 (2012); Dellinger et al., *Journal of the American Chemical Society*, 125, 940-950 (2003)). For phosphorothioate containing oligomers, the iodine oxidation step after the coupling reaction was replaced by a sulfurization step using a 0.05 M solution of 3-((N,N-dimethylaminomethylidene)amino)-3H-1,2,4-dithiazole-5-thione in a pyridine-acetonitrile (3:2) mixture for 6 minutes. Unless noted otherwise, reagents for solid phase RNA synthesis were purchased from Glen Research (Sterling, Va., USA).

All oligonucleotides were purified using reverse phase HPLC and analyzed by LC-MS using an Agilent 1290 Infinity series LC system coupled to an Agilent 6520 Q-TOF mass spectrometer (Agilent Technologies, Santa Clara, Calif., USA). Table 1 shows the sequences of all sgRNAs used and the masses obtained from deconvolution of the charge state series of peaks found. The deconvolution was done using Mass Hunter Qualitative Analysis (version B.06.00) software (Agilent).

TABLE 1

Overview of all sgRNAs used in the present study.

| SEQ ID NO: | Name | Sequence | Mass Calc. (Da) | Mass Obs. (Da) |
|---|---|---|---|---|
| SEQ ID NO: 4 | HBB unmodified sgRNA | CUUGCCCCACAGGGCAGUAAGUUUUAGAGCUAGAAAUAGCAAGUUAAAAUAAGGCUAGUCCGUUAUCAACUUGAAAAAGUGGCACCGAGUCGGUGCUUUU | 32187.42 | 32187.84 |
| SEQ ID NO: 5 | HBB M sgRNA | CUUGCCCCACAGGGCAGUAAGUUUUAGAGCUAGAAAUAGCAAGUUAAAAUAAGGCUAGUCCGUUAUCAACUUGAAAAAGUGGCACCGAGUCGGUGCUUUU | 32271.54 | 32271.35 |
| SEQ ID NO: 6 | HBB MS sgRNA | C●U●U●GCCCCACAGGGCAGUAAGUUUUAGAGCUAGAAAUAGCAAGUUAAAAUAAGGCUAGUCCGUUAUCAACUUGAAAAAGUGGCACCGAGUCGGUGCU●U●U●U | 32367.42 | 32367.31 |
| SEQ ID NO: 7 | HBB MSP sgRNA | C◆U◆U◆GCCCCACAGGGCAGUAAGUUUUAGAGCUAGAAAUAGCAAGUUAAAAUAAGGCUAGUCCGUUAUCAACUUGAAAAAGUGGCACCGAGUCGGUGCU◆U◆U◆U | 32619.93 | 32619.39 |
| SEQ ID NO: 8 | IL2G unmodified sgRNA | UGGUAAUGAUGGCUUCAACAGUUUUAGAGCUAGAAAUAGCAAGUUAAAAUAAGGCUAGUCCGUUAUCAACUUGAAAAAGUGGCACCGAGUCGGUGCUUUU | 32214.40 | 32214.37 |
| SEQ ID NO: 9 | IL2G M sgRNA | UGGUAAUGAUGGCUUCAACAGUUUUAGAGCUAGAAAUAGCAAGUUAAAAUAAGGCUAGUCCGUUAUCAACUUGAAAAAGUGGCACCGAGUCGGUGCUUUU | 32298.52 | 32297.01 |
| SEQ ID NO: 10 | IL2G MS sgRNA | U●G●G●UAAUGAUGGCUUCAACAGUUUUAGAGCUAGAAAUAGCAAGUUAAAAUAAGGCUAGUCCGUUAUCAACUUGAAAAAGUGGCACCGAGUCGGUGCU●U●U●U●U | 32394.4 | 32395.43 |
| SEQ ID NO: 11 | IL2G MSP sgRNA | U◆G◆G◆UAAUGAUGGCUUCAACAGUUUUAGAGCUAGAAAUAGCAAGUUAAAAUAAGGCUAGUCCGUUAUCAACUUGAAAAAGUGGCACCGAGUCGGUGCU◆U◆U◆U | 32646.91 | 32645.39 |
| SEQ ID NO: 12 | CCR5 unmodified sgRNA | GGCAGCAUAGUGAGCCCAGAGUUUUAGAGCUAGAAAUAGCAAGUUAAAAUAAGGCUAGUCCGUUAUCAACUUGAAAAAGUGGCACCGAGUCGGUGCUUUU | 32290.51 | 32289.07 |
| SEQ ID NO: 13 | CCR5 M sgRNA | GGCAGCAUAGUGAGCCCAGAGUUUUAGAGCUAGAAAUAGCAAGUUAAAAUAAGGCUAGUCCGUUAUCAACUUGAAAAAGUGGCACCGAGUCGGUGCUUUU | 32374.63 | 32375.3 |
| SEQ ID NO: 14 | CCR5 MS sgRNA | G●G●C●AGCAUAGUGAGCCCAGAGUUUUAGAGCUAGAAAUAGCAAGUUAAAAUAAGGCUAGUCCGUUAUCAACUUGAAAAAGUGGCACCGAGUCGGUGCU●U●U●U●U | 32470.51 | 32469.92 |
| SEQ ID NO: 15 | CCR5 MSP sgRNA | G◆G◆C◆AGCAUAGUGAGCCCAGAGUUUUAGAGCUAGAAAUAGCAAGUUAAAAUAAGGCUAGUCCGUUAUCAACUUGAAAAAGUGGCACCGAGUCGGUGCU◆U◆U◆U | 32723.02 | 32721.96 |
| SEQ ID NO: 16 | CCR5 'D' MS sgRNA | U●C●A●CUAUGCUGCCGCCCAGUGUUUUAGAGCUAGAAAUAGCAAGUUAAAAUAAGGCUAGUCCGUUAUCAACUUGAAAAAGUGGCACCGAGUCGGUGCU●U●U●U | 32281.32 | 32282.52 |
| SEQ ID NO: 17 | CCR5 'D' MSP sgRNA | U◆C◆A◆CUAUGCUGCCGCCCAGUGUUUUAGAGCUAGAAAUAGCAAGUUAAAAUAAGGCUAGUCCGUUAUCAACUUGAAAAAGUGGCACCGAGUCGGUGCU◆U◆U◆U | 32533.83 | 32533.55 |

TABLE 1-continued

Overview of all sgRNAs used in the present study.

| SEQ ID NO: | Name | Sequence | Mass Calc. (Da) | Mass Obs. (Da) |
|---|---|---|---|---|
| SEQ ID NO: 18 | CCR5 'Q' MS sgRNA | G●C●U●GUGUUUGCGUCUCUCCCGUUUUAGAGCUAGAAAUA GCAAGUUAAAAUAAGGCUAGUCCGUUAUCAACUUGAAAAAG UGGCACCGAGUCGGUGCU●U●U●U | 32252.22 | 32253.21 |
| SEQ ID NO: 19 | CCR5 'Q' MSP sgRNA | G♦C♦U♦GUGUUUGCGUCUCUCCCGUUUUAGAGCUAGAAAUA GCAAGUUAAAAUAAGGCUAGUCCGUUAUCAACUUGAAAAAG UGGCACCGAGUCGGUGCU♦U♦U♦U | 32504.73 | 32504.63 | sgRNA sequences as well as calculated and observed molecular weights are indicated. Nucleotides with 2'-O-methyl modifications are underlined. Modifications in the phosphate backbone are indicated with ● (MS) and ♦ (MSP).

2. In Vitro Cleavage Assays 4 kb PAM-addressable targets were prepared by preparative PCR amplification of plasmid-borne human sequences. In a 20 µL reaction volume, 50 fmoles of linearized DNA target in the presence of 50 nM sgRNA, 39 nM recombinant purified Cas9 protein (Agilent) and 10 mM MgCl$_2$ at pH 7.6 was incubated at 37° C. for 30 min. Upon completion, 0.5 µL of RNace It (Agilent) was added, and incubation was continued at 37° C. for 5 min and then at 70° C. for 15 min. Subsequently 0.5 µL of Proteinase K (Mol. Bio. grade, NEB) was added and incubated at 37° C. for 15 min. Aliquots were loaded into a DNA 7500 LabChip and were analyzed on a Bioanalyzer 2200. Cleavage frequencies were calculated by the formula: (a/b)×100 where 'a' is the sum of the band intensities of the two cleavage products and b is the sum of band intensities of cleaved and uncleaved DNA.

3. Plasmids sgRNA expression vectors were constructed by cloning of 20 bp oligonucleotide target sequences into px330 (Addgene plasmid #42230) containing a human codon-optimized SpCas9 expression cassette and a human U6 promoter driving the expression of the chimeric sgRNA (see Table 1 for sgRNA sequences).

All three plasmid targeting vectors carry approximately 2×800 bp arms of homology, which were generated by PCR amplification of the corresponding loci using genomic DNA isolated from K562 cells. The homology arms were then cloned into a ~2,900 base pair vector based on pBluescript SK+ using standard cloning methods. Between the homology arms, both the HBB and CCR5 donors contain the EF1α promoter driving expression of GFP. The IL2RG donor lacks a promoter and relies on endogenous activity of the IL2RG gene to drive GFP expression. The nucleic acid sequence of the IL2RG targeting vector is set forth as SEQ ID NO:1. The nucleic acid sequence of the HBB targeting vector is set forth as SEQ ID NO:2. The nucleic acid sequence of the CCR5 targeting vector is set forth as SEQ ID NO:3.

4. Cell Culture and Nucleofections

K562 and T cells were cultured at 37° C., 5% CO$_2$, and ambient oxygen levels. CD34+ hematopoietic stem/progenitor cells (HSPCs) were cultured at 37° C., 5% CO$_2$, and 5% O$_2$. K562 cells were maintained in RPMI 1640 (HyClone) supplemented with 10% bovine growth serum, 100 mg/ml streptomycin, 100 units/ml penicillin, and 2 mM L-glutamine. K562 cells were nucleofected using the Lonza Nucleofector 2b (program T-016) and a nucleofection buffer containing 100 mM KH$_2$PO$_4$, 15 mM NaHCO$_3$, 12 mM MgCl$_2$×6H$_2$O, 8 mM ATP, 2 mM glucose (pH 7.4). Nucleofection conditions: 100 µL nucleofection solution, 10$^6$ cells, 1 to 20 chemically modified sgRNA, 1 to 15 µg Cas9 mRNA (Cas9 mRNA, 5meC, Ψ, Product Code: L-6125, TriLink BioTechnologies, San Diego, Calif., USA), 2 µg sgRNA/Cas9-encoding plasmid, or 5 µg HR donor plasmid. CD3+ T cells were isolated from buffy coats obtained from the Stanford School of Medicine Blood Center using a human Pan T Cell Isolation Kit (Miltenyi Biotec, San Diego, Calif., USA). CD3+ cells were maintained in X-VIVO 15 (Lonza, Walkersville, Md., USA) supplemented with 5% human serum (Sigma-Aldrich, St. Louis, Mo., USA), 100 IU/mL human recombinant IL-2 (Peprotech, Rocky Hill, N.J., USA), and 10 ng/mL human recombinant IL-7 (BD Biosciences, San Jose, Calif., USA). Before nucleofection, T cells were activated for three days with immobilized anti-CD3 antibodies (clone: OKT3, eBioscience, San Diego, Calif., USA) and soluble anti-CD28 antibodies (clone: CD28.2, eBioscience). For non-activated CD3+ T cells, cells were nucleofected immediately after isolation. T cells were nucleofected using the Lonza Nucleofector 2b (program U-014) and the Human T Cell Nucleofector Kit (VPA-1002, Lonza). Nucleofection conditions: 100 µL nucleofection solution, 10$^6$ cells, 10 to 20 µg chemically modified sgRNA, 15 to 30 µg Cas9 (or 15 µg eGFP mRNA, TriLink BioTechnologies, San Diego, Calif., USA), 1 µg sgRNA/Cas9-encoding plasmid. Mobilized human peripheral blood CD34+ HSPCs were purchased from AllCells and thawed according to manufacturer's instructions. CD34+ HSPCs were maintained in X-VIVO 15 (Lonza) supplemented with SCF (100 ng/ml), TPO (100 ng/ml), Flt3-Ligand (100 ng/ml), IL-6 (100 ng/ml), and StemRegenin1 (0.75 mM). CD34+ HSPCs were nucleofected using the Lonza 4D-Nucleofector (program EO-100) and the P3 Primary Cell 4D-Nucleofector Kit (V4XP-3024). Nucleofection conditions: 100 µL nucleofection solution, 5×10$^5$ cells, 10 µg chemically modified sgRNA, 15 µg Cas9 mRNA, 1 µg plasmid. For Cas9 RNP experiments, Cas9 protein was purchased from PNA Bio (Thousand Oaks, Calif., USA) or Life Technologies (Carlsbad, Calif., USA). For all RNP experiments except for FIG. 8, Cas9 protein from PNA Bio was used. Cas9 protein was complexed with sgRNAs in a Cas9:sgRNA molar ratio of 1:2.5 for 10 min at 25° C. RNPs were nucleofected into K562 cells or T cells as described above with 10$^6$ cells in 100 of the respective nucleofection solutions. For the dual sgRNA experiments, the total sgRNA amount was 10 µg (10 µg when used individually and 2×5 µg when used together). For both T cells and CD34+ HSPCs, sgRNAs were nucleofected with 15 µg Cas9 mRNA into 10$^6$ cells. T cell nucleofections were performed as above whereas nucleofection of CD34+ HSPCs were similar to the T cells nucleofections using the Lonza Nucleofector 2b (program U-014) and the Human T Cell Nucleofector Kit (VPA-1002, Lonza). Directly after nucleofection CD34+ HSPCs were incubated at 30° C. for 24 hrs after which they were transferred to 37° C. until harvest of genomic DNA.

5. Flow Cytometry and Fluorescent Activated Cell Sorting (FACS)

For HR experiments, cells were analyzed 2-3 weeks after nucleofection depending on cell type when there was no remaining eGFP expression from episomal plasmid. eGFP expression was measured on an Accuri C6 flow cytometer (BD Biosciences, San Jose, Calif., USA). Cell death was measured with the LIVE/DEAD Fixable Red Dead Cell Stain Kit (Life Technologies, Carlsbad, Calif., USA) according to manufacturer's instructions and cells were analyzed on the Accuri C6 flow cytometer. For sorting of CD3+ T cells into CD4+ and CD8+ populations cells were stained with a mix of PE-Cy7 anti-human CD4 (clone: RPA-T4, Tonbo Biosciences, San Diego, Calif., USA) and an APC anti-human CD8a (clone: RPA-T8, Tonbo Biosciences) and the two populations were sorted on a FACS Aria II SORP.

6. Measuring Allele Modification Frequencies Using TIDE and T7 Assay

For TIDE and T7 assays, gDNA was extracted from cells three days after nucleofection (if not otherwise indicated) using QuickExtract DNA Extraction Solution (Epicentre, Madison, Wis., USA) following manufacturer's instructions. PCR amplicons spanning the sgRNA genomic target sites were generated using the iProof High-Fidelity Master Mix (Bio-Rad, Hercules, Calif., USA) with the following primer pairs:

IL2RG_fw (SEQ ID NO: 84): 5'-TCACACAGCACAT-ATTTGCCACACCCTCTG-3',
IL2RG_RV (SEQ ID NO: 85): 5'-TGCCCACATGAT-TGTAATGGCCAGTGG-3',
HBB_fw (SEQ ID NO: 86): 5'-CCAACTCCTAAGCCAGTGCCAGAAGAG-3',
HBB_ry (SEQ ID NO: 87) 5'-AGTCAGTGCC-TATCAGAAACCCAAGAG-3',
CCR5_fw (SEQ ID NO: 88): 5'-GCACAGGGTG-GAACAAGATGG-3',
CCR5_rv (SEQ ID NO: 89): 5'-CACCACCC-CAAAGGTGACCGT-3'.

For T7 assays, PCR amplicons were purified and 200 ng was denatured and re-annealed in a thermocycler and digested with T7 Endonuclease I (New England Biolabs, Waltham, Mass., USA) according to manufacturer's protocol. Digested DNA was run on a 4-20% TBE polyacrylamide gel, stained with Diamond Nucleic Acid Dye (Promega, Madison, Wis., USA), and visualized on a ChemiDoc XRS+ (Bio-Rad). Band intensities were analyzed using the Image Lab Software (Bio-Rad) and allele modification frequencies were calculated with the formula: 100×(1−(1−fraction cleaved)^0.5). For analyzing allele modification frequencies using TIDE (Tracking of In/dels by Decomposition, Brinkman et al., *Nucleic Acids Research* 42, e168 (2014)), the purified PCR products were Sanger-sequenced using both primers and each sequence chromatogram was analyzed with the online TIDE software available at the website tide.nki.nl. Analyses were performed using a reference sequence from a mock-transfected sample. Parameters were set to a maximum in/del size of 10 nucleotides and the decomposition window to cover the largest possible window with high quality traces. All TIDE analyses below the detection sensitivity of 3.5% were set to 0%. For sequencing of TOPO-cloned PCR fragments a 2.1 kb amplicon (WT size) spanning the cleavage site(s) was generated using iProof High-Fidelity Master Mix and primers 5'-GGCTGTTGTCATCTATGACCTTCCC-3' (SEQ ID NO: 90) and 5'-TGTAAACTGAGCTTGCTGCTCGCTCG-3' (SEQ ID NO: 91) with 25 cycles including 72° C. annealing temperature, and 2 min. elongation time. The PCR reaction products were subcloned into a plasmid directly using the Zero Blunt TOPO PCR Cloning Kit (Life Technologies) according to the manufacturer's protocol. TOPO reactions were transformed into XL-1 Blue competent cells, plated on agar plates with kanamycin, and single colonies were sequenced directly from the plates by McLab (South San Francisco, Calif., USA) by Rolling Circle Amplification followed by sequencing using primer 5'-GCACAGGGTG-GAACAAGATGG-3' (SEQ ID NO: 92).

7. Proliferation Assay

For measuring proliferation of T cells following nucleofection, the CellTiter-Glo 2.0 Assay (Promega, Madison, Wis., USA) was used. Directly after nucleofection, T cells were transferred to multiple 96-well U-bottom 96-well plates at $3 \times 10^4$ cells/well. Directly after nucleofection and at 24-hr intervals, cells were transferred to white 96-well plates in 100 medium and adding 100 µL CellTiter-Glo 2.0 per manufacturer's guidelines. Luminescence was read on a Tecan Infinite 200 PRO (Tecan, Männedorf, Switzerland) using a 1 sec integration time.

8. Deep Sequencing to Quantify Efficiency and Specificity of Genome Modification For each gene targeting experiment, genomic DNA was extracted from the various CRISPR-treated and control K562 cells 48 hours post-transfection. Genomic regions flanking the CRISPR target and three off-targets (Table 2) were amplified by two rounds of PCR to attach (treatment-specific) barcodes and Illumina sequencing adaptors (Table 3). Barcoded PCR amplicons were pooled equimolarly, purified by a spin-column and sequenced on the Illumina MiSeq DNA sequencer platform. See, "9. Generation of CRISPR on- and predicted off-target amplicons for deep sequencing" section below for further details.

Table 2 provides a list of on- and off-target loci interrogated by deep sequencing of PCR amplicons. For the CCR5, HBB, and IL2RG-targeting CRISPR experiments, the intended genomic target sequence ('ON') and three computationally predicted OFF-target sequences ('OFF1-3') are presented with their genomic location (human genome build assembly hg38). Chosen off-target sequences were predicted top-scorers by both the COSMID (Cradick et al., *Molecular therapy. Nucleic acids* 3, e214 (2014) and Optimized CRISPR Design (Hsu et al., Nature Biotechnology, 31, 827-832 (2013)) webtools (MIT design), except HBB-OFF3 which was only predicted to have significant activity by COSMID. Predicted target activity increases with increasing COSMID score values and decreasing 'MIT design' score values. The PAM sites and mismatches in off-target sequences are indicated by red colored and bolded text, respectively.

TABLE 2

| | | List of on- and off-target loci interrogated by deep sequencing of PCR amplicons. | | | | |
|---|---|---|---|---|---|---|
| SEQ ID NO: | Target ID | Target site sequence (5' → 3') | Genomic location | Strand | COSMID | MIT design |
| | | CCR5 targeting guide RNA | | | | |
| SEQ ID NO: 20 | ON | GGCAGCATAGTGAGCCCAGAAGG | Chr: 46373153-46373175 | – | 0 | 56 |

TABLE 2-continued

List of on- and off-target loci interrogated by deep sequencing of PCR amplicons.

| SEQ ID NO: | Target ID | Target site sequence (5' → 3') | Genomic location | Strand | COSMID | MIT design |
|---|---|---|---|---|---|---|
| SEQ ID NO: 21 | OFF1 | ATCATCATAGTGAGCCCAGAGAG | Chr: 15440658-15440680 | + | 0.44 | 2.4 |
| SEQ ID NO: 22 | OFF2 | ACCAGCAGAGTGAGCCCAGAGGG | Chr: 3744369-3744391 | + | 0.52 | 2.6 |
| SEQ ID NO: 23 | OFF3 | AGGAGCAGAGTGAGCCCAGAGAG | Chr: 92469456-92469478 | + | 0.54 | 2.6 |
| HBB targeting guide RNA | | | | | | |
| SEQ ID NO: 24 | ON | CTTGCCCCACAGGGCAGTAACGG | Chr11: 5226968-5226690 | + | 0 | 65 |
| SEQ ID NO: 25 | OFF1 | TCAGCCCCACAGGGCAGTAAGGG | Chr9: 101833584-1018833606 | + | 0.4 | 2.3 |
| SEQ ID NO: 26 | OFF2 | CCTCTCCCACAGGGCAGTAAAGG | Chr17: 68628098-68628120 | − | 0.49 | 2.4 |
| SEQ ID NO: 27 | OFF3 | TTTTCCCCAAAGGGCAGTAATAG | Chr13: 109165988-109166010 | + | 0.79 | N/A |
| IL2RG targeting guide RNA | | | | | | |
| SEQ ID NO: 28 | ON | TGGTAATGATGGCTTCAACATGG | ChrX: 71111591-71111541 | + | 0 | 49 |
| SEQ ID NO: 29 | OFF1 | TGGGAAGGATGGCTTCAACACAG | Chr7: 151485304-151485326 | − | 0.4 | 3.9 |
| SEQ ID NO: 30 | OFF2 | TGGTGAGGATGGCTTCAACACGG | Chr1: 167730172-167730194 | − | 0.42 | 3.7 |
| SEQ ID NO: 31 | OFF3 | TGGTAATGATGACTTCAACATAG | Chr3: 72764801-727664823 | − | 0.8 | 49.2 |

Table 3 provides a list of oligonucleotide primers used for generation of on- and off-target amplicons to quantify in/del frequencies by deep sequencing. The gene-specific hybridization sequences of the gene-specific amplicon primers and barcodes of the Illumina barcoding primers are indicated with underlined and bolded text, respectively.

TABLE 3

List of oligonucleotide primers used for generation of on- and off-target amplicons to quantify in/del frequencies by deep sequencing.

| SEQ ID NO: | Primer name | Primer sequence (5' → 3') |
|---|---|---|
| Gene-specific amplicon primers | | |
| SEQ ID NO: 32 | CCR5_ON-fwd | CGACAGGTTCAGAGTTCTACAGTCCGACGATCCAAACACAGCATGGACGACA |
| SEQ ID NO: 33 | CCR5_ON-rev | GTGACTGGAGTTCAGACGTGTGCTCTTCCGATCTGGCTGAAGAGCATGACTGACA |
| SEQ ID NO: 34 | CCR5_OFF1-fwd | CGACAGGTTCAGAGTTCTACAGTCCGACGATCGGGGAAGCAGTCTGGACTTAGA |
| SEQ ID NO: 35 | CCR5_OFF1-rev | GTGACTGGAGTTCAGACGTGTGCTCTTCCGATCTCCTGCCATTAAATCCACCAAA |
| SEQ ID NO: 36 | CCR5_OFF2-fwd | CGACAGGTTCAGAGTTCTACAGTCCGACGATCAGCGAGTCGAGTTCAGGTG |
| SEQ ID NO: 37 | CCR5_OFF2-rev | GTGACTGGAGTTCAGACGTGTGCTCTTCCGATCTGGCTACCTACCCCAGGTTCT |
| SEQ ID NO: 38 | CCR5_OFF3-fwd | CGACAGGTTCAGAGTTCTACAGTCCGACGATCTCTCACCAACACTGCCGAAT |
| SEQ ID NO: 39 | CCR5_OFF3-rev | GTGACTGGAGTTCAGACGTGTGCTCTTCCGATCTTGGCATATAGTGCTCCCCACT |
| SEQ ID NO: 40 | HBB_ON-fwd | CGACAGGTTCAGAGTTCTACAGTCCGACGATCTCTGTCTCCACATGCCCAGT |
| SEQ ID NO: 41 | HBB_ON-rev | GTGACTGGAGTTCAGACGTGTGCTCTTCCGATCTCAGGGCAGAGCCATCTATTG |
| SEQ ID NO: 42 | HBB_OFF1-fwd | CGACAGGTTCAGAGTTCTACAGTCCGACGATCTCCCGTTCTCCACCCAATAG |

TABLE 3-continued

List of oligonucleotide primers used for generation of on- and off-target amplicons to quantify in/del frequencies by deep sequencing.

| SEQ ID NO: | Primer name | Primer sequence (5' → 3') |
|---|---|---|
| SEQ ID NO: 43 | HBB_OFF1-rev | GTGACTGGAGTTCAGACGTGTGCTCTTCCGATCTGATTTCCAGGCTATGCTTCCA |
| SEQ ID NO: 44 | HBB_OFF2-fwd | CGACAGGTTCAGAGTTCTACAGTCCGACGATCGTTGGCAGGGAGACTTACCA |
| SEQ ID NO: 45 | HBB_OFF2-rev | GTGACTGGAGTTCAGACGTGTGCTCTTCCGATCTCCCATGGTACGACTGTTCTCA |
| SEQ ID NO: 46 | HBB_OFF3-fwd | CGACAGGTTCAGAGTTCTACAGTCCGACGATCTGGGGCCTTCAAGTGTTCTT |
| SEQ ID NO: 47 | HBB_OFF3-rev | GTGACTGGAGTTCAGACGTGTGCTCTTCCGATCTGTGTGCTCCTATGCCTGGTT |
| SEQ ID NO: 48 | IL2RG_ON-fwd | CGACAGGTTCAGAGTTCTACAGTCCGACGATCCATTGGGCGTCAGAATTGTC |
| SEQ ID NO: 49 | IL2RG_ON-rev | GTGACTGGAGTTCAGACGTGTGCTCTTCCGATCTAGGTTCTTTCCACCGGAAGC |
| SEQ ID NO: 50 | IL2RG_OFF1-fwd | CGACAGGTTCAGAGTTCTACAGTCCGACGATCTCCGGAAGTTATTCAAGTCTGA |
| SEQ ID NO: 51 | IL2RG_OFF1-rev | GTGACTGGAGTTCAGACGTGTGCTCTTCCGATCTGTCTGGCATCAGAGCACAAA |
| SEQ ID NO: 52 | IL2RG_OFF2-fwd | CGACAGGTTCAGAGTTCTACAGTCCGACGATCCCTGGGCCATATCAAGAGAC |
| SEQ ID NO: 53 | IL2RG_OFF2-rev | GTGACTGGAGTTCAGACGTGTGCTCTTCCGATCTTCTTTGGGGTGATGTTTGTG |
| SEQ ID NO: 54 | IL2RG_OFF3-fwd | CGACAGGTTCAGAGTTCTACAGTCCGACGATCCACAACAGTTGACCCAGGAA |
| SEQ ID NO: 55 | IL2RG_OFF3-rev | GTGACTGGAGTTCAGACGTGTGCTCTTCCGATCTCCCAACCCAGGTCTCTGAAC |
| | Illumina barcoding primers | |
| SEQ ID NO: 56 | P5-BC_A-fwd | AATGATACGGCGACCACCGAGATCTACACTAGAGCTCCGACAGGTTCAGAGTTCTACAGTCCGACGATC |
| SEQ ID NO: 57 | P5-BC_B-fwd | AATGATACGGCGACCACCGAGATCTACACTCATAGCGCGACAGGTTCAGAGTTCTACAGTCCGACGATC |
| SEQ ID NO: 58 | P5_BC_C-fwd | AATGATACGGCGACCACCGAGATCTACACGTAGCACTCGACAGGTTCAGAGTTCTACAGTCCGACGATC |
| SEQ ID NO: 59 | P5-BC_D-fwd | AATGATACGGCGACCACCGAGATCTACACGCTCATAGCGACAGGTTCAGAGTTCTACAGTCCGACGATC |
| SEQ ID NO: 60 | P5-BC_E-fwd | AATGATACGGCGACCACCGAGATCTACACATGCATCGCGACAGGTTCAGAGTTCTACAGTCCGACGATC |
| SEQ ID NO: 61 | P5-BC_F-fwd | AATGATACGGCGACCACCGAGATCTACACAGTCGATCCGACAGGTTCAGAGTTCTACAGTCCGACGATC |
| SEQ ID NO: 62 | P5-BC-G_fwd | AATGATACGGCGACCACCGAGATCTACACCACTGTGACGACAGGTTCAGAGTTCTACAGTCCGACGATC |
| SEQ ID NO: 63 | P5-BC-H_fwd | AATGATACGGCGACCACCGAGATCTACACCGAGTATCCGACAGGTTCAGAGTTCTACAGTCCGACGATC |
| SEQ ID NO: 64 | P7-BC-A_rev | CAAGCAGAAGACGGCATACGAGATTAGAGCTCGTGACTGGAGTTCAGACGTGTGCTCTTCCGATCT |
| SEQ ID NO: 65 | P7-BC_B rev | CAAGCAGAAGACGGCATACGAGATTCATAGCGGTGACTGGAGTTCAGACGTGTGCTCTTCCGATCT |
| SEQ ID NO: 66 | P7-BC_C rev | CAAGCAGAAGACGGCATACGAGATGTAGCACTGTGACTGGAGTTCAGACGTGTGCTCTTCCGATCT |
| SEQ ID NO: 67 | P7-BC_D rev | CAAGCAGAAGACGGCATACGAGATGCTCATAGGTGACTGGAGTTCAGACGTGTGCTCTTCCGATCT |
| SEQ ID NO: 68 | P7-BC_E_rev | CAAGCAGAAGACGGCATACGAGATATGCATCGGTGACTGGAGTTCAGACGTGTGCTCTTCCGATCT |
| SEQ ID NO: 69 | P7-BC_F_rev | CAAGCAGAAGACGGCATACGAGATAGTCGATCGTGACTGGAGTTCAGACGTGTGCTCTTCCGATCT |
| SEQ ID NO: 70 | P7-BC-G_rev | CAAGCAGAAGACGGCATACGAGATCACTGTGAGTGACTGGAGTTCAGACGTGTGCTCTTCCGATCT |

TABLE 3-continued

List of oligonucleotide primers used for generation of on- and off-target
amplicons to quantify in/del frequencies by deep sequencing.

| SEQ ID NO: | Primer name | Primer sequence (5' → 3') |
|---|---|---|
| SEQ ID NO: 71 | P7-BC-H_rev | CAAGCAGAAGACGGCATACGAGATCGAGTATCGTGACTGGAGTTCAGACGTGTGCTCTTCCGATCT |

The gene-specific hybridization sequences of the gene-specific amplicon primers and barcodes of the Illumina barcoding primers are indicated with underlined and bolded text, respectively.

For analysis of sequencing data, reads from different treatments were binned by their corresponding treatment barcodes and were mapped to the genome using BWA-MEM (Li et al., *Bioinformatics* 26, 589-595 (2010)) (bwa-0.7.10) with default parameters. Inconsistent paired end mappings (>1 Kbp apart) were filtered from the analysis along with low quality mapped and secondary aligned reads as defined by the default parameters in BWA-MEM. For each of the on and off-target regions we calculated the % of reads with in/dels surrounding the predicted cut-site, where the predicted cut-site is estimated to be between the $3^{rd}$ and the $4^{th}$ position upstream the PAM site. The in/del % for each position in the genome was calculated by using in/del[i]=(I[i]+D[i])/C[i], where D[i] and I[i] indicates the number of reads with a deletion or an insertion of any size at position i, respectively, and C[i] indicates the number of reads mapped to any genomic interval containing position i. The in/del % for each target was then calculated by in/del[c], where c is the expected cut-site which is the $4^{th}$ position upstream the PAM site. In cases with homo-nucleotide sequence at position 4, 'AA' in IL2Rg and 'CCC' in CCR5, and an insertion event the BWA_MEM aligner cannot resolve the position of the inserted nucleotide. This was corrected by taking the relevant position in the alignment report instead of position 4, specifically, taking positions 3 and 6 for IL2Rg and CCR5 off-targets, respectively.

9. Generation of CRISPR On- and Predicted Off-Target Amplicons for Deep Sequencing For each targeted gene locus, $10^6$ K562 cells were transfected with either 1 µg or 20 µg of the synthetic guide RNAs (unmodified, M, MS or MSP) and 2 µg of the Cas9 expression plasmid (PX330), 2 µg of sgRNA plasmid encoding both the sgRNA and Cas9 protein (positive control), or 2 µg of PX330 only (Cas9 only, negative control). Additionally, for experiments targeting the IL2RG gene locus, $10^6$ K562 cells were transfected with 15 µg Cas9 mRNA and 10 µg of synthetic guide RNA (unmodified or MS), 15 µg Cas9 protein pre-complexed with 7.6 µg synthetic guide RNA (unmodified or MS). Genomic DNA from these samples and mock transfection samples ($2^{nd}$ negative control) was extracted 72 hours post transfection using QuickExtract™ DNA Extraction Solution (Epicentre, Madison, Wis.) according to the manufacturer's specifications. 40 ng of genomic DNA was used as a template for PCR amplification of the on-target and three computationally predicted off-target loci (Table 2), using PfuUltra II HS 2× Master Mix (Agilent Technologies, Santa Clara, Calif.) and gene-specific primers that tag the amplicon ends with sequencing primers utilized in deep sequencing by the MiSeq (Illumina, San Diego, Calif.) platform (Table 3). A second PCR reaction was carried out on the on- and off-target amplicons (Table 4) to append additional Illumina sequencing adaptors (i.e., P5, P7) and custom, dual 8-bp barcodes, uniquely identifying the corresponding transfection treatments. Following the $2^{nd}$ PCR, barcoded amplicons were quantified by Agilent D1000 TapeStation, pooled in equimolar concentrations before purification with a QIAquick PCR Purification Kit (Qiagen, Valencia, Calif.) according to the manufacturer's instructions. The purified library was sequenced on an Illumina MiSeq DNA sequencer, $2 \times 20^1$ cycles with dual indexing by a NGS DNA sequencing service (Seqmatic, Fremont, Calif.).

Table 4 provides a list of CCR5, HBB, and IL2RG on- and off-target amplicons generated for deep sequencing analysis of in/del frequencies. Amplicon sizes (of unedited genomic DNA) range from 183-220 bp, with a minimum of 50 bp from the target site to the hybridization sequence of the gene-specific primer. The hybridization sequences used for amplicon generation from genomic DNA and putative CRISPR-target sites are indicated in underlined and bolded text, respectively.

TABLE 4

List of CCR5, HBB, and IL2RG on- and off-target amplicons generated
for deep sequencing analysis of in/del frequencies.

| SEQ ID NO: | Target ID | Target amplicon sequence (5' → 3') |
|---|---|---|
| | | CCR5 targeting guide RNA |
| SEQ ID NO: 72 | ON | <u>CAAACACAGCATGGACGACAGCCAGGTACCTATCGATTGTCAGGAGGATGATGAAGAAGATTCCAGAGAAGAAGCCTATAAAATAGAGCCCTGTCAAGAGTTGACACATTGTATTTCCAAAGTCCCACTGGGC</u>GGCAGCATAGTGAGCCCAGAAGGGGACAGTAAGAAGGAAAAACAGGTCAGAGATGGCCAGGTTGAGCAGGTA<u>GATGTCAGTCATGCTCTTCAGCC</u> |
| SEQ ID NO: 73 | OFF1 | <u>GGGGAAGCAGTCTGGACTTAGAAAGGAAATAGGTGGTCTGTCATAGGGGCTTTCATTAGAGTTAAACTTCATAGAGTCAACTGTTTC</u>ATCATCATAGTGAGCCCAGAGAGCCACTGCCCAGCAGCATGCTCACACCACCTACCCTAGTGTAGGTAATAGGTCTACGCTAGGACCCCGTGCTGGGCTCTCAGCCCATCATGAGAT<u>TTTGGTGGATTTAATGGCAGG</u> |
| SEQ ID NO: 74 | OFF2 | <u>AGCGAGTCGAGTTCAGGTGGGAGCAGAGGGCGCCCACCAGCAGAGCGAGTCGAGTCCAGGCGGGAGCAGAGGGCGCAC</u>ACCAGCAGAGTGAGCCCAGAGGGTTTAAAGAAGGGGCGGTCTCTACGGTATGGGTAGAGTCAGGGGAACTAGGAAAGGACAGAGC<u>AGAACCTGGGGTAGGTAGCC</u> |

TABLE 4-continued

List of CCR5, HBB, and IL2RG on- and off-target amplicons generated
for deep sequencing analysis of in/del frequencies.

| SEQ ID NO: | Target ID | Target amplicon sequence (5' → 3') |
|---|---|---|
| SEQ ID NO: 75 | OFF3 | TCTCACCAACACTGCCGAATGTCATCTCTTCTCATCTTTATCTCTATTCTTTGCTTCC<br>TGTCTTCAGGGCTCTTCCCTTGGCATTCACCAGGAGCAGAGTGAGCCCAGAGAGCTGA<br>GTGGTATCCCTTCTTCTTGGGTCCCTGAGCCCTGACCTGGAGCAATGCTGTGAGACAG<br>CAGGAAAGGAGGGGAGTGTGG<u>AGTGGGGAGCACTATATGCCA</u> |

HBB targeting guide RNA

| SEQ ID NO: 76 | ON | TCTGTCTCCACATGCCCAGTTTCTATTGGTCTCCTTAAACCTGTCTTGTAACCTTGAT<br>ACCAACCTGCCCAGGGCCTCACCACCAACTTCATCCACGTTCACCTTGCCCCACAGGG<br>CAGTAACGGCAGACTTCTCCTCAGGAGTCAGATGCACCATGGTGTCTGTTTGAGGTTG<br>CTAGTGAACACAGTTGTGTCAGAAGCAAATGTAAG<u>CAATAGATGGCTCTGCCCTG</u> |
| SEQ ID NO: 77 | OFF1 | TCCCGTTCTCCACCCAATAGCTATGGAAAGGGGAAGATCCCAGAGAACTTGGATAGGA<br>AAGGTGAAGTCAGAGCAGTGCTTCAGCCCCACAGGGCAGTAAGGGCAGCCTTCCTCTA<br>AATACCAGATTCCCAAATCTGGCTGTGCTTTCAATTTGGGAGTTGGACATACTGCTAA<br>ACTATAATTTCTTAGGCCGTACCTAAAATATATTAT<u>GGAAGCATAGCCTGGAAATC</u> |
| SEQ ID NO: 78 | OFF2 | GTTGGCAGGGAGACTTACCAGCTTCCCGTATCTCCCTCCACATGGAGGCAGGACACGC<br>TCTGGCCTTGCCCACCCTCCCACTAGCCTCTCCCACAGGGCAGTAAAGGTGAGTCTGG<br>GAGAAAGAACCGGTCAGACTTAGTTCAGCTCCACCCTTTCCTCCTGGGAGTGAGTCTT<br>TCCAAGACAGAGCATGTTTTTTTCTACCCCTCAG<u>TGAGAACAGTCGTACCATGGG</u> |
| SEQ ID NO: 79 | OFF3 | TGGGGCCTTCAAGTGTTCTTCCCAAGAGTCAGAGTGAACCAGAACCAAGAACCATGTT<br>GAGTTGCCCAGATGTAACCAGGCCTACAGGTACCTGGGAGAAACACGTGTACATTTTC<br>CCCAAAGGGCAGTAATAGCATCCTAGGCTTCAAAACATTCATAGAAACCATTTTTCAA<br>ATGCAAAGTCCAACACAGTTAGAAATAA<u>CCAGGCATAGGAGCACAC</u> |

IL2RG targeting guide RNA

| SEQ ID NO: 80 | ON | CATTGGGCGTCAGAATTGTCGTGTTCAGCCCCACTCCCAGCAGGGGCAGCTGCAGGAA<br>TAAGAGGGATGTGAATGGTAATGATGGCTTCAACATGGCGCTTGCTCTTCATTCCCTG<br>GGTGTAGTCTGTCTGTGTCAGGAACCTGGGTCCCTCACCCACTACCCCTCCCCACCCA<br>CACGTTTCCTCTGTCATAG<u>CTTCCGGTGGAAAGAACCT</u> |
| SEQ ID NO: 81 | OFF1 | TCCGGAAGTTATTCAAGTCTGATTTTCTTTCCTCCCTTGTCAGGGAAAAGAAGTTGTG<br>ACAAATTGCTTGGATCCTTAAGCTTAAGTGGGAAGGATGGCTTCAACACAGAACATCT<br>GTTTCATTGCTGTTTTATCCGTCAGTAAAACTGTTACTTCTTTTATGTACTAAAAGTT<br>CTTAGCACTTAACTAATATTAGCT<u>CTTTGTGCTCTGATGCCAGAC</u> |
| SEQ ID NO: 82 | OFF2 | CCTGGGCCATATCAAGAGACTCTGCCTCAAAAAAGAAAAGAAAGAAAGAAAAAGAAAA<br>AAAAAAGAACATCATTAAAAATCCCTGAGGAGCATTTAGAGTATTGGGTGGCACAAAC<br>AGATTCTGCATGATTGTGAGGATGGCTTCAACACGGCAGCTTTATTCCTCTTTAACAG<br>AGTCAGCAGCATCAAGGCATGAGGGATCTTGG<u>CACAAACATCACCCCAAAGA</u> |
| SEQ ID NO: 83 | OFF3 | CACAACAGTTGACCCAGGAACAGGGGGAACCTCCCACCATTCCCATCCCACTGTTTGA<br>TCAGATCCAAGAATCCACAATATTGAGAGTGAATGAAAAGTGTCAGCTGGTAATGATG<br>ACTTCAACATAGTCAGAACTCTTTGGGGTGTTCCAAACATCATGGTGCATATGTATTA<br>CCTGGGAGTCTTGTTAAAAAGACTCCTGTTCAGAGACCTGGGTTGGG |

Amplicon sizes (of unedited genomic DNA) range from 183-220 bp, with a minimum of 50 bp from the target site to the hybridization sequence of the gene-specific primer. The hybridization sequences used for amplicon generation from genomic DNA and putative CRISPR-target sites are indicated in underlined and bolded text, respectively.

10. On- and Off-Target Activity of Chemically Modified sgRNAs

Table 5 shows the numbers on which FIGS. 1C, 1E, and 5 are based. Specificity of targeted cleavage mediated by synthetic sgRNAs as performed in FIG. 1C with 2 μg Cas9 plasmid and either 1 μg sgRNA (upper panel) or 20 μg sgRNA (lower panel). In/del frequencies were measured by deep sequencing of PCR amplicons from the targeted genomic loci and three bioinformatically predicted off-target loci for each gene. Average values are shown +/−SEM, n=3.

TABLE 5

| | | 2 μg CAS9 PLASMID AND 1 μg SGRNA | | | | |
|---|---|---|---|---|---|---|
| | | Mock | Unmodified | M | MS | MSP |
| IL2RG | On-target | 0.16 ± 0.03 | 2.43 ± 0.23 | 13.47 ± 0.54 | 68 ± 1.06 | 75.73 ± 1.30 |
| | Off-target 1 | 0.00 | 0.00 | 0.00 | 0.00 | 0.00 |
| | Off-target 2 | 0.00 | 0.00 | 0.10 ± 0.00 | 1.00 ± 0.10 | 0.37 ± 0.03 |
| | Off-target 3 | 0.00 | 0.00 | 0.00 | 0.00 | 0.00 |

TABLE 5-continued

| | | | | | | |
|---|---|---|---|---|---|---|
| HBB | On-target | 0.15 ± 0.05 | 1.3 ± 0.08 | 12.4 ± 0.28 | 48.17 ± 0.39 | 38.68 ± 0.85 |
| | Off-target 1 | 0.01 ± 0.01 | 0.84 ± 0.07 | 7.01 ± 0.36 | 27.31 ± 0.60 | 9.51 ± 0.25 |
| | Off-target 2 | 0.00 | 0.00 | 0.01 ± 0.00 | 0.00 | 0.00 |
| | Off-target 3 | 0.00 | 0.00 | 0.00 | 0.00 | 0.00 |
| CCR5 | On-target | 0.02 ± 0.01 | 4.26 ± 0.18 | 3.41 ± 0.23 | 24.6 ± 1.25 | 22.78 ± 1.76 |
| | Off-target 1 | 0.01 ± 0.00 | 0.01 ± 0.00 | 0.01 ± 0.00 | 0.01 ± 0.00 | 0.02 ± 0.00 |
| | Off-target 2 | 0.01 ± 0.01 | 0.01 ± 0.00 | 0.01 ± 0.00 | 0.08 ± 0.03 | 0.54 ± 0.10 |
| | Off-target 3 | 0.01 ± 0.00 | 0.01 ± 0.00 | 0.01 ± 0.00 | 0.01 ± 0.00 | 0.01 ± 0.00 |

| 2 μg CAS9 PLASMID AND 20 μg SGRNA | | | | | | |
|---|---|---|---|---|---|---|
| | | Unmodified | M | MS | MSP | sgRNA plasmid |
| IL2RG | On-target | 23.4 ± 1.8 | 48.13 ± 0.4 | 75.3 ± 5.1 | 83.27 ± 0.7 | 70.53 ± 0.01 |
| | Off-target 1 | 0.00 | 0.03 ± 0.03 | 0.13 ± 0.03 | 0.00 | 0.00 |
| | Off-target 2 | 0.13 ± 0.03 | 1.20 ± 0.06 | 7.83 ± 0.58 | 2.77 ± 0.24 | 0.07 ± 0.00 |
| | Off-target 3 | 0.00 | 0.10 ± 0.00 | 0.30 ± 0.00 | 0.10 ± 0.00 | 0.17 ± 0.00 |
| HBB | On-target | 19.42 ± 0.27 | 40.99 ± 1.4 | 65.91 ± 0.62 | 60.71 ± 0.25 | 31.11 ± 0.04 |
| | Off-target 1 | 9.2 ± 0.38 | 33.56 ± 2.3 | 55.1 ± 0.97 | 19.08 ± 0.49 | 25.44 ± 0.04 |
| | Off-target 2 | 0.00 | 0.00 | 0.00 | 0.00 | 0.00 |
| | Off-target 3 | 0.00 | 0.00 | 0.00 | 0.00 | 0.00 |
| CCR5 | On-target | 11.04 ± 2.5 | 14.87 ± 2.1 | 56.3 ± 3.3 | 52.19 ± 4.5 | 45.86 ± 0.03 |
| | Off-target 1 | 0.02 ± 0.01 | 0.01 ± 0.00 | 0.01 ± 0.00 | 0.01 ± 0.00 | 0.01 ± 0.00 |
| | Off-target 2 | 0.01 ± 0.00 | 0.02 ± 0.00 | 1.75 ± 0.18 | 5.32 ± 0.68 | 0.02 ± 0.00 |
| | Off-target 3 | 0.01 ± 0.00 | 0.01 ± 0.00 | 0.02 ± 0.01 | 0.02 ± 0.00 | 0.01 ± 0.00 |

Example 2. CRISPR/Cas9-Based Homologous Recombination Using Chemically Modified Guide RNAs and a Synthetic Single Strand Oligodeoxynucleotide (ssODN) Template Stimulated human primary T cells from three different donors were nucleofected with 10 μg CCR5 sgRNA (unmodified or MS), 15 μg Cas9 mRNA, and 2.81 μg of a 183nt CCR5 ssODN (with or without phosphorothioate ('PS') linkages between the three terminal nucleotides at both ends). The ssODN contained a central HindIII restriction site not present in the WT CCR5 sequence. Genomic DNA (gDNA) was extracted three days after nucleofections and PCR products spanning the target site (outside the sequence homologous to the ssODN) were generated and digested with HindIII. Restriction fragments were analyzed on a 2% TBE agarose gel and HDR frequencies were calculated.

Figure 21:
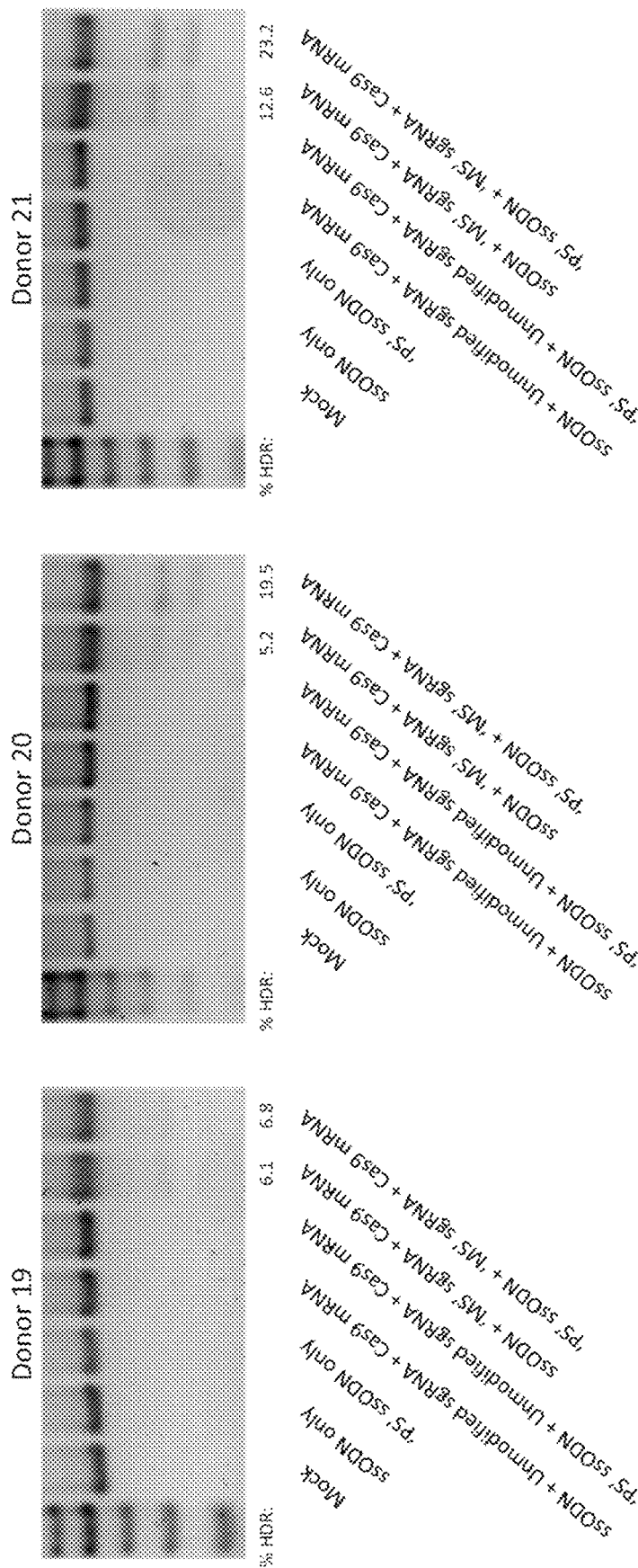
FIG. 21 shows PCR products spanning the CCR5 target site after homologous recombination using chemically modified CCR5 sgRNAs, Cas9 mRNA and a CCR5 ssODN.

FIG. 21 depicts the agarose gels from the HDR experiment. HDR frequency was increased when modified sgRNAs were used. In addition, HDR frequencies were further increased when the ssODN contained phosphothioate linkages between the three terminal nucleotides at both ends.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A primary CD34+hematopoietic stem or progenitor cell (HSPC) comprising:
   (a) a modified single guide RNA (sgRNA) comprising a nucleotide sequence that is complementary to a sequence within the HBB gene, wherein the modified sgRNA sequence is selected from the group consisting of SEQ ID NO: 6 and SEQ ID NO: 7;
   (b) a Cas polypeptide, an mRNA encoding the Cas polypeptide, or a recombinant expression vector comprising a nucleotide sequence encoding the Cas polypeptide.

2. The primary CD34$^+$ hematopoietic stem or progenitor cell of claim 1, wherein the primary CD34$^+$ hematopoietic stem or progenitor cell comprises a mutation in the HBB gene responsible for sickle cell anemia.

3. The primary CD34$^+$ hematopoietic stem or progenitor cell of claim 1, wherein the primary CD34$^+$ hematopoietic stem or progenitor cell comprises a mutation in the HBB gene responsible for thalassemia.

4. The primary CD34$^+$ hematopoietic stem or progenitor cell of claim 1, further comprising a recombinant donor repair template.

5. The primary CD34$^+$ hematopoietic stem or progenitor cell of claim 4, wherein the recombinant donor repair template comprises two nucleotide sequences comprising two non-overlapping, homologous portions, wherein one of the two homologous portions is located at the 5' end and the other homologous portion is located at the 3' end of the recombinant donor template, wherein each homologous portion is homologous to a corresponding region of the HBB gene to undergo genome editing.

6. The primary CD34$^+$ hematopoietic stem or progenitor cell of claim 4, wherein the recombinant donor repair template comprises a synthetic single-stranded oligodeoxynucleotide (ssODN) template comprising a nucleotide sequence encoding a mutation to correct a single nucleotide polymorphism (SNP) in the HBB gene and two nucleotide sequences comprising two non-overlapping, homologous portions that are homologous to corresponding regions of the HBB gene, wherein one of the two homologous portions is located at the 5' end and the other homologous portion is located at the 3' end of the recombinant donor template.

7. The primary CD34$^+$ hematopoietic stem or progenitor cell of claim 1, wherein the Cas polypeptide is endonuclease-deficient.

8. The primary CD34$^+$ hematopoietic stem or progenitor cell of claim 1, wherein the Cas polypeptide is a Cas9 polypeptide, a variant thereof, or a fragment thereof.

9. The primary CD34$^+$ hematopoietic stem or progenitor cell of claim 1, wherein the Cas polypeptide is a nickase.

10. The primary CD34$^+$ hematopoietic stem or progenitor cell of claim 1, wherein the primary cell comprises mRNA encoding the Cas polypeptide.

11. A population of primary CD34$^+$ hematopoietic stem and progenitor cell (HSPCs) comprising the primary CD34$^+$ hematopoietic stem or progenitor cell of claim 1.

12. The population of primary CD34$^+$ HSPCs of claim 11, wherein the population of primary CD34$^+$ HSPCs is isolated from a subject having sickle cell anemia or thalassemia.

13. The population of primary CD34$^+$ HSPCs of claim 11, wherein the modified sgRNA induces gene editing of HBB in at least about 30% of the population of primary CD34$^+$ HSPCs.

14. A primary CD34$^+$hematopoietic stem or progenitor cell comprising a ribonucleoprotein (RNP) complex comprising:
   (a) a modified single guide RNA (sgRNA) comprising a nucleotide sequence that is complementary to a sequence within the HBB gene, wherein the modified sgRNA sequence is selected from the group consisting of SEQ ID NO: 6 and SEQ ID NO: 7; and (b) a Cas polypeptide.

15. The primary CD34+ hematopoietic stem or progenitor cell of claim 14, wherein the primary CD34+ hematopoietic stem or progenitor cell comprises a mutation in the HBB gene responsible for sickle cell anemia.

16. The primary CD34+ hematopoietic stem or progenitor cell of claim 14, wherein the primary CD34+ hematopoietic stem or progenitor cell comprises a mutation in the HBB gene responsible for thalassemia.

17. The primary CD34+ hematopoietic stem or progenitor cell of claim 14, further comprising a recombinant donor repair template.

18. The primary CD34+ hematopoietic stem or progenitor cell of claim 17, wherein the recombinant donor repair template comprises two nucleotide sequences comprising two non-overlapping, homologous portions, wherein one of the two homologous portions is located at the 5' end and the other homologous portion is located at the 3' end of the recombinant donor template, wherein each homologous portion is homologous to a corresponding region of the HBB gene to undergo genome editing.

19. The primary CD34+ hematopoietic stem or progenitor cell of claim 17, wherein the recombinant donor repair template comprises a synthetic single-stranded oligodeoxynucleotide (ssODN) template comprising a nucleotide sequence encoding a mutation to correct a single nucleotide polymorphism (SNP) in the HBB gene and two nucleotide sequences comprising two non-overlapping, homologous portions that are homologous to corresponding regions of the HBB gene, wherein one of the two homologous portions is located at the 5' end and the other homologous portion is located at the 3' end of the recombinant donor template.

20. A population of primary CD34+ HSPCs comprising the primary CD34+ hematopoietic stem or progenitor cell of claim 14.

21. The population of primary CD34+ HSPCs of claim 20, wherein the population of primary CD34+ HSPCs is isolated from a subject having sickle cell anemia or thalassemia.

22. The population of primary CD34+ HSPCs of claim 20, wherein the modified sgRNA induces gene editing of HBB in at least about 30% of the population of primary CD34+ HSPCs.

* * * * *

SEQUENCE LISTING

```
<160> NUMBER OF SEQ ID NOS: 92

<210> SEQ ID NO 1
<211> LENGTH: 5688
<212> TYPE: DNA
<213> ORGANISM: Artificial Sequence
<220> FEATURE:
<223> OTHER INFORMATION: Synthetic IL2RG targeting vector sequence

<400> SEQUENCE: 1
ctaaattgta agcgttaata ttttgttaaa attcgcgtta aattttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
```

```
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccta     660
actataacgg tcctaaggta gcgattaatt aatgggagaa acaccacaga agcagagtgg     720
gttatattct ctgggtgaga gaggggagaa aattgaagct gattctgagg tttcaagtct     780
gggtgactga gagggtgacg ataccattga ctgaggtggg aaggcagga agagaagcag     840 agttggggga agatgggaag cttgaagcta gtattgttgt tcctccattt ctagaatatt     900
tttgtattat aagtcacact tcctcgccag tctcaacagg gacccagctc aggcagcagc     960
taagggtggg tattctggtt tggattagat cagaggaaag acagctgtat atgtgcccac    1020
aggagccaag acggtatttt ccatcctccc aaaacagtag agctttgaca gagatttaag    1080
ggtgaccaag tcaaggaaga ggcatggcat agaacggtga tgtcgggggt ggggggttcag   1140 aacttccatt atagaaggta atgatttaga ggagaaggtg gttgagaatg gtgctagtgg    1200
tagtgaacag atccttccca ggatctaggt gggctgagga ttttgagtc tgtgacacta     1260 ttgtatatcc agctttagtt tctgtttacc accttacagc agcacctaat ctcctagagg    1320
acttagcccg tgtcacacag cacatatttg ccacaccctc tgtaaagccc tggtttataa    1380
ggttctttcc accggaagct atgacagagg aaacgtgtgg gtggggaggg gtagtgggtg    1440
agggacccag gttcctgaca cagacagact acacccaggg aatgaagagc aagcgcctct    1500
agaattaccc tgttatccct aaggtaagta tcaaggttac aagacaggtt taaggaggcc    1560
aatagaaact gggcttgtcg agacagagaa gattcttgcg tttctgatag gcacctattg    1620
gtcttactga catccacttt gcctttctct ccacaggggt accgaagccg ctagcgctac    1680
cggtcgccac catgcccgcc atgaagatcg agtgccgcat caccggcacc ctgaacggcg    1740
tggagttcga gctggtgggc ggcggagagg gcacccccga gcagggccgc atgaccaaca    1800
agatgaagag caccaaaggc gccctgacct tcagccccta cctgctgagc cacgtgatgg    1860
gctacggctt ctaccacttc ggcacctacc ccagcggcta cgagaacccc ttcctgcacg    1920
ccatcaacaa cggcggctac accaacaccc gcatcgagaa gtacgaggac ggcggcgtgc    1980
tgcacgtgag cttcagctac cgctacgagg ccggccgcgt gatcggcgac ttcaaggtgg    2040
tgggcaccgg cttccccgag gacagcgtga tcttcaccga caagatcatc cgcagcaacg    2100
ccaccgtgga gcacctgcac cccatgggcg ataacgtgct ggtgggcagc ttcgcccgca    2160
ccttcagcct gcgcgacggc ggctactaca gcttcgtggt ggacagccac atgcacttca    2220
agagcgccat ccaccccagc atcctgcaga acggggcccc catgttcgcc ttccgccgcg    2280
tggaggagct gcacagcaac accgagctgg gcatcgtgga gtaccagcac gccttcaaga    2340
cccccatcgc cttcgccaga tctcgagctc gatgactcga gggcgcgccc cgctgatcag    2400
cctcgactgt gccttctagt tgccagccat ctgttgtttg cccctccccc gtgccttcct    2460
tgaccctgga aggtgccact cccactgtcc tttcctaata aaatgaggaa attgcatcgc    2520
attgtctgag taggtgtcat tctattctgg ggggtggggt ggggcaggac agcaagggg    2580 aggattggga agacaatagc aggcatgctg gggatgcggt gggctctatg gcttctgagg    2640
cggaaagaac gtttaaacac tagtgaagag caagcgccat gttgaagcca tcattaccat    2700
tcacatccct cttattcctg cagctgcccc tgctgggagt ggggctgaac acgacaattc    2760
tgacgcccaa tgggaatgaa gacaccacag ctggtgggaa atctgggact ggaggggct    2820
```

```
ggtgagaagg gtggctgtgg aaggggccg tacagagatc tggtgcctgc cactggccat   2880
tacaatcatg tgggcagaat tgaaaagtgg agtgggaagg gcaaggggga gggttccctg   2940
cctcacgcta cttcttcttt ctttcttgtt tgtttgtttc tttctttctt ttgaggcagg   3000
gtctcactat gttgcctagg ctggtctcaa actcctggcc tctagtgatc ctcctgcctc   3060
agcctttcaa agcaccagga ttacagacat gagccaccgt gcttggcctc ctccttctga   3120
ccatcatttc tctttccctc cctgccttca ttttctcccc aatctagatt tcttcctgac   3180
cactatgccc actgactccc tcagtgtttc cactctgccc ctcccagagg ttcagtgttt   3240
tgtgttcaat gtcgagtaca tgaattgcac ttggaacagc agctctgagc cccagcctac   3300
caacctcact ctgcattatt ggtatgagaa gggacgaggg ggaggggatg aagaagaggt   3360
gggttggatc agagaccaag agagagggta gcaagtctcc caggtacccc actgttttct   3420
cctggggtaa gtcataagtc ggtgccattt cattacctct ttctccgcac ccgacataga   3480
tgagctccag ctttttgttcc ctttagtgag ggttaattgc gcgcttggcg taatcatggt   3540
catagctgtt tcctgtgtga aattgttatc cgctcacaat tccacacaac atacgagccg   3600
gaagcataaa gtgtaaagcc tggggtgcct aatgagtgag ctaactcaca ttaattgcgt   3660
tgcgctcact gcccgctttc cagtcgggaa acctgtcgtg ccagctgcat taatgaatcg   3720
gccaacgcgc ggggagaggc ggtttgcgta ttgggcgctc ttccgcttcc tcgctcactg   3780
actcgctgcg ctcggtcgtt cggctgcggc gagcggtatc agctcactca aaggcggtaa   3840
tacggttatc cacagaatca ggggataacg caggaaagaa catgtgagca aaaggccagc   3900
aaaaggccag gaaccgtaaa aaggccgcgt tgctggcgtt tttccatagg ctccgccccc   3960
ctgacgagca tcacaaaaat cgacgctcaa gtcagaggtg gcgaaacccg acaggactat   4020
aaagatacca ggcgtttccc cctggaagct ccctcgtgcg ctctcctgtt ccgaccctgc   4080
cgcttaccgg atacctgtcc gcctttctcc cttcgggaag cgtggcgctt tctcatagct   4140
cacgctgtag gtatctcagt tcggtgtagg tcgttcgctc caagctgggc tgtgtgcacg   4200
aaccccccgt tcagcccgac cgctgcgcct tatccggtaa ctatcgtctt gagtccaacc   4260
cggtaagaca cgacttatcg ccactggcag cagccactgg taacaggatt agcagagcga   4320
ggtatgtagg cggtgctaca gagttcttga agtggtggcc taactacggc tacactagaa   4380
ggacagtatt tggtatctgc gctctgctga agccagttac cttcggaaaa agagttggta   4440
gctcttgatc cggcaaacaa accaccgctg gtagcggtgg ttttttttgt tgcaagcagc   4500
agattacgcg cagaaaaaaa ggatctcaag aagatccttt gatcttttct acggggtctg   4560
acgctcagtg gaacgaaaac tcacgttaag gattttggt catgagatta tcaaaaagga   4620
tcttcaccta gatcctttta aattaaaaat gaagttttaa atcaatctaa agtatatatg   4680
agtaaacttg gtctgacagt taccaatgct taatcagtga ggcacctatc tcagcgatct   4740
gtctatttcg ttcatccata gttgcctgac tccccgtcgt gtagataact acgatacggg   4800
agggcttacc atctggcccc agtgctgcaa tgataccgcg agacccacgc tcaccggctc   4860
cagatttatc agcaataaac cagccagccg gaagggccga gcgcagaagt ggtcctgcaa   4920
ctttatccgc ctccatccag tctattaatt gttgccggga agctagagta agtagttcgc   4980
cagttaatag tttgcgcaac gttgttgcca ttgctacagg catcgtggtg tcacgctcgt   5040
cgtttggtat ggcttcattc agctccggtt cccaacgatc aaggcgagtt acatgatccc   5100
ccatgttgtg caaaaaagcg gttagctcct tcggtcctcc gatcgttgtc agaagtaagt   5160
```

```
tggccgcagt gttatcactc atggttatgg cagcactgca taattctctt actgtcatgc    5220
catccgtaag atgctttcct gtgactggtg agtactcaac caagtcattc tgagaatagt    5280
gtatgcggcg accgagttgc tcttgcccgg cgtcaatacg ggataatacc gcgccacata    5340
gcagaacttt aaaagtgctc atcattggaa aacgttcttc ggggcgaaaa ctctcaagga    5400
tcttaccgct gttgagatcc agttcgatgt aacccactcg tgcacccaac tgatcttcag    5460
catcttttac tttcaccagc gtttctgggt gagcaaaaac aggaaggcaa aatgccgcaa    5520
aaaagggaat aagggcgaca cggaaatgtt gaatactcat actcttcctt tttcaatatt    5580
attgaagcat ttatcagggt tattgtctca tgagcggata catatttgaa tgtatttaga    5640
aaaataaaca ataggggtt ccgcgcacat ttccccgaaa agtgccac                  5688
```

<210> SEQ ID NO 2
<211> LENGTH: 7171
<212> TYPE: DNA
<213> ORGANISM: Artificial Sequence
<220> FEATURE:
<223> OTHER INFORMATION: Synthetic HBB targeting vector sequence

<400> SEQUENCE: 2

```
ctaaattgta agcgttaata ttttgttaaa attcgcgtta aattttgtt aaatcagctc       60 atttttaac caataggccg aaatcggcaa atcccttat aaatcaaaag aatagaccga      120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttgggt cgaggtgccg taaagcacta atcggaacc ctaaagggag       300 ccccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat gggtaccta    660 actataacgg tcctaaggta gcgattaatt aaaggcagaa acagttagat gtccccagtt    720
aacctcctat ttgacaccac tgattacccc attgatagtc acactttggg ttgtaagtga    780
ctttttattt atttgtattt ttgactgcat taagaggtct ctagtttttt atctcttgtt    840
tcccaaaacc taataagtaa ctaatgcaca gagcacattg atttgtattt attctatttt   900
tagacataat ttattagcat gcatgagcaa attaagaaaa acaacaacaa atgaatgcat    960
atatatgtat atgtatgtgt gtatatatac acacatatat atatatattt ttcttttct   1020 taccagaagg ttttaatcca aataaggaga agatatgctt agaaccgagg tagagttttc   1080
atccattctg tcctgtaagt attttgcata ttctggagac gcaggaagag atccatctac   1140
atatcccaaa gctgaattat ggtagacaaa actcttccac ttttagtgca tcaacttctt   1200
atttgtgtaa taagaaaatt gggaaaacga tcttcaatat gcttaccaag ctgtgattcc   1260
aaatattacg taaatacact tgcaaaggag gatgttttta gtagcaattt gtactgatgg   1320
tatgggccca agagatatat cttagaggga gggctgaggg tttgaagtcc aactcctaag   1380
ccagtgccag aagagccaag gacaggtacg gctgtcatca cttagacctc accctgtgga   1440
gccacaccct agggttggcc aatctactcc caggagcagg gagggcagga gcagggctg    1500 ggcataaaag tcagggcaga gccatctatt gcttacattt gcttctgaca caactgtgtt   1560
```

```
cactagcaac ctcaaacaga caccatggtg cacctgactc ctgaggagaa gtctgccgtt    1620
actgcccaga tctgggctcc ggtgcccgtc agtgggcaga gcgcacatcg cccacagtcc    1680
ccgagaagtt gggggagggg tcggcaatt gaaccggtgc ctagagaagg tggcgcgggg     1740
taaactggga aagtgatgtc gtgtactggc tccgccttt tcccgagggt gggggagaac     1800
cgtatataag tgcagtagtc gccgtgaacg ttcttttcg caacgggttt gccgccagaa     1860
cacaggtaag tgccgtgtgt ggttcccgcg ggcctggcct ctttacgggt tatggccctt    1920
gcgtgccttg aattacttcc acctggctgc agtacgtgat tcttgatccc gagcttcggg    1980
ttggaagtgg gtgggagagt tcgaggcctt gcgcttaagg agccccttcg cctcgtgctt    2040
gagttgaggc ctggcctggg cgctggggcc gccgcgtgcg aatctggtgg caccttcgcg    2100
cctgtctcgc tgctttcgat aagtctctag ccatttaaaa ttttttgatga cctgctgcga    2160 cgcttttttt ctggcaagat agtcttgtaa atgcgggcca agatctgcac actggtattt    2220 cggttttttgg ggccgcgggc ggcgacgggg cccgtgcgtc ccagcgcaca tgttcggcga    2280
ggcggggcct gcgagcgcgg ccaccgagaa tcggacgggg gtagtctcaa gctggccggc    2340
ctgctctggt gcctggcctc gcgccgccgt gtatcgcccc gccctgggcg gcaaggctgg    2400
cccggtcggc accagttgcg tgagcggaaa gatggccgct tcccggcct  gctgcaggga    2460 gctcaaaatg gaggacgcgg cgctcggag agcgggcggg tgagtcaccc acacaaagga    2520
aaagggcctt tccgtcctca gccgtcgctt catgtgactc cacggagtac cgggcgccgt    2580
ccaggcacct cgattagttc tcgagctttt ggagtacgtc gtctttaggt tgggggggagg    2640 ggttttatgc gatggagttt ccccacactg agtgggtgga gactgaagtt aggccagctt    2700
ggcacttgat gtaattctcc ttggaattg cccttttga gtttggatct tggttcattc      2760
tcaagcctca gacagtggtt caaagttttt ttcttccatt tcaggtgtcg tgaggtaccg    2820
agctcttcga aggatccatc gccaccatgc ccgccatgaa gatcgagtgc cgcatcaccg    2880
gcaccctgaa cggcgtggag ttcgagctgg tgggcggcgg agagggcacc cccgagcagg    2940
gccgcatgac caacaagatg aagagcacca aaggcgccct gaccttcagc ccctacctgc    3000
tgagccacgt gatgggctac ggcttctacc acttcggcac ctaccccagc ggctacgaga    3060
accccttcct gcacgccatc aacaacggcg gctacaccaa caccgcatc gagaagtacg     3120 aggacggcgg cgtgctgcac gtgagcttca gctaccgcta cgaggccggc cgcgtgatcg    3180
gcgacttcaa ggtggtgggc accggcttcc ccgaggacag cgtgatcttc accgacaaga    3240
tcatccgcag caacgccacc gtggagcacc tgcacccat gggcgataac gtgctggtgg    3300
gcagcttcgc ccgcaccttc agcctgcgcg acggcggcta ctacagcttc gtggtggaca    3360
gccacatgca cttcaagagc gccatccacc ccagcatcct gcagaacggg gcccccatgt    3420
tcgccttccg ccgcgtggag gagctgcaca gcaacaccga gctgggcatc gtggagtacc    3480
agcacgcctt caagaccccc atcgccttcg ccagatctcg agtctagctc gagggcgcgc    3540
ccgctgatca gcctcgacct gtgccttcta gttgccagcc atctgttgtt tgcccctccc    3600
ccgtgccttc cttgacccctg gaaggtgcca ctcccactgt cctttcctaa taaaatgagg    3660
aaattgcatc gcattgtctg agtaggtgtc attctattct ggggggtggg gtggggcagg    3720
acagcaaggg ggaggattgg gaagacaata gcaggcatgc tggggatgcg gtgggctcta    3780
tggcttctga ggcggaaaga acgtttcgcg cctgtgggc aaggtgaacg tggatgaagt     3840
tggtggtgag gccctgggca ggttggtatc aaggttacaa gacaggttta aggagaccaa    3900
```

```
tagaaactgg gcatgtggag acagagaaga ctcttgggtt tctgataggc actgactctc    3960
tctgcctatt ggtctatttt cccaccctta ggctgctggt ggtctaccct tggacccaga    4020
ggttctttga gtcctttggg gatctgtcca ctcctgatgc tgttatgggc aaccctaagg    4080
tgaaggctca tggcaagaaa gtgctcggtg cctttagtga tggcctggct cacctggaca    4140
acctcaaggg caccttkgcc acactgagtg agctgcactg tgacaagctg cacgtggatc    4200
```

```
cccagtgctg caatgatacc gcgagaccca cgctcaccgg ctccagattt atcagcaata    6360
aaccagccag ccggaagggc cgagcgcaga agtggtcctg caactttatc cgcctccatc    6420
cagtctatta attgttgccg ggaagctaga gtaagtagtt cgccagttaa tagtttgcgc    6480
aacgttgttg ccattgctac aggcatcgtg tgtcacgct  cgtcgtttgg tatggcttca    6540
ttcagctccg gttcccaacg atcaaggcga gttacatgat ccccatgtt  gtgcaaaaaa    6600 gcggttagct ccttcggtcc tccgatcgtt gtcagaagta agttggccgc agtgttatca    6660
ctcatggtta tggcagcact gcataattct cttactgtca tgccatccgt aagatgcttt    6720
tctgtgactg gtgagtactc aaccaagtca ttctgagaat agtgtatgcg gcgaccgagt    6780
tgctcttgcc cggcgtcaat acgggataat accgcgccac atagcagaac tttaaaagtg    6840
ctcatcattg gaaaacgttc ttcggggcga aaactctcaa ggatcttacc gctgttgaga    6900
tccagttcga tgtaacccac tcgtgcaccc aactgatctt cagcatcttt tactttcacc    6960
agcgtttctg ggtgagcaaa aacaggaagg caaaatgccg caaaaaaggg aataagggcg    7020
acacggaaat gttgaatact catactcttc ctttttcaat attattgaag catttatcag    7080
ggttattgtc tcatgagcgg atacatattt gaatgtattt agaaaaataa acaaataggg    7140
gttccgcgca catttccccg aaaagtgcca c                                   7171

<210> SEQ ID NO 3
<211> LENGTH: 7434
<212> TYPE: DNA
<213> ORGANISM: Artificial Sequence
<220> FEATURE:
<223> OTHER INFORMATION: Synthetic CCR5 targeting vector sequence

<400> SEQUENCE: 3
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc  ctaaagggag     300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccta     660
actataacgg tcctaaggta gcgattaatt aagaacagtg attggcatcc agtatgtgcc     720
ctcgaggcct cttaattatt actggcttgc tcatagtgca tgttctttgt gggctaactc     780
tagcgtcaat aaaaatgtta agactgagtt gcagccgggc atggtggctc atgcctgtaa     840
tcccagcatt ctaggaggct gaggcaggag gatcgcttga gcccaggagt tcgagaccag     900
cctgggcaac atagtgtgat cttgtatcta taaaataaaa caaaattagc ttggtgtggt     960
ggcgcctgta gtcccagcc  acttggaggg gtgaggtgag aggattgctt gagcccggga    1020
tggtccaggc tgcagtgagc catgatcgtg ccactgcact ccagcctggg cgacagagtg    1080
agaccctgtc tcaacaacaa caacaacaa  acaaaaaggc tgagctgcac catgcttgac    1140
```

```
ccagtttctt aaaattgttg tcaaagcttc attcactcca tgtgctata gagcacaaga    1200 tttatttgg tgagatggtg ctttcatgaa ttcccccaac agagccaagc tctccatcta    1260
gtggacaggg aagctagcag caaaccttcc cttcactaca aaacttcatt gcttggccaa    1320
aaagagagtt aattcaatgt agacatctat gtaggcaatt aaaaacctat tgatgtataa    1380
aacagtttgc attcatggag ggcaactaaa tacattctag gactttataa aagatcactt    1440
tttatttatg cacagggtgg aacaagatgg attatcaagt gtcaagtcca atctatgaca    1500
tcaattatta tagcgcctct agaattaccc tgttatccct aagatctggg ctccggtgcc    1560
cgtcagtggg cagagcgcac atcgcccaca gtccccgaga gttgggggg aggggtcggc    1620 aattgaaccg gtgcctagag aaggtggcgc ggggtaaact gggaaagtga tgtcgtgtac    1680
tggctccgcc tttttcccga gggtggggga gaaccgtata taagtgcagt agtcgccgtg    1740 aacgttctt ttcgcaacgg gtttgccgcc agaacacagg taagtgccgt gtgtggttcc    1800
cgcgggcctg gcctctttac gggttatggc ccttgcgtgc cttgaattac ttccacctgg    1860
ctgcagtacg tgattcttga tcccgagctt cgggttggaa gtgggtggga gagttcgagg    1920
ccttgcgctt aaggagcccc ttcgcctcgt gcttgagttg aggcctggcc tgggcgctgg    1980
ggccgccgcg tgcgaatctg gtggcacctt cgcgcctgtc tcgctgcttt cgataagtct    2040
ctagccattt aaaattttg atgacctgct gcgacgcttt ttttctggca agatagtctt    2100
gtaaatgcgg gccaagatct gcacactggt atttcggttt ttggggccgc gggcggcgac    2160
ggggcccgtg cgtcccagcg cacatgttcg gcgaggcggg gcctgcgagc gcggccaccg    2220
agaatcggac gggggtagtc tcaagctggc cggcctgctc tggtgcctgg cctcgcgccg    2280
ccgtgtatcg ccccgccctg ggcggcaagg ctggcccggt cggcaccagt tgcgtgagcg    2340
gaaagatggc cgcttcccgg ccctgctgca gggagctcaa aatggaggac gcggcgctcg    2400
ggagagcggg cgggtgagtc acccacacaa aggaaaaggg cctttccgtc ctcagccgtc    2460
gcttcatgtg actccacgga gtaccggcg ccgtccaggc acctcgatta gttctcgagc    2520
ttttggagta cgtcgtcttt aggttggggg gaggggtttt atgcgatgga gtttccccac    2580
actgagtggg tggagactga agttaggcca gcttggcact tgatgtaatt ctccttggaa    2640
tttgcccttt ttgagtttgg atcttggttc attctcaagc ctcagacagt ggttcaaagt    2700
ttttttcttc catttcaggt gtcgtgaggt accgagctct tcgaaggatc catcgccacc    2760
atggtgagca agggcgagga gctgttcacc ggggtggtgc ccatcctggt cgagctggac    2820
ggcgacgtaa acggccacaa gttcagcgtg tccggcgagg gcgagggcga tgccacctac    2880
ggcaagctga ccctgaagtt catctgcacc accggcaagc tgcccgtgcc ctggcccacc    2940
ctcgtgacca ccttcggcta cggcctgatg tgcttcgccc gctacccga ccacatgaag    3000 cagcacgact tcttcaagtc cgccatgccc gaaggctacg tccaggagcg caccatcttc    3060
ttcaaggacg acggcaacta caagacccgc gccgaggtga agttcgaggg cgacaccctg    3120
gtgaaccgca tcgagctgaa gggcatcgac ttcaaggagg acggcaacat cctggggcac    3180
aagctggagt acaactacaa cagccacaac gtctatatca tggccgacaa gcagaagaac    3240
ggcatcaagg tgaacttcaa gatccgccac aacatcgagg acggcagcgt gcagctcgcc    3300
gaccactacc agcagaacac ccccatcggc gacggccccg tgctgctgcc cgacaaccac    3360
tacctgagct accagtccaa gctgagcaaa gaccccaacg agaagcgcga tcacatggtc    3420
ctgctggagt tcgtgaccgc cgccgggatc actctcggca tggacgagct gtacaagtaa    3480
ctcgagggcg cgcctaatca acctctggat tacaaaattt gtgaaagatt gactggtatt    3540
```

```
cttaactatg ttgctccttt tacgctatgt ggatacgctg ctttaatgcc tttgtatcat    3600
gctattgctt cccgtatggc tttcattttc tcctccttgt ataaatcctg gttgctgtct    3660
ctttatgagg agttgtggcc cgttgtcagg caacgtggcg tggtgtgcac tgtgtttgct    3720
gacgcaaccc ccactggttg gggcattgcc accacctgtc agctcctttc cgggactttc    3780
gctttccccc tccctattgc cacggcggaa ctcatcgccg cctgccttgc ccgctgctgg    3840 acagggctc ggctgttggg cactgacaat tccgtggtgt tgtcgggaa atcatcgtcc      3900 tttccttggc tgctcgcctg tgttgccacc tggattctgc gcgggacgtc cttctgctac    3960
gtcccttcgg ccctcaatcc agcggacctt ccttcccgcg cctgctgcc ggctctgcgg     4020 cctcttccgc gtcttcgcct tcgccctcag acgagtcgga tctcccttttg gccgcctcc    4080 ccgcctggcg cgccccgctg atcagcctcg actgtgcctt ctagttgcca gccatctgtt    4140
gtttgcccct ccccgtgcc ttccttgacc ctggaaggtg ccactcccac tgtcctttcc     4200
taataaaatg aggaaattgc atcgcattgt ctgagtaggt gtcattctat tctgggggt     4260 gggtgggc aggacagcaa gggggaggat tgggaagaca atagcaggca tgctggggat      4320
gcggtgggct ctatggcttc tgaggcggaa agaacgttta aacactagtc tatgacatca    4380
attattatac atcggagccc tgccaaaaaa tcaatgtgaa gcaaatcgca gcccgcctcc    4440
tgcctccgct ctactcactg gtgttcatct ttggttttgt gggcaacatg ctggtcatcc    4500
tcatcctgat aaactgcaaa aggctgaaga gcatgactga catctacctg ctcaacctgg    4560
ccatctctga cctgttttc cttcttactg tccccttctg ggctcactat gctgccgccc     4620
agtgggactt tggaaataca atgtgtcaac tcttgacagg gctctatttt ataggcttct    4680
tctctggaat cttcttcatc atcctcctga caatcgatag gtacctggct gtcgtccatg    4740
ctgtgtttgc tttaaaagcc aggacggtca cctttggggt ggtgacaagt gtgatcactt    4800
gggtggtggc tgtgtttgcg tctctcccag gaatcatctt taccagatct caaaaagaag    4860
gtcttcatta cacctgcagc tctcatttc catacagtca gtatcaattc tggaagaatt      4920
tccagacatt aaagatagtc atcttggggc tggtcctgcc gctgcttgtc atggtcatct    4980
gctactcggg aatcctaaaa actctgcttc ggtgtcgaaa tgagaagaag aggcacaggg    5040
ctgtgaggct tatcttcacc atcatgattg tttatttct cttctgggct ccctacaaca     5100
ttgtccttct cctgaacacc ttccaggaat tctttggcct gaataattgc agtagctcta    5160
acaggttgga ccaagctatg caggtgactg ccatttcatt acctctttct ccgcacccga    5220
catagatgag ctccagcttt tgttcccttt agtgagggtt aattgcgcgc ttggcgtaat    5280
catggtcata gctgtttcct gtgtgaaatt gttatccgct cacaattcca cacaacatac    5340
gagccggaag cataaagtgt aaagcctggg gtgcctaatg agtgagctaa ctcacattaa    5400
ttgcgttgcg ctcactgccc gctttccagt cgggaaacct gtcgtgccag ctgcattaat    5460
gaatcggcca acgcgcgggg agaggcggtt tgcgtattgg cgctcttcc gcttcctcgc     5520 tcactgactc gctgcgctcg gtcgttcggc tgcggcgagc ggtatcagct cactcaaagg    5580
cggtaatacg gttatccaca gaatcagggg ataacgcagg aaagaacatg tgagcaaaag    5640
gccagcaaaa ggccaggaac cgtaaaaagg ccgcgttgct ggcgtttttc cataggctcc    5700
gcccccctga cgagcatcac aaaaatcgac gctcaagtca gaggtggcga aacccgacag    5760
gactataaag ataccaggcg tttccccctg gaagctccct cgtgcgctct cctgttccga    5820
ccctgccgct taccggatac ctgtccgcct ttctcccttc gggaagcgtg cgctttctc     5880
```

```
atagctcacg ctgtaggtat ctcagttcgg tgtaggtcgt tcgctccaag ctgggctgtg    5940
tgcacgaacc ccccgttcag cccgaccgct gcgccttatc cggtaactat cgtcttgagt    6000
ccaacccggt aagacacgac ttatcgccac tggcagcagc cactggtaac aggattagca    6060
gagcgaggta tgtaggcggt gctacagagt tcttgaagtg gtggcctaac tacggctaca    6120
ctagaaggac agtatttggt atctgcgctc tgctgaagcc agttaccttc ggaaaaagag    6180
ttggtagctc ttgatccggc aaacaaacca ccgctggtag cggtggtttt tttgtttgca    6240
agcagcagat tacgcgcaga aaaaaggatc tcaagaaga tcctttgatc ttttctacgg     6300
ggtctgacgc tcagtggaac gaaaactcac gttaagggat tttggtcatg agattatcaa    6360
aaaggatctt cacctagatc cttttaaatt aaaaatgaag ttttaaatca atctaaagta    6420
tatatgagta aacttggtct gacagttacc aatgcttaat cagtgaggca cctatctcag    6480
cgatctgtct atttcgttca tccatagttg cctgactccc cgtcgtgtag ataactacga    6540
tacgggaggg cttaccatct ggccccagtg ctgcaatgat accgcgagac ccacgctcac    6600
cggctccaga tttatcagca ataaaccagc cagccggaag ggccgagcgc agaagtggtc    6660
ctgcaacttt atccgcctcc atccagtcta ttaattgttg ccgggaagct agagtaagta    6720
gttcgccagt taatagtttg cgcaacgttg ttgccattgc tacaggcatc gtggtgtcac    6780
gctcgtcgtt tggtatggct tcattcagct ccggttccca acgatcaagg cgagttacat    6840 gatccccat gttgtgcaaa aaagcggtta gctccttcgg tcctccgatc gttgtcagaa     6900
gtaagttggc cgcagtgtta tcactcatgg ttatggcagc actgcataat tctcttactg    6960
tcatgccatc cgtaagatgc ttttctgtga ctggtgagta ctcaaccaag tcattctgag    7020
aatagtgtat gcggcgaccg agttgctctt gcccggcgtc aatacgggat aataccgcgc    7080
cacatagcag aactttaaaa gtgctcatca ttggaaaacg ttcttcgggg cgaaaactct    7140
caaggatctt accgctgttg agatccagtt cgatgtaacc cactcgtgca cccaactgat    7200
cttcagcatc ttttactttc accagcgttt ctgggtgagc aaaaacagga aggcaaaatg    7260
ccgcaaaaaa gggaataagg gcgacacgga aatgttgaat actcatactc ttcctttttc    7320
aatattattg aagcatttat cagggttatt gtctcatgag cggatacata tttgaatgta    7380
tttagaaaaa taaacaaata ggggttccgc gcacatttcc ccgaaaagtg ccac          7434
```

<210> SEQ ID NO 4
<211> LENGTH: 100
<212> TYPE: RNA
<213> ORGANISM: Artificial Sequence
<220> FEATURE:
<223> OTHER INFORMATION: Synthetic HBB unmodified sgRNA

<400> SEQUENCE: 4

```
cuugccccac agggcaguaa guuuuagagc uagaaauagc aaguuaaaau aaggcuaguc     60
cguuaucaac uugaaaaagu ggcaccgagu cggugcuuuu                          100
```

<210> SEQ ID NO 5
<211> LENGTH: 100
<212> TYPE: RNA
<213> ORGANISM: Artificial Sequence
<220> FEATURE:
<223> OTHER INFORMATION: Synthetic HBB M sgRNA
<220> FEATURE:
<221> NAME/KEY: modified_base
<222> LOCATION: (1)..(3)
<223> OTHER INFORMATION: Nucleotide with 2'-O-methyl modification
<220> FEATURE:
<221> NAME/KEY: modified_base

```
<222> LOCATION: (97)..(99)
<223> OTHER INFORMATION: Nucleotide with 2'-O-methyl modification

<400> SEQUENCE: 5
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 6
<211> LENGTH: 100
<212> TYPE: RNA
<213> ORGANISM: Artificial Sequence
<220> FEATURE:
<223> OTHER INFORMATION: Synthetic HBB MS sgRNA
<220> FEATURE:
<221> NAME/KEY: modified_base
<222> LOCATION: (1)..(3)
<223> OTHER INFORMATION: Nucleotide with 2'-O-methyl modification and MS
      Modification in the phosphate backbone
<220> FEATURE:
<221> NAME/KEY: modified_base
<222> LOCATION: (97)..(99)
<223> OTHER INFORMATION: Nucleotide with 2'-O-methyl modification and MS
      Modification in the phosphate backbone

<400> SEQUENCE: 6
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 7
<211> LENGTH: 100
<212> TYPE: RNA
<213> ORGANISM: Artificial Sequence
<220> FEATURE:
<223> OTHER INFORMATION: Synthetic HBB MSP sgRNA
<220> FEATURE:
<221> NAME/KEY: modified_base
<222> LOCATION: (1)..(3)
<223> OTHER INFORMATION: Nucleotide with 2'-O-methyl modification and
      MSP Modification in the phosphate backbone
<220> FEATURE:
<221> NAME/KEY: modified_base
<222> LOCATION: (97)..(99)
<223> OTHER INFORMATION: Nucleotide with 2'-O-methyl modification and
      MSP Modification in the phosphate backbone

<400> SEQUENCE: 7
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 8
<211> LENGTH: 100
<212> TYPE: RNA
<213> ORGANISM: Artificial Sequence
<220> FEATURE:
<223> OTHER INFORMATION: Synthetic IL2G unmodified sgRNA

<400> SEQUENCE: 8
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 9
<211> LENGTH: 100
<212> TYPE: RNA
<213> ORGANISM: Artificial Sequence
<220> FEATURE:
<223> OTHER INFORMATION: Synthetic IL2G M sgRNA
<220> FEATURE:
```

```
<221> NAME/KEY: modified_base
<222> LOCATION: (1)..(3)
<223> OTHER INFORMATION: Nucleotide with 2'-O-methyl modification
<220> FEATURE:
<221> NAME/KEY: modified_base
<222> LOCATION: (97)..(99)
<223> OTHER INFORMATION: Nucleotide with 2'-O-methyl modification

<400> SEQUENCE: 9
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 10
<211> LENGTH: 100
<212> TYPE: RNA
<213> ORGANISM: Artificial Sequence
<220> FEATURE:
<223> OTHER INFORMATION: Synthetic IL2G MS sgRNA
<220> FEATURE:
<221> NAME/KEY: modified_base
<222> LOCATION: (1)..(3)
<223> OTHER INFORMATION: Nucleotide with 2'-O-methyl modification and MS
      Modification in the phosphate backbone
<220> FEATURE:
<221> NAME/KEY: modified_base
<222> LOCATION: (97)..(99)
<223> OTHER INFORMATION: Nucleotide with 2'-O-methyl modification and MS
      Modification in the phosphate backbone

<400> SEQUENCE: 10
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 11
<211> LENGTH: 100
<212> TYPE: RNA
<213> ORGANISM: Artificial Sequence
<220> FEATURE:
<223> OTHER INFORMATION: Synthetic IL2G MSP sgRNA
<220> FEATURE:
<221> NAME/KEY: modified_base
<222> LOCATION: (1)..(3)
<223> OTHER INFORMATION: Nucleotide with 2'-O-methyl modification and
      MSP Modification in the phosphate backbone
<220> FEATURE:
<221> NAME/KEY: modified_base
<222> LOCATION: (97)..(99)
<223> OTHER INFORMATION: Nucleotide with 2'-O-methyl modification and
      MSP Modification in the phosphate backbone

<400> SEQUENCE: 11
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 12
<211> LENGTH: 100
<212> TYPE: RNA
<213> ORGANISM: Artificial Sequence
<220> FEATURE:
<223> OTHER INFORMATION: Synthetic CCR5 unmodified sgRNA

<400> SEQUENCE: 12
ggcagcauag ugagcccaga guuuuagagc uagaaauagc aaguuaaaau aaggcuaguc      60
cguuaucaac uugaaaaagu ggcaccgagu cggugcuuuu                          100

<210> SEQ ID NO 13
<211> LENGTH: 100
```

```
<212> TYPE: RNA
<213> ORGANISM: Artificial Sequence
<220> FEATURE:
<223> OTHER INFORMATION: Synthetic CCR5 M sgRNA
<220> FEATURE:
<221> NAME/KEY: modified_base
<222> LOCATION: (1)..(3)
<223> OTHER INFORMATION: Nucleotide with 2'-O-methyl modification
<220> FEATURE:
<221> NAME/KEY: modified_base
<222> LOCATION: (97)..(99)
<223> OTHER INFORMATION: Nucleotide with 2'-O-methyl modification

<400> SEQUENCE: 13
ggcagcauag ugagcccaga guuuuagagc uagaaauagc aaguuaaaau aaggcuaguc      60
cguuaucaac uugaaaaagu ggcaccgagu cggugcuuuu                          100

<210> SEQ ID NO 14
<211> LENGTH: 100
<212> TYPE: RNA
<213> ORGANISM: Artificial Sequence
<220> FEATURE:
<223> OTHER INFORMATION: Synthetic CCR5 MS sgRNA
<220> FEATURE:
<221> NAME/KEY: modified_base
<222> LOCATION: (1)..(3)
<223> OTHER INFORMATION: Nucleotide with 2'-O-methyl modification and MS
      Modification in the phosphate backbone
<220> FEATURE:
<221> NAME/KEY: modified_base
<222> LOCATION: (97)..(99)
<223> OTHER INFORMATION: Nucleotide with 2'-O-methyl modification and MS
      Modification in the phosphate backbone

<400> SEQUENCE: 14
ggcagcauag ugagcccaga guuuuagagc uagaaauagc aaguuaaaau aaggcuaguc      60
cguuaucaac uugaaaaagu ggcaccgagu cggugcuuuu                          100

<210> SEQ ID NO 15
<211> LENGTH: 100
<212> TYPE: RNA
<213> ORGANISM: Artificial Sequence
<220> FEATURE:
<223> OTHER INFORMATION: Synthetic CCR5 MSP sgRNA
<220> FEATURE:
<221> NAME/KEY: modified_base
<222> LOCATION: (1)..(3)
<223> OTHER INFORMATION: Nucleotide with 2'-O-methyl modification and
      MSP Modification in the phosphate backbone
<220> FEATURE:
<221> NAME/KEY: modified_base
<222> LOCATION: (97)..(99)
<223> OTHER INFORMATION: Nucleotide with 2'-O-methyl modification and
      MSP Modification in the phosphate backbone

<400> SEQUENCE: 15
ggcagcauag ugagcccaga guuuuagagc uagaaauagc aaguuaaaau aaggcuaguc      60
cguuaucaac uugaaaaagu ggcaccgagu cggugcuuuu                          100

<210> SEQ ID NO 16
<211> LENGTH: 100
<212> TYPE: RNA
<213> ORGANISM: Artificial Sequence
<220> FEATURE:
<223> OTHER INFORMATION: Synthetic CCR5 'D' MS sgRNA
<220> FEATURE:
<221> NAME/KEY: modified_base
<222> LOCATION: (1)..(3)
<223> OTHER INFORMATION: Nucleotide with 2'-O-methyl modification and MS
      Modification in the phosphate backbone
```

```
<220> FEATURE:
<221> NAME/KEY: modified_base
<222> LOCATION: (97)..(99)
<223> OTHER INFORMATION: Nucleotide with 2'-O-methyl modification and MS
      Modification in the phosphate backbone

<400> SEQUENCE: 16
ucacuaugcu gccgcccagu guuuuagagc uagaaauagc aaguuaaaau aaggcuaguc    60
cguuaucaac uugaaaaagu ggcaccgagu cggugcuuuu                        100

<210> SEQ ID NO 17
<211> LENGTH: 100
<212> TYPE: RNA
<213> ORGANISM: Artificial Sequence
<220> FEATURE:
<223> OTHER INFORMATION: Synthetic CCR5 'D' MSP sgRNA
<220> FEATURE:
<221> NAME/KEY: modified_base
<222> LOCATION: (1)..(3)
<223> OTHER INFORMATION: Nucleotide with 2'-O-methyl modification and
      MSP Modification in the phosphate backbone
<220> FEATURE:
<221> NAME/KEY: modified_base
<222> LOCATION: (97)..(99)
<223> OTHER INFORMATION: Nucleotide with 2'-O-methyl modification and
      MSP Modification in the phosphate backbone

<400> SEQUENCE: 17
ucacuaugcu gccgcccagu guuuuagagc uagaaauagc aaguuaaaau aaggcuaguc    60
cguuaucaac uugaaaaagu ggcaccgagu cggugcuuuu                        100

<210> SEQ ID NO 18
<211> LENGTH: 100
<212> TYPE: RNA
<213> ORGANISM: Artificial Sequence
<220> FEATURE:
<223> OTHER INFORMATION: Synthetic CCR5 'Q' MS sgRNA
<220> FEATURE:
<221> NAME/KEY: modified_base
<222> LOCATION: (1)..(3)
<223> OTHER INFORMATION: Nucleotide with 2'-O-methyl modification and MS
      Modification in the phosphate backbone
<220> FEATURE:
<221> NAME/KEY: modified_base
<222> LOCATION: (97)..(99)
<223> OTHER INFORMATION: Nucleotide with 2'-O-methyl modification and MS
      Modification in the phosphate backbone

<400> SEQUENCE: 18
gcuguguuug cgucucuccc guuuuagagc uagaaauagc aaguuaaaau aaggcuaguc    60
cguuaucaac uugaaaaagu ggcaccgagu cggugcuuuu                        100

<210> SEQ ID NO 19
<211> LENGTH: 100
<212> TYPE: RNA
<213> ORGANISM: Artificial Sequence
<220> FEATURE:
<223> OTHER INFORMATION: Synthetic CCR5 'Q' MSP sgRNA
<220> FEATURE:
<221> NAME/KEY: modified_base
<222> LOCATION: (1)..(3)
<223> OTHER INFORMATION: Nucleotide with 2'-O-methyl modification and
      MSP Modification in the phosphate backbone
<220> FEATURE:
<221> NAME/KEY: modified_base
<222> LOCATION: (97)..(99)
<223> OTHER INFORMATION: Nucleotide with 2'-O-methyl modification and
      MSP Modification in the phosphate backbone

<400> SEQUENCE: 19
```

-continued

```
gcuguguuug cgucucuccc guuuuagagc uagaaauagc aaguuaaaau aaggcuaguc    60
cguuaucaac uugaaaaagu ggcaccgagu cggugcuuuu                        100
```

<210> SEQ ID NO 20
<211> LENGTH: 23
<212> TYPE: DNA
<213> ORGANISM: Artificial Sequence
<220> FEATURE:
<223> OTHER INFORMATION: Synthetic CCR5 Target site sequence

<400> SEQUENCE: 20

```
ggcagcatag tgagcccaga agg                                           23
```

<210> SEQ ID NO 21
<211> LENGTH: 23
<212> TYPE: DNA
<213> ORGANISM: Artificial Sequence
<220> FEATURE:
<223> OTHER INFORMATION: Synthetic CCR5 Target site sequence

<400> SEQUENCE: 21

```
atcatcatag tgagcccaga gag                                           23
```

<210> SEQ ID NO 22
<211> LENGTH: 23
<212> TYPE: DNA
<213> ORGANISM: Artificial Sequence
<220> FEATURE:
<223> OTHER INFORMATION: Synthetic CCR5 Target site sequence

<400> SEQUENCE: 22

```
accagcagag tgagcccaga ggg                                           23
```

<210> SEQ ID NO 23
<211> LENGTH: 23
<212> TYPE: DNA
<213> ORGANISM: Artificial Sequence
<220> FEATURE:
<223> OTHER INFORMATION: Synthetic CCR5 Target site sequence

<400> SEQUENCE: 23

```
aggagcagag tgagcccaga gag                                           23
```

<210> SEQ ID NO 24
<211> LENGTH: 23
<212> TYPE: DNA
<213> ORGANISM: Artificial Sequence
<220> FEATURE:
<223> OTHER INFORMATION: Synthetic HBB Target site sequence

<400> SEQUENCE: 24

```
cttgccccac agggcagtaa cgg                                           23
```

<210> SEQ ID NO 25
<211> LENGTH: 23
<212> TYPE: DNA
<213> ORGANISM: Artificial Sequence
<220> FEATURE:
<223> OTHER INFORMATION: Synthetic HBB Target site sequence

<400> SEQUENCE: 25

```
tcagccccac agggcagtaa ggg                                           23
```

<210> SEQ ID NO 26

```
<211> LENGTH: 23
<212> TYPE: DNA
<213> ORGANISM: Artificial Sequence
<220> FEATURE:
<223> OTHER INFORMATION: Synthetic HBB Target site sequence

<400> SEQUENCE: 26
cctctcccac agggcagtaa agg                                               23

<210> SEQ ID NO 27
<211> LENGTH: 23
<212> TYPE: DNA
<213> ORGANISM: Artificial Sequence
<220> FEATURE:
<223> OTHER INFORMATION: Synthetic HBB Target site sequence

<400> SEQUENCE: 27
ttttccccaa agggcagtaa tag                                               23

<210> SEQ ID NO 28
<211> LENGTH: 23
<212> TYPE: DNA
<213> ORGANISM: Artificial Sequence
<220> FEATURE:
<223> OTHER INFORMATION: Synthetic IL2RG Target site sequence

<400> SEQUENCE: 28
tggtaatgat ggcttcaaca tgg                                               23

<210> SEQ ID NO 29
<211> LENGTH: 23
<212> TYPE: DNA
<213> ORGANISM: Artificial Sequence
<220> FEATURE:
<223> OTHER INFORMATION: Synthetic IL2RG Target site sequence

<400> SEQUENCE: 29
tgggaaggat ggcttcaaca cag                                               23

<210> SEQ ID NO 30
<211> LENGTH: 23
<212> TYPE: DNA
<213> ORGANISM: Artificial Sequence
<220> FEATURE:
<223> OTHER INFORMATION: Synthetic IL2RG Target site sequence

<400> SEQUENCE: 30
tggtgaggat ggcttcaaca cgg                                               23

<210> SEQ ID NO 31
<211> LENGTH: 23
<212> TYPE: DNA
<213> ORGANISM: Artificial Sequence
<220> FEATURE:
<223> OTHER INFORMATION: Synthetic IL2RG Target site sequence

<400> SEQUENCE: 31
tggtaatgat gacttcaaca tag                                               23

<210> SEQ ID NO 32
<211> LENGTH: 52
<212> TYPE: DNA
<213> ORGANISM: Artificial Sequence
<220> FEATURE:
<223> OTHER INFORMATION: Synthetic CCR5_ON-fwd primer sequence

<400> SEQUENCE: 32
```
cgacaggttc agagttctac agtccgacga tccaaacaca gcatggacga ca         52

<210> SEQ ID NO 33
<211> LENGTH: 55
<212> TYPE: DNA
<213> ORGANISM: Artificial Sequence
<220> FEATURE:
<223> OTHER INFORMATION: Synthetic CCR5_ON-rev  primer sequence

<400> SEQUENCE: 33
gtgactggag ttcagacgtg tgctcttccg atctggctga agagcatgac tgaca        55

<210> SEQ ID NO 34
<211> LENGTH: 54
<212> TYPE: DNA
<213> ORGANISM: Artificial Sequence
<220> FEATURE:
<223> OTHER INFORMATION: Synthetic CCR5_OFF1-fwd  primer sequence

<400> SEQUENCE: 34
cgacaggttc agagttctac agtccgacga tcggggaagc agtctggact taga        54

<210> SEQ ID NO 35
<211> LENGTH: 55
<212> TYPE: DNA
<213> ORGANISM: Artificial Sequence
<220> FEATURE:
<223> OTHER INFORMATION: Synthetic CCR5_OFF1-rev  primer sequence

<400> SEQUENCE: 35
gtgactggag ttcagacgtg tgctcttccg atctcctgcc attaaatcca ccaaa       55

<210> SEQ ID NO 36
<211> LENGTH: 51
<212> TYPE: DNA
<213> ORGANISM: Artificial Sequence
<220> FEATURE:
<223> OTHER INFORMATION: Synthetic CCR5_OFF2-fwd  primer sequence

<400> SEQUENCE: 36
cgacaggttc agagttctac agtccgacga tcagcgagtc gagttcaggt g          51

<210> SEQ ID NO 37
<211> LENGTH: 54
<212> TYPE: DNA
<213> ORGANISM: Artificial Sequence
<220> FEATURE:
<223> OTHER INFORMATION: Synthetic CCR5_OFF2-rev  primer sequence

<400> SEQUENCE: 37
gtgactggag ttcagacgtg tgctcttccg atctggctac ctaccccagg ttct        54

<210> SEQ ID NO 38
<211> LENGTH: 52
<212> TYPE: DNA
<213> ORGANISM: Artificial Sequence
<220> FEATURE:
<223> OTHER INFORMATION: Synthetic CCR5_OFF3-fwd  primer sequence

<400> SEQUENCE: 38
cgacaggttc agagttctac agtccgacga tctctcacca acactgccga at         52

<210> SEQ ID NO 39
<211> LENGTH: 55
<212> TYPE: DNA

```
<213> ORGANISM: Artificial Sequence
<220> FEATURE:
<223> OTHER INFORMATION: Synthetic CCR5_OFF3-rev   primer sequence

<400> SEQUENCE: 39
gtgactggag ttcagacgtg tgctcttccg atcttggcat atagtgctcc ccact          55

<210> SEQ ID NO 40
<211> LENGTH: 52
<212> TYPE: DNA
<213> ORGANISM: Artificial Sequence
<220> FEATURE:
<223> OTHER INFORMATION: Synthetic HBB_ON-fwd   primer sequence

<400> SEQUENCE: 40
cgacaggttc agagttctac agtccgacga tctctgtctc cacatgccca gt             52

<210> SEQ ID NO 41
<211> LENGTH: 54
<212> TYPE: DNA
<213> ORGANISM: Artificial Sequence
<220> FEATURE:
<223> OTHER INFORMATION: Synthetic HBB_ON-rev   primer sequence

<400> SEQUENCE: 41
gtgactggag ttcagacgtg tgctcttccg atctcagggc agagccatct attg           54

<210> SEQ ID NO 42
<211> LENGTH: 52
<212> TYPE: DNA
<213> ORGANISM: Artificial Sequence
<220> FEATURE:
<223> OTHER INFORMATION: Synthetic HBB_OFF1-fwd   primer sequenc

<400> SEQUENCE: 42
cgacaggttc agagttctac agtccgacga tctcccgttc tccacccaat ag             52

<210> SEQ ID NO 43
<211> LENGTH: 55
<212> TYPE: DNA
<213> ORGANISM: Artificial Sequence
<220> FEATURE:
<223> OTHER INFORMATION: Synthetic HBB_OFF1-rev   primer sequence

<400> SEQUENCE: 43
gtgactggag ttcagacgtg tgctcttccg atctgatttc caggctatgc ttcca          55

<210> SEQ ID NO 44
<211> LENGTH: 52
<212> TYPE: DNA
<213> ORGANISM: Artificial Sequence
<220> FEATURE:
<223> OTHER INFORMATION: Synthetic HBB_OFF2-fwd   primer sequence

<400> SEQUENCE: 44
cgacaggttc agagttctac agtccgacga tcgttggcag ggagacttac ca             52

<210> SEQ ID NO 45
<211> LENGTH: 55
<212> TYPE: DNA
<213> ORGANISM: Artificial Sequence
<220> FEATURE:
<223> OTHER INFORMATION: Synthetic HBB_OFF2-rev   primer sequence

<400> SEQUENCE: 45
gtgactggag ttcagacgtg tgctcttccg atctcccatg gtacgactgt tctca          55
```

<210> SEQ ID NO 46
<211> LENGTH: 52
<212> TYPE: DNA
<213> ORGANISM: Artificial Sequence
<220> FEATURE:
<223> OTHER INFORMATION: Synthetic HBB_OFF3-fwd primer sequence

<400> SEQUENCE: 46
cgacaggttc agagttctac agtccgacga tctggggcct tcaagtgttc tt         52

<210> SEQ ID NO 47
<211> LENGTH: 54
<212> TYPE: DNA
<213> ORGANISM: Artificial Sequence
<220> FEATURE:
<223> OTHER INFORMATION: Synthetic HBB_OFF3-rev primer sequenc

<400> SEQUENCE: 47
gtgactggag ttcagacgtg tgctcttccg atctgtgtgc tcctatgcct ggtt       54

<210> SEQ ID NO 48
<211> LENGTH: 52
<212> TYPE: DNA
<213> ORGANISM: Artificial Sequence
<220> FEATURE:
<223> OTHER INFORMATION: Synthetic IL2RG_ON-fwd primer sequence

<400> SEQUENCE: 48
cgacaggttc agagttctac agtccgacga tccattgggc gtcagaattg tc         52

<210> SEQ ID NO 49
<211> LENGTH: 54
<212> TYPE: DNA
<213> ORGANISM: Artificial Sequence
<220> FEATURE:
<223> OTHER INFORMATION: Synthetic IL2RG_ON-rev primer sequence

<400> SEQUENCE: 49
gtgactggag ttcagacgtg tgctcttccg atctaggttc tttccaccgg aagc       54

<210> SEQ ID NO 50
<211> LENGTH: 54
<212> TYPE: DNA
<213> ORGANISM: Artificial Sequence
<220> FEATURE:
<223> OTHER INFORMATION: Synthetic IL2RG_OFF1-fwd primer sequence

<400> SEQUENCE: 50
cgacaggttc agagttctac agtccgacga tctccggaag ttattcaagt ctga       54

<210> SEQ ID NO 51
<211> LENGTH: 54
<212> TYPE: DNA
<213> ORGANISM: Artificial Sequence
<220> FEATURE:
<223> OTHER INFORMATION: Synthetic IL2RG_OFF1-rev primer sequence

<400> SEQUENCE: 51
gtgactggag ttcagacgtg tgctcttccg atctgtctgg catcagagca caaa       54

<210> SEQ ID NO 52
<211> LENGTH: 52
<212> TYPE: DNA
<213> ORGANISM: Artificial Sequence
<220> FEATURE:

<223> OTHER INFORMATION: Synthetic IL2RG_OFF2-fwd primer sequence

<400> SEQUENCE: 52
cgacaggttc agagttctac agtccgacga tccctgggcc atatcaagag ac                52

<210> SEQ ID NO 53
<211> LENGTH: 54
<212> TYPE: DNA
<213> ORGANISM: Artificial Sequence
<220> FEATURE:
<223> OTHER INFORMATION: Synthetic IL2RG_OFF2-rev primer sequence

<400> SEQUENCE: 53
gtgactggag ttcagacgtg tgctcttccg atcttctttg gggtgatgtt tgtg            54

<210> SEQ ID NO 54
<211> LENGTH: 52
<212> TYPE: DNA
<213> ORGANISM: Artificial Sequence
<220> FEATURE:
<223> OTHER INFORMATION: Synthetic IL2RG_OFF3-fwd primer sequence

<400> SEQUENCE: 54
cgacaggttc agagttctac agtccgacga tccacaacag ttgacccagg aa                52

<210> SEQ ID NO 55
<211> LENGTH: 54
<212> TYPE: DNA
<213> ORGANISM: Artificial Sequence
<220> FEATURE:
<223> OTHER INFORMATION: Synthetic IL2RG_OFF3-rev primer sequence

<400> SEQUENCE: 55
gtgactggag ttcagacgtg tgctcttccg atctcccaac ccaggtctct gaac            54

<210> SEQ ID NO 56
<211> LENGTH: 69
<212> TYPE: DNA
<213> ORGANISM: Artificial Sequence
<220> FEATURE:
<223> OTHER INFORMATION: Synthetic P5-BC_A-fwd primer sequence

<400> SEQUENCE: 56
aatgatacgg cgaccaccga gatctacact agagctccga caggttcaga gttctacagt    60
ccgacgatc                                                              69

<210> SEQ ID NO 57
<211> LENGTH: 69
<212> TYPE: DNA
<213> ORGANISM: Artificial Sequence
<220> FEATURE:
<223> OTHER INFORMATION: Synthetic P5-BC_B-fwd primer sequence

<400> SEQUENCE: 57
aatgatacgg cgaccaccga gatctacact catagcgcga caggttcaga gttctacagt    60
ccgacgatc                                                              69

<210> SEQ ID NO 58
<211> LENGTH: 69
<212> TYPE: DNA
<213> ORGANISM: Artificial Sequence
<220> FEATURE:
<223> OTHER INFORMATION: Synthetic P5-BC_C-fwd primer sequence

<400> SEQUENCE: 58

```
aatgatacgg cgaccaccga gatctacacg tagcactcga caggttcaga gttctacagt    60
ccgacgatc                                                            69

<210> SEQ ID NO 59
<211> LENGTH: 69
<212> TYPE: DNA
<213> ORGANISM: Artificial Sequence
<220> FEATURE:
<223> OTHER INFORMATION: Synthetic P5-BC_D-fwd  primer sequence

<400> SEQUENCE: 59
aatgatacgg cgaccaccga gatctacacg ctcatagcga caggttcaga gttctacagt    60
ccgacgatc                                                            69

<210> SEQ ID NO 60
<211> LENGTH: 69
<212> TYPE: DNA
<213> ORGANISM: Artificial Sequence
<220> FEATURE:
<223> OTHER INFORMATION: Synthetic P5-BC_E-fwd  primer sequence

<400> SEQUENCE: 60
aatgatacgg cgaccaccga gatctacaca tgcatcgcga caggttcaga gttctacagt    60
ccgacgatc                                                            69

<210> SEQ ID NO 61
<211> LENGTH: 69
<212> TYPE: DNA
<213> ORGANISM: Artificial Sequence
<220> FEATURE:
<223> OTHER INFORMATION: Synthetic P5-BC_F-fwd  primer sequence

<400> SEQUENCE: 61
aatgatacgg cgaccaccga gatctacaca gtcgatccga caggttcaga gttctacagt    60
ccgacgatc                                                            69

<210> SEQ ID NO 62
<211> LENGTH: 69
<212> TYPE: DNA
<213> ORGANISM: Artificial Sequence
<220> FEATURE:
<223> OTHER INFORMATION: Synthetic P5-BC-G_fwd  primer sequence

<400> SEQUENCE: 62
aatgatacgg cgaccaccga gatctacacc actgtgacga caggttcaga gttctacagt    60
ccgacgatc                                                            69

<210> SEQ ID NO 63
<211> LENGTH: 69
<212> TYPE: DNA
<213> ORGANISM: Artificial Sequence
<220> FEATURE:
<223> OTHER INFORMATION: Synthetic P5-BC-H_fwd  primer sequence

<400> SEQUENCE: 63
aatgatacgg cgaccaccga gatctacacc gagtatccga caggttcaga gttctacagt    60
ccgacgatc                                                            69

<210> SEQ ID NO 64
<211> LENGTH: 66
<212> TYPE: DNA
```

<213> ORGANISM: Artificial Sequence
<220> FEATURE:
<223> OTHER INFORMATION: Synthetic P7-BC-A_rev  primer sequence

<400> SEQUENCE: 64
caagcagaag acggcatacg agattagagc tcgtgactgg agttcagacg tgtgctcttc    60
cgatct                                                                66

<210> SEQ ID NO 65
<211> LENGTH: 66
<212> TYPE: DNA
<213> ORGANISM: Artificial Sequence
<220> FEATURE:
<223> OTHER INFORMATION: Synthetic P7-BC_B rev  primer sequence

<400> SEQUENCE: 65
caagcagaag acggcatacg agattcatag cggtgactgg agttcagacg tgtgctcttc    60
cgatct                                                                66

<210> SEQ ID NO 66
<211> LENGTH: 66
<212> TYPE: DNA
<213> ORGANISM: Artificial Sequence
<220> FEATURE:
<223> OTHER INFORMATION: Synthetic P7-BC_C rev  primer sequence

<400> SEQUENCE: 66
caagcagaag acggcatacg agatgtagca ctgtgactgg agttcagacg tgtgctcttc    60
cgatct                                                                66

<210> SEQ ID NO 67
<211> LENGTH: 66
<212> TYPE: DNA
<213> ORGANISM: Artificial Sequence
<220> FEATURE:
<223> OTHER INFORMATION: Synthetic P7-BC_D rev  primer sequence

<400> SEQUENCE: 67
caagcagaag acggcatacg agatgctcat aggtgactgg agttcagacg tgtgctcttc    60
cgatct                                                                66

<210> SEQ ID NO 68
<211> LENGTH: 66
<212> TYPE: DNA
<213> ORGANISM: Artificial Sequence
<220> FEATURE:
<223> OTHER INFORMATION: Synthetic P7-BC_E_rev  primer sequence

<400> SEQUENCE: 68
caagcagaag acggcatacg agatatgcat cggtgactgg agttcagacg tgtgctcttc    60
cgatct                                                                66

<210> SEQ ID NO 69
<211> LENGTH: 66
<212> TYPE: DNA
<213> ORGANISM: Artificial Sequence
<220> FEATURE:
<223> OTHER INFORMATION: Synthetic P7-BC_F_rev  primer sequence

<400> SEQUENCE: 69
caagcagaag acggcatacg agatagtcga tcgtgactgg agttcagacg tgtgctcttc    60
cgatct                                                                66

<210> SEQ ID NO 70
<211> LENGTH: 66
<212> TYPE: DNA
<213> ORGANISM: Artificial Sequence
<220> FEATURE:
<223> OTHER INFORMATION: Synthetic P7-BC-G_ rev primer sequence

<400> SEQUENCE: 70

```
caagcagaag acggcatacg agatcactgt gagtgactgg agttcagacg tgtgctcttc    60
cgatct                                                               66
```

<210> SEQ ID NO 71
<211> LENGTH: 66
<212> TYPE: DNA
<213> ORGANISM: Artificial Sequence
<220> FEATURE:
<223> OTHER INFORMATION: Synthetic P7-BC-H_rev  primer sequence

<400> SEQUENCE: 71

```
caagcagaag acggcatacg agatcgagta tcgtgactgg agttcagacg tgtgctcttc    60
cgatct                                                               66
```

<210> SEQ ID NO 72
<211> LENGTH: 228
<212> TYPE: DNA
<213> ORGANISM: Artificial Sequence
<220> FEATURE:
<223> OTHER INFORMATION: Synthetic CCR5 ON target amplicon

<400> SEQUENCE: 72

```
caaacacagc atggacgaca gccaggtacc tatcgattgt caggaggatg atgaagaaga    60
ttccagagaa gaagcctata aaatagagcc ctgtcaagag ttgacacatt gtatttccaa   120
agtcccactg ggcggcagca tagtgagccc agaaggggac agtaagaagg aaaaacaggt   180
cagagatggc caggttgagc aggtagatgt cagtcatgct cttcagcc                228
```

<210> SEQ ID NO 73
<211> LENGTH: 225
<212> TYPE: DNA
<213> ORGANISM: Artificial Sequence
<220> FEATURE:
<223> OTHER INFORMATION: Synthetic CCR5 OFF1 target amplicon

<400> SEQUENCE: 73

```
ggggaagcag tctggactta gaaaggaaat aggtggtctg tcatagggc tttcattaga     60 gttaaacttc atagagtcaa ctgtttcatc atcatagtga gcccagagag ccactgccca   120
gcagcatgct cacaccacct accctagtgt aggtaatagg tctacgctag gaccccgtgc   180
tgggctctca gcccatcatg agattttggt ggatttaatg gcagg                  225
```

<210> SEQ ID NO 74
<211> LENGTH: 183
<212> TYPE: DNA
<213> ORGANISM: Artificial Sequence
<220> FEATURE:
<223> OTHER INFORMATION: Synthetic CCR5 OFF2 target amplicon

<400> SEQUENCE: 74

```
agcgagtcga gttcaggtgg gagcagaggg cgcccaccag cagagcgagt cgagtccagg    60
cgggagcaga gggcgcacac cagcagagtg agcccagagg gtttaaagaa ggggcggtct   120
```

```
ctacggtatg ggtagagtca ggggaactag gaaaggacag agcagaacct ggggtaggta    180
gcc                                                                  183

<210> SEQ ID NO 75
<211> LENGTH: 216
<212> TYPE: DNA
<213> ORGANISM: Artificial Sequence
<220> FEATURE:
<223> OTHER INFORMATION: Synthetic CCR5 OFF3 target amplicon

<400> SEQUENCE: 75
tctcaccaac actgccgaat gtcatctctt ctcatcttta tctctattct ttgcttcctg    60
tcttcagggc tcttcccttg gcattcacca ggagcagagt gagcccagag agctgagtgg    120
tatcccttct tcttgggtcc ctgagccctg acctggagca atgctgtgag acagcaggaa    180
aggaggggag tgtggagtgg ggagcactat atgcca                              216

<210> SEQ ID NO 76
<211> LENGTH: 229
<212> TYPE: DNA
<213> ORGANISM: Artificial Sequence
<220> FEATURE:
<223> OTHER INFORMATION: Synthetic HBB ON target amplicon

<400> SEQUENCE: 76
tctgtctcca catgcccagt ttctattggt ctccttaaac ctgtcttgta accttgatac    60
caacctgccc agggcctcac caccaacttc atccacgttc accttgcccc acagggcagt    120
aacggcagac ttctcctcag gagtcagatg caccatggtg tctgtttgag gttgctagtg    180
aacacagttg tgtcagaagc aaatgtaagc aatagatggc tctgccctg                229

<210> SEQ ID NO 77
<211> LENGTH: 230
<212> TYPE: DNA
<213> ORGANISM: Artificial Sequence
<220> FEATURE:
<223> OTHER INFORMATION: Synthetic HBB  OFF1 target amplicon

<400> SEQUENCE: 77
tcccgttctc cacccaatag ctatggaaag gggaagatcc cagagaactt ggataggaaa    60
ggtgaagtca gagcagtgct tcagccccac agggcagtaa gggcagcctt cctctaaata    120
ccagattccc aaatctggct gtgctttcaa tttgggagtt ggacatactg ctaaactata    180
atttcttagg ccgtacctaa aatatattat ggaagcatag cctggaaatc                230

<210> SEQ ID NO 78
<211> LENGTH: 229
<212> TYPE: DNA
<213> ORGANISM: Artificial Sequence
<220> FEATURE:
<223> OTHER INFORMATION: Synthetic HBB  OFF2 target amplicon

<400> SEQUENCE: 78
gttggcaggg agacttacca gcttcccgta tctccctcca catggaggca ggacacgctc    60
tggccttgcc caccctccca ctagcctctc ccacagggca gtaaaggtga gtctgggaga    120
aagaaccggt cagacttagt tcagctccac cctttcctcc tgggagtgag tctttccaag    180
acagagcatg ttttttttcta cccctcagtg agaacagtcg taccatggg                229

<210> SEQ ID NO 79
<211> LENGTH: 220
```

```
<212> TYPE: DNA
<213> ORGANISM: Artificial Sequence
<220> FEATURE:
<223> OTHER INFORMATION: Synthetic HBB  OFF3 target amplicon

<400> SEQUENCE: 79
tggggccttc aagtgttctt cccaagagtc agagtgaacc agaaccaaga accatgttga      60
gttgcccaga tgtaaccagg cctacaggta cctgggagaa acacgtgtac attttcccca    120
aagggcagta atagcatcct aggcttcaaa acattcatag aaaccatttt tcaaatgcaa    180
agtccaacac agttagaaat aaccaggcat aggagcacac                          220

<210> SEQ ID NO 80
<211> LENGTH: 212
<212> TYPE: DNA
<213> ORGANISM: Artificial Sequence
<220> FEATURE:
<223> OTHER INFORMATION: Synthetic IL2RG  ON target amplicon

<400> SEQUENCE: 80
cattgggcgt cagaattgtc gtgttcagcc ccactcccag caggggcagc tgcaggaata     60
agagggatgt gaatggtaat gatggcttca acatggcgct tgctcttcat tccctgggtg    120
tagtctgtct gtgtcaggaa cctgggtccc tcacccacta ccctccccca cccacacgtt    180
tcctctgtca tagcttccgg tggaaagaac ct                                   212

<210> SEQ ID NO 81
<211> LENGTH: 219
<212> TYPE: DNA
<213> ORGANISM: Artificial Sequence
<220> FEATURE:
<223> OTHER INFORMATION: Synthetic IL2RG  OFF1 target amplicon

<400> SEQUENCE: 81
tccggaagtt attcaagtct gattttcttt cctcccttgt cagggaaaag aagttgtgac     60
aaattgcttg gatccttaag cttaagtggg aaggatggct tcaacacaga acatctgttt    120
cattgctgtt ttatccgtca gtaaaactgt tacttctttt atgtactaaa agttcttagc    180
acttaactaa tattagctct ttgtgctctg atgccagac                            219

<210> SEQ ID NO 82
<211> LENGTH: 227
<212> TYPE: DNA
<213> ORGANISM: Artificial Sequence
<220> FEATURE:
<223> OTHER INFORMATION: Synthetic IL2RG  OFF2 target amplicon

<400> SEQUENCE: 82
cctgggccat atcaagagac tctgcctcaa aaagaaaag aaagaaagaa aagaaaaaa      60 aaagaacat cattaaaaat ccctgaggag catttagagt attgggtggc acaaacagat    120
tctgcatgat tggtgaggat ggcttcaaca cggcagcttt attcctcttt aacagagtca    180
gcagcatcaa ggcatgaggg atcttggcac aaacatcacc ccaaaga                  227

<210> SEQ ID NO 83
<211> LENGTH: 221
<212> TYPE: DNA
<213> ORGANISM: Artificial Sequence
<220> FEATURE:
<223> OTHER INFORMATION: Synthetic IL2RG  OFF3 target amplicon

<400> SEQUENCE: 83
```

```
cacaacagtt gacccaggaa caggggggaac ctcccaccat tcccatccca ctgtttgatc    60
agatccaaga atccacaata ttgagagtga atgaaaagtg tcagctggta atgatgactt   120
caacatagtc agaactcttt ggggtgttcc aaacatcatg gtgcatatgt attacctggg   180
agtcttgtta aaaagactcc tgttcagaga cctgggttgg g                       221
```

<210> SEQ ID NO 84
<211> LENGTH: 30
<212> TYPE: DNA
<213> ORGANISM: Artificial Sequence
<220> FEATURE:
<223> OTHER INFORMATION: synthetic IL2RG_fw primer

<400> SEQUENCE: 84

```
tcacacagca catatttgcc acccctctg                                      30
```

<210> SEQ ID NO 85
<211> LENGTH: 27
<212> TYPE: DNA
<213> ORGANISM: Artificial Sequence
<220> FEATURE:
<223> OTHER INFORMATION: synthetic IL2RG_RV primer

<400> SEQUENCE: 85

```
tgcccacatg attgtaatgg ccagtgg                                        27
```

<210> SEQ ID NO 86
<211> LENGTH: 27
<212> TYPE: DNA
<213> ORGANISM: Artificial Sequence
<220> FEATURE:
<223> OTHER INFORMATION: synthetic HBB_fw primer

<400> SEQUENCE: 86

```
ccaactccta agccagtgcc agaagag                                        27
```

<210> SEQ ID NO 87
<211> LENGTH: 27
<212> TYPE: DNA
<213> ORGANISM: Artificial Sequence
<220> FEATURE:
<223> OTHER INFORMATION: synthetic CCR5_fw primer

<400> SEQUENCE: 87

```
agtcagtgcc tatcagaaac ccaagag                                        27
```

<210> SEQ ID NO 88
<211> LENGTH: 21
<212> TYPE: DNA
<213> ORGANISM: Artificial Sequence
<220> FEATURE:
<223> OTHER INFORMATION: synthetic CCR5_rv primer

<400> SEQUENCE: 88

```
gcacagggtg gaacaagatg g                                              21
```

<210> SEQ ID NO 89
<211> LENGTH: 21
<212> TYPE: DNA
<213> ORGANISM: Artificial Sequence
<220> FEATURE:
<223> OTHER INFORMATION: synthetic primer

<400> SEQUENCE: 89

```
caccacccca aaggtgaccg t                                              21
```

```
<210> SEQ ID NO 90
<211> LENGTH: 25
<212> TYPE: DNA
<213> ORGANISM: Artificial Sequence
<220> FEATURE:
<223> OTHER INFORMATION: synthetic primer

<400> SEQUENCE: 90
ggctgttgtc atctatgacc ttccc                                               25

<210> SEQ ID NO 91
<211> LENGTH: 23
<212> TYPE: DNA
<213> ORGANISM: Artificial Sequence
<220> FEATURE:
<223> OTHER INFORMATION: synthetic primer

<400> SEQUENCE: 91
tgtaaactga gcttgctcgc tcg                                                 23

<210> SEQ ID NO 92
<211> LENGTH: 21
<212> TYPE: DNA
<213> ORGANISM: Artificial Sequence
<220> FEATURE:
<223> OTHER INFORMATION: synthetic primer

<400> SEQUENCE: 92
gcacagggtg gaacaagatg g                                                   21
```